(12) United States Patent
Bundock

(10) Patent No.: US 9,624,506 B2
(45) Date of Patent: Apr. 18, 2017

(54) GLYPHOSATE RESISTANCE ENHANCEMENT

(71) Applicant: Keygene N.V., Wageningen (NL)

(72) Inventor: Paul Bundock, Wageningen (NL)

(73) Assignee: KEYGENE N.V., Wageningen (NL)

( * ) Notice: Subject to any disclaimer, the term of this patent is extended or adjusted under 35 U.S.C. 154(b) by 0 days.

(21) Appl. No.: 14/640,700

(22) Filed: Mar. 6, 2015

(65) Prior Publication Data

US 2015/0191741 A1 Jul. 9, 2015

Related U.S. Application Data

(63) Continuation of application No. 14/114,599, filed as application No. PCT/NL2012/050290 on Apr. 27, 2012, now abandoned.

(60) Provisional application No. 61/480,623, filed on Apr. 29, 2011.

(51) Int. Cl.
   C12N 15/82 (2006.01)
   C12N 9/10 (2006.01)

(52) U.S. Cl.
   CPC ....... *C12N 15/8275* (2013.01); *C12N 9/1092* (2013.01)

(58) Field of Classification Search
   None
   See application file for complete search history.

(56) References Cited

U.S. PATENT DOCUMENTS

| 5,310,667 A | 5/1994 | Eichholtz |
| 6,391,374 B1 * | 5/2002 | Gray et al. ............ 426/634 |
| 2003/0233675 A1 * | 12/2003 | Cao .................. C07K 14/195 800/279 |
| 2006/0143727 A1 * | 6/2006 | Alibhai ............. C12N 9/1092 800/278 |
| 2014/0206850 A1 | 7/2014 | Bundock |
| 2015/0191741 A1 | 7/2015 | Bundock |

FOREIGN PATENT DOCUMENTS

WO   WO 2012/148275 A1   11/2012

OTHER PUBLICATIONS

GenBann NCBI Reference Sequence XP_002538414.1.*
DiTomaso, J.M, G.B., Kyser, et al. 2013. Weed Control in Natural Areas in the Western United States. Weed Research and Information Center, University of California. 544pp.*
Friedberg, I. "Automated protein function prediction—the genomic challenge." Briefings in bioinformatics 7.3 (2006): 225-242.*

(Continued)

*Primary Examiner* — Russell Kallis
*Assistant Examiner* — Fan Weihua
(74) *Attorney, Agent, or Firm* — Finnegan, Henderson, Farabow, Garrett & Dunner, L.L.P.

(57) ABSTRACT

The present invention relates to a new method for improving glyphosate resistance of a plant. The method encompasses providing one or more specific mutations in a specific nucleotide sequence in said plant. In comparison to a plant not manipulated according to the method, the plant obtained by the method displays (improved) glyphosate resistance. Also provided are a (transgenic) plant, including a seed thereof, and a plant product that can be obtained by the method according to the invention.

30 Claims, 23 Drawing Sheets

(56) References Cited

OTHER PUBLICATIONS

Benbrook, C., "Evidence of the Magnitude and Consequences of the Roundup Ready Soybean Yield Drag from University-Based Varietal Trials in 1998," Ag Bio Tech InfoNet Technical Paper No. 1, 28 pages (1999).
"Acreage," Released Jun. 30, 2005, by the National Agricultural Statistics Service (NASS), Agricultural Statistics Board, U.S. Department of Agriculture, pp. 1-43.
Gasser, C.S., et al., "Structure, Expression, and Evolution of the 5-Enolpyruvylshikimate-3-phosphate Synthase Genes of Petunia and Tomato," The Journal of Biological Chemistry, vol. 263, No. 9, pp. 4280-4287 (1988).
Baerson, S.R., et al., "Glyphosate-Resistant Goosegrass. Identification of a Mutation in the Target Enzyme 5-Enolpyruvylshikimate-3-Phosphate Synthase," Plant Physiology, vol. 129, pp. 1265-1275 (2002).
Pline-Srnic, W., "Physiological mechanisms of glyphosate resistance," Weed Technology 20, No. 2, pp. 290-300 (2006).
He, M. et al.,"A New Type of Class I Bacterial 5-Enopyruvyslhikimate-3-phosphate Synthase Mutants with Enhanced Tolerance to Glyphosate," Biochimica et Biophysica Acta 1568, No. 1, pp. 1-6 (2001).
First Office Action issued by the State Intellectual Property Office of China on Dec. 1, 2014, for Chinese Application No. 201280020879.5.
Japanese Office Action dated Feb. 29, 2016 for Application No. 2014-508310.
Canadian Office Action Appln. No. 2,833,613 dated Oct. 26, 2016.

\* cited by examiner

```
                               N44D
                  20            40                     60                      80
                  |             ▼                      |                       |
      Maize  -AEEIVLQPI KEISGTVKLP GSKSLSNRIL LLAALSEGTT VVDNLLNSED VHYMLGALRT LGLSVEADKA AKRAVVVGCG 79
       Rice  KAEEIVLQPI REISGAVQLP GSKSLSNRIL LLSALSEGTT VVDNLLNSED VHYMLEALKA LGLSVEADKV AKRAVVVGCG 80
      Wheat  GAEEVVLQPI REISGAVQLP GSKSLSNRIL LLSALSEGTT VVDNLLNSED VHYMLEALEA LGLSVEADKV AKRAVVVGCG 80
     Tomato  KPHEIVLXPI KDISGTVKLP GSKSLSNRIL LLAALSEGRT VVDNLLSSDD IHYMLGALKT LGLHVEDDNE NQRAIVEGCG 80
 Arabidopsis KASEIVLQPI REISGLIKLP GSKSLSNRIL LLAALSEGTT VVDNLLNSDD INYMLDALKR LGLNVETDSE NNRAVVEGCG 80
      Onion  .......... ....GTVKLP GSKSLSNRIL LLAALAEGTT VVDNLLNSDD VSYMLAALKT LGLSVEDDRM NKRAIVVGSG 66
  Salmonella --esltlqpl arvdgainip gsksvsnral llaalpcgkt altnlldsdd vrhminalsa lginytlsad rlrcdllgng 78
      E.coli --esltlqpl arvdgtinip gksksvsnral llaalahgkt vltnlldsdd vrhminalig lgvsytlsod rlrcollgng 78
                                  G101A P106L                  125                      140                      100
                                   |    ▼                       |                       |                       |
                                   ▼
      Maize  GKFPVE-DAK EEVQLFLGNA GTAMRPLTAA VTAAGGNATY VLDGVPRMRE RPIGDLVVGL KQLGADVDCF LGTDCPPVRV 158
       Rice  GKFPVEKDAK EEVQLFLGNA GTAMRPLTAA VTAAGGNATY VLDGVPRMRE RPIGDLVVGL KQLGADVDCF LGTECPPVRV 160
      Wheat  GRFPVEKDAQ EEVKLFLGNA GTAMRPLTAA VVAAGGNATY VLDGVPRMRE RPIGDLVVGL QQLGADADCF LGTNCPPVRI 160
     Tomato  GQFPVGKKSE EEIQLFLGNA GTAMRPLTAA VTVAGGHSRY VLDGVPRMRE RPIGDLVDGL KQLGAEVDCS LGTNCPPVRI 160
 Arabidopsis GIFPASIDSK SQIELYLGNA GTAMRPLTAA VTAAGGNASY VLDGVPRMRE RPIGDLVVGL KQLGADVECT LGTNCPPVRV 160
      Onion  GLFPVGKESQ VEVQLFLGNA GTAMRPLTAA VTAAGGNASY ILDGVPRMRE RPIGDLVVGL KQLGADVDCT LGTDCPPVRV 146
  Salmonella gal----rep galelfigne gtamrplaaa l--clgqnel vltgeprmko rplghlvdsl rqgganidyl aqanyppirl 152
      E.coli gpl----hae galelfigna gtamrplaaa l--clgsndl vltgeprmke rplghlvdal rlggskltyl aqanyppirl 152
                                  S179N                200
                                   ▼                    |
      Maize  NGIGGLPGGK VKLSGSISSQ YLSALLMAAP LALGDVE... . 195
       Rice  KGIGGLPGGK VKLSGSISSQ YLSALLMAAP LALGDVE... . 197
      Wheat  NGKGGLPGGK VKLSGSISSQ YLSSLLMAAP LALEDVE... . 197
     Tomato  VSKGGLPGGK VKLSGSISSQ YLTALLMAAP LALGDVE... . 197
 Arabidopsis NANGGLPGGK VKLSGSISSQ YLTALLMSAP LALGDVE... . 197
      Onion  NANGGLPGGK VKLSGSISSQ YLTALLMAAP LALGDVE... . 183
  Salmonella r--ggftggd lavdgsvasq lltallmtap lapkdll... . 187
      E.coli q--ggftqgn vdvdgsvasq lltallmtap lapedlv... . 187
```

```
  1 MAQVSRICNG VQNPSLISNL SKSSQRKSPL SVSLKTQQHP RAYPISSSWG LKKSGMTLIG
 61 SELRPLKVMS SVSTAEKASE IVLQPIREIS GLIKLPGSKS LSNRILLLAA LSEGTTVVDN
121 LLNSDDINYM LDALKRLGLN VETDSENNRA VVEGCGGIFP ASIDSKSDIE LYLGNAGTAM
181 RPLTAAVTAA GGNASYVLDG VPRMRERPIG DLVVGLKQLG ADVECTLGTN CPPVRVNANG
241 GLPGGKVKLS GSISSQYLTA LLMSAPLALG DVEIEIVDKL ISVPYVEMTL KLMERFGVSV
301 EHSDSWDRFF VKGGQKYKSP GNAYVEGDAS SASYFLAGAA ITGETVTVEG CGTTSLQGDV
361 KFAEVLEKMG CKVSWTENSV TVTGPPRDAF GMRHLRAIDV NMNKMPDVAM TLAVVALFAD
421 GPTTIRDVAS WRVKETERMI AICTELRKLG ATVEEGSDYC VITPPKKVKT AEIDTYDDHR
481 MAMAFSLAAC ADVPITINDP GCTRKTFPDY FQVLERITKH *
```

Figure 4

ATGGCGCAAGTTAGCAGAATCTGCAATGGTGTGCAGAACCCATCTCTTATCTCCAATCTCT
CGAAATCCAGTCAACGCAAATCTCCCTTATCGGTTTCTCTGAAGACGCAGCAGCATCCACG
AGCTTATCCGATTTCGTCGTCGTGGGGATTGAAGAAGAGTGGGATGACGTTAATTGGCTCT
GAGCTTCGTCCTCTTAAGGTCATGTCTTCTGTTTCCACGGCGGAGAAAGCGTCGGAGATTG
TACTTCAACCCATTAGAGAAATCTCCGGTCTTATTAAGCTTCCTGGCTCCAAGTCTCTATCA
AATCGAATCCTGCTTCTCGCTGCTCTGTCTGAGGGAACAACTGTAGTGGACAACTTGTTGA
ATAGCGATGACATCAATTACATGCTTGATGCGTTGAAGAGATTGGGACTTAATGTGGAAAC
TGACAGTGAAAATAATCGTGCTGTAGTTGAAGGATGTGGCGGGATATTCCCAGCTTCCATA
GATTCAAAGAGTGATATCGAACTTTACCTCGGTAATGCAGGAACAGCAATGCGTCCACTTA
CCGCTGCGGTCACTGCTGCAGGTGGAAACGCAAGTTATGTGCTTGATGGGGTGCCTCGTA
TGAGAGAAAGACCTATAGGGGATTTGGTTGTTGGTCTTAAGCAGCTTGGTGCTGATGTTGA
ATGTACTCTTGGAACTAACTGCCCTCCTGTTCGTGTCAACGCTAATGGTGGCCTTCCCGGT
GGAAAGGTGAAGCTTTCTGGATCAATTAGTAGTCAGTACTTGACTGCTCTGCTCATGTCTG
CTCCCTTAGCTCTTGGAGACGTCGAGATTGAGATTGTCGATAAATTAATTTCTGTTCCATAT
GTTGAAATGACATTGAAGTTGATGGAACGTTTCGGGGTTAGTGTCGAGCATAGTGATAGCT
GGGATCGTTTCTTTGTCAAGGGCGGGCAAAAATACAAGTCTCCGGGTAATGCGTATGTAG
AAGGTGATGCTTCTAGTGCTAGTTATTTCTTGGCTGGTGCTGCCATTACCGGTGAAACTGT
CACAGTCGAAGGTTGTGGAACTACCAGCTTGCAGGGAGATGTAAAATTCGCCGAGGTCCT
TGAGAAAATGGGATGTAAAGTGTCCTGGACAGAGAACAGTGTGACTGTGACAGGACCACC
TAGAGATGCTTTTGGAATGAGACACTTGCGGGCTATTGATGTCAACATGAACAAAATGCCT
GATGTAGCCATGACCCTTGCCGTCGTTGCTCTCTTTGCTGACGGTCCAACCACCATTAGAG
ATGTGGCTAGCTGGAGAGTAAAGGAGACAGAAAGGATGATTGCCATTTGCACAGAGCTTA
GAAAACTGGGAGCTACAGTGGAAGAAGGTTCAGATTATTGTGTGATAACTCCGCCCAAAAA
GGTGAAAACGGCAGAGATTGATACATATGATGATCATAGAATGGCAATGGCATTCTCTCTT
GCAGCTTGTGCTGATGTTCCAATCACCATCAACGATCCTGGTTGCACCAGGAAAACCTTCC
CCGACTACTTCCAAGTACTTGAAAGAATCACAAAGCAC

Figure 5

ATGGCGCAAGTTAGCAGAATCTGCAATGGTGTGCAGAACCCATCTCTTATCTCCAATCTCT
CGAAATCCAGTCAACGCAAATCTCCCTTATCGGTTTCTCTGAAGACGCAGCAGCATCCACG
AGCTTATCCGATTTCGTCGTCGTGGGGATTGAAGAAGAGTGGGATGACGTTAATTGGCTCT
GAGCTTCGTCCTCTTAAGGTCATGTCTTCTGTTTCCACGGCGGAGAAAGCGTCGGAGATTG
TACTTCAACCCATTAGAGAAATCTCCGGTCTTATTAAGCTTCCTGGCTCCAAGTCTCTATCA
AATCGAATCCTGCTTCTCGCTGCTCTGTCTGAGGGAACAACTGTAGTGGAC<u>G</u>ACTTGTTGA
ATAGCGATGACATCAATTACATGCTTGATGCGTTGAAGAGATTGGGACTTAATGTGGAAAC
TGACAGTGAAAATAATCGTGCTGTAGTTGAAGGATGTGGCGGGATATTCCCAGCTTCCATA
GATTCAAAGAGTGATATCGAACTTTACCTCGGTAATGCAGGAACAGCAATGCGTCCACTTA
CCGCTGCGGTCACTGCTGCAGGTGGAAACGCAAGTTATGTGCTTGATGGGGTGCCTCGTA
TGAGAGAAAGACCTATAGGGGATTTGGTTGTTGGTCTTAAGCAGCTTGGTGCTGATGTTGA
ATGTACTCTTGGAACTAACTGCCCTCCTGTTCGTGTCAACGCTAATGGTGGCCTTCCCGGT
GGAAAGGTGAAGCTTTCTGGATCAATTAGTAGTCAGTACTTGACTGCTCTGCTCATGTCTG
CTCCCTTAGCTCTTGGAGACGTCGAGATTGAGATTGTCGATAAATTAATTTCTGTTCCATAT
GTTGAAATGACATTGAAGTTGATGGAACGTTTCGGGGTTAGTGTCGAGCATAGTGATAGCT
GGGATCGTTTCTTTGTCAAGGGCGGGCAAAAATACAAGTCTCCGGGTAATGCGTATGTAG
AAGGTGATGCTTCTAGTGCTAGTTATTTCTTGGCTGGTGCTGCCATTACCGGTGAAACTGT
CACAGTCGAAGGTTGTGGAACTACCAGCTTGCAGGGAGATGTAAAATTCGCCGAGGTCCT
TGAGAAAATGGGATGTAAAGTGTCCTGGACAGAGAACAGTGTGACTGTGACAGGACCACC
TAGAGATGCTTTTGGAATGAGACACTTGCGGGCTATTGATGTCAACATGAACAAAATGCCT
GATGTAGCCATGACCCTTGCCGTCGTTGCTCTCTTTGCTGACGGTCCAACCACCATTAGAG
ATGTGGCTAGCTGGAGAGTAAAGGAGACAGAAAGGATGATTGCCATTTGCACAGAGCTTA
GAAAACTGGGAGCTACAGTGGAAGAAGGTTCAGATTATTGTGTGATAACTCCGCCCAAAAA
GGTGAAAACGGCAGAGATTGATACATATGATGATCATAGAATGGCAATGGCATTCTCTCTT
GCAGCTTGTGCTGATGTTCCAATCACCATCAACGATCCTGGTTGCACCAGGAAAACCTTCC
CCGACTACTTCCAAGTACTTGAAAGAATCACAAAGCAC

The mutation A358G is underlined

Figure 6

ATGGCGCAAGTTAGCAGAATCTGCAATGGTGTGCAGAACCCATCTCTTATCTCCAATCTCT
CGAAATCCAGTCAACGCAAATCTCCCTTATCGGTTTCTCTGAAGACGCAGCAGCATCCACG
AGCTTATCCGATTTCGTCGTCGTGGGGATTGAAGAAGAGTGGGATGACGTTAATTGGCTCT
GAGCTTCGTCCTCTTAAGGTCATGTCTTCTGTTTCCACGGCGGAGAAAGCGTCGGAGATTG
TACTTCAACCCATTAGAGAAATCTCCGGTCTTATTAAGCTTCCTGGCTCCAAGTCTCTATCA
AATCGAATCCTGCTTCTCGCTGCTCTGTCTGAGGGAACAACTGTAGTGGACAACTTGTTGA
ATAGCGATGACATCAATTACATGCTTGATGCGTTGAAGAGATTGGGACTTAATGTGGAAAC
TGACAGTGAAAATAATCGTGCTGTAGTTGAAGGATGTGGCGGGATATTCCCAGCTTCCATA
GATTCAAAGAGTGATATCGAACTTTACCTCGGTAATGCAGGAACAGCAATGCGTCTACTTA
CCGCTGCGGTCACTGCTGCAGGTGGAAACGAAGTTATGTGCTTGATGGGGTGCCTCGTA
TGAGAGAAAGACCTATAGGGGATTTGGTTGTTGGTCTTAAGCAGCTTGGTGCTGATGTTGA
ATGTACTCTTGGAACTAACTGCCCTCCTGTTCGTGTCAACGCTAATGGTGGCCTTCCCGGT
GGAAAGGTGAAGCTTTCTGGATCAATTAGTAGTCAGTACTTGACTGCTCTGCTCATGTCTG
CTCCCTTAGCTCTTGGAGACGTCGAGATTGAGATTGTCGATAAATTAATTTCTGTTCCATAT
GTTGAAATGACATTGAAGTTGATGGAACGTTTCGGGGTTAGTGTCGAGCATAGTGATAGCT
GGGATCGTTTCTTTGTCAAGGGCGGGCAAAAATACAAGTCTCCGGGTAATGCGTATGTAG
AAGGTGATGCTTCTAGTGCTAGTTATTTCTTGGCTGGTGCTGCCATTACCGGTGAAACTGT
CACAGTCGAAGGTTGTGGAACTACCAGCTTGCAGGGAGATGTAAAATTCGCCGAGGTCCT
TGAGAAAATGGGATGTAAAGTGTCCTGGACAGAGAACAGTGTGACTGTGACAGGACCACC
TAGAGATGCTTTTGGAATGAGACACTTGCGGGCTATTGATGTCAACATGAACAAAATGCCT
GATGTAGCCATGACCCTTGCCGTCGTTGCTCTCTTTGCTGACGGTCCAACCACCATTAGAG
ATGTGGCTAGCTGGAGAGTAAAGGAGACAGAAAGGATGATTGCCATTTGCACAGAGCTTA
GAAAACTGGGAGCTACAGTGGAAGAAGGTTCAGATTATTGTGTGATAACTCCGCCCAAAAA
GGTGAAAACGGCAGAGATTGATACATATGATGATCATAGAATGGCAATGGCATTCTCTCTT
GCAGCTTGTGCTGATGTTCCAATCACCATCAACGATCCTGGTTGCACCAGGAAAACCTTCC
CCGACTACTTCCAAGTACTTGAAAGAATCACAAAGCAC

The position of the C545T mutation is underlined.

Figure 7

ATGGCGCAAGTTAGCAGAATCTGCAATGGTGTGCAGAACCCATCTCTTATCTCCAATCTCT
CGAAATCCAGTCAACGCAAATCTCCCTTATCGGTTTCTCTGAAGACGCAGCAGCATCCACG
AGCTTATCCGATTTCGTCGTCGTGGGGATTGAAGAAGAGTGGGATGACGTTAATTGGCTCT
GAGCTTCGTCCTCTTAAGGTCATGTCTTCTGTTTCCACGGCGGAGAAAGCGTCGGAGATTG
TACTTCAACCCATTAGAGAAATCTCCGGTCTTATTAAGCTTCCTGGCTCCAAGTCTCTATCA
AATCGAATCCTGCTTCTCGCTGCTCTGTCTGAGGGAACAACTGTAGTGGACGACTTGTTGA
ATAGCGATGACATCAATTACATGCTTGATGCGTTGAAGAGATTGGGACTTAATGTGGAAAC
TGACAGTGAAAATAATCGTGCTGTAGTTGAAGGATGTGGCGGGATATTCCCAGCTTCCATA
GATTCAAAGAGTGATATCGAACTTTACCTCGGTAATGCAGGAACAGCAATGCGTCTACTTA
CCGCTGCGGTCACTGCTGCAGGTGGAAACGCAAGTTATGTGCTTGATGGGGTGCCTCGTA
TGAGAGAAAGACCTATAGGGGATTTGGTTGTTGGTCTTAAGCAGCTTGGTGCTGATGTTGA
ATGTACTCTTGGAACTAACTGCCCTCCTGTTCGTGTCAACGCTAATGGTGGCCTTCCCGGT
GGAAAGGTGAAGCTTTCTGGATCAATTAGTAGTCAGTACTTGACTGCTCTGCTCATGTCTG
CTCCCTTAGCTCTTGGAGACGTCGAGATTGAGATTGTCGATAAATTAATTTCTGTTCCATAT
GTTGAAATGACATTGAAGTTGATGGAACGTTTCGGGGTTAGTGTCGAGCATAGTGATAGCT
GGGATCGTTTCTTTGTCAAGGGCGGGCAAAAATACAAGTCTCCGGGTAATGCGTATGTAG
AAGGTGATGCTTCTAGTGCTAGTTATTTCTTGGCTGGTGCTGCCATTACCGGTGAAACTGT
CACAGTCGAAGGTTGTGGAACTACCAGCTTGCAGGGAGATGTAAAATTCGCCGAGGTCCT
TGAGAAAATGGGATGTAAAGTGTCCTGGACAGAGAACAGTGTGACTGTGACAGGACCACC
TAGAGATGCTTTTGGAATGAGACACTTGCGGGCTATTGATGTCAACATGAACAAAATGCCT
GATGTAGCCATGACCCTTGCCGTCGTTGCTCTCTTTGCTGACGGTCCAACCACCATTAGAG
ATGTGGCTAGCTGGAGAGTAAAGGAGACAGAAAGGATGATTGCCATTTGCACAGAGCTTA
GAAAACTGGGAGCTACAGTGGAAGAAGGTTCAGATTATTGTGTGATAACTCCGCCCAAAAA
GGTGAAAACGGCAGAGATTGATACATATGATGATCATAGAATGGCAATGGCATTCTCTCTT
GCAGCTTGTGCTGATGTTCCAATCACCATCAACGATCCTGGTTGCACCAGGAAAACCTTCC
CCGACTACTTCCAAGTACTTGAAAGAATCACAAAGCAC

Figure 8

ATGGCGCAAGTTAGCAGAATCTGCAATGGTGTGCAGAACCCATCTCTTATCTCCAATCTCT
CGAAATCCAGTCAACGCAAATCTCCCTTATCGGTTTCTCTGAAGACGCAGCAGCATCCACG
AGCTTATCCGATTTCGTCGTCGTGGGGATTGAAGAAGAGTGGGATGACGTTAATTGGCTCT
GAGCTTCGTCCTCTTAAGGTCATGTCTTCTGTTTCCACGGCGGAGAAAGCGTCGGAGATTG
TACTTCAACCCATTAGAGAAATCTCCGGTCTTATTAAGCTTCCTGGCTCCAAGTCTCTATCA
AATCGAATCCTGCTTCTCGCTGCTCTGTCTGAGGGAACAACTGTAGTGGACAACTTGTTGA
ATAGCGATGACATCAATTACATGCTTGATGCGTTGAAGAGATTGGGACTTAATGTGGAAAC
TGACAGTGAAAATAATCGTGCTGTAGTTGAAGGATGTGGCGGGATATTCCCAGCTTCCATA
GATTCAAAGAGTGATATCGAACTTTACCTCGGTAATGCAGGAACAGCAATGCGTCCACTTA
CCGCTGCGGTCACTGCTGCAGGTGGAAACGCAAGTTATGTGCTTGATGGGGTGCCTCGTA
TGAGAGAAAGACCTATAGGGGATTTGGTTGTTGGTCTTAAGCAGCTTGGTGCTGATGTTGA
ATGTACTCTTGGAACTAACTGCCTCCTGTTCGTGTCAACGCTAATGGTGGCCTTCCCGGT
GGAAAGGTGAAGCTTTCTGGATCAATTAGTA<u>A</u>TCAGTACTTGACTGCTCTGCTCATGTCTG
CTCCCTTAGCTCTTGGAGACGTCGAGATTGAGATTGTCGATAAATTAATTTCTGTTCCATAT
GTTGAAATGACATTGAAGTTGATGGAACGTTTCGGGGTTAGTGTCGAGCATAGTGATAGCT
GGGATCGTTTCTTTGTCAAGGGCGGGCAAAAATACAAGTCTCCGGGTAATGCGTATGTAG
AAGGTGATGCTTCTAGTGCTAGTTATTTCTTGGCTGGTGCTGCCATTACCGGTGAAACTGT
CACAGTCGAAGGTTGTGGAACTACCAGCTTGCAGGGAGATGTAAAATTCGCCGAGGTCCT
TGAGAAAATGGGATGTAAAGTGTCCTGGACAGAGAACAGTGTGACTGTGACAGGACCACC
TAGAGATGCTTTTGGAATGAGACACTTGCGGGCTATTGATGTCAACATGAACAAAATGCCT
GATGTAGCCATGACCCTTGCCGTCGTTGCTCTCTTTGCTGACGGTCCAACCACCATTAGAG
ATGTGGCTAGCTGGAGAGTAAAGGAGACAGAAAGGATGATTGCCATTTGCACAGAGCTTA
GAAAACTGGGAGCTACAGTGGAAGAAGGTTCAGATTATTGTGTGATAACTCCGCCCAAAAA
GGTGAAAACGGCAGAGATTGATACATATGATGATCATAGAATGGCAATGGCATTCTCTCTT
GCAGCTTGTGCTGATGTTCCAATCACCATCAACGATCCTGGTTGCACCAGGAAAACCTTCC
CCGACTACTTCCAAGTACTTGAAAGAATCACAAAGCAC

The G902A mutation is underlined.

Figure 9

ATGGCGCAAGTTAGCAGAATCTGCAATGGTGTGCAGAACCCATCTCTTATCTCCAATCTCT
CGAAATCCAGTCAACGCAAATCTCCCTTATCGGTTTCTCTGAAGACGCAGCAGCATCCACG
AGCTTATCCGATTTCGTCGTCGTGGGGATTGAAGAAGAGTGGGATGACGTTAATTGGCTCT
GAGCTTCGTCCTCTTAAGGTCATGTCTTCTGTTTCCACGGCGGAGAAAGCGTCGGAGATTG
TACTTCAACCCATTAGAGAAATCTCCGGTCTTATTAAGCTTCCTGGCTCCAAGTCTCTATCA
AATCGAATCCTGCTTCTCGCTGCTCTGTCTGAGGGAACAACTGTAGTGGACAACTTGTTGA
ATAGCGATGACATCAATTACATGCTTGATGCGTTGAAGAGATTGGGACTTAATGTGGAAAC
TGACAGTGAAAATAATCGTGCTGTAGTTGAAGGATGTGGCGGGATATTCCCAGCTTCCATA
GATTCAAAGAGTGATATCGAACTTTACCTCGGTAATGCAGGAACAGCAATGCGTCTACTTA
CCGCTGCGGTCACTGCTGCAGGTGGAAACGCAAGTTATGTGCTTGATGGGGTGCCTCGTA
TGAGAGAAAGACCTATAGGGGATTTGGTTGTTGGTCTTAAGCAGCTTGGTGCTGATGTTGA
ATGTACTCTTGGAACTAACTGCCCTCCTGTTCGTGTCAACGCTAATGGTGGCCTTCCCGGT
GGAAAGGTGAAGCTTTCTGGATCAATTAGTAATCAGTACTTGACTGCTCTGCTCATGTCTG
CTCCCTTAGCTCTTGGAGACGTCGAGATTGAGATTGTCGATAAATTAATTTCTGTTCCATAT
GTTGAAATGACATTGAAGTTGATGGAACGTTTCGGGGTTAGTGTCGAGCATAGTGATAGCT
GGGATCGTTTCTTTGTCAAGGGCGGGCAAAAATACAAGTCTCCGGGTAATGCGTATGTAG
AAGGTGATGCTTCTAGTGCTAGTTATTTCTTGGCTGGTGCTGCCATTACCGGTGAAACTGT
CACAGTCGAAGGTTGTGGAACTACCAGCTTGCAGGGAGATGTAAAATTCGCCGAGGTCCT
TGAGAAAATGGGATGTAAAGTGTCCTGGACAGAGAACAGTGTGACTGTGACAGGACCACC
TAGAGATGCTTTTGGAATGAGACACTTGCGGGCTATTGATGTCAACATGAACAAAATGCCT
GATGTAGCCATGACCCTTGCCGTCGTTGCTCTCTTTGCTGACGGTCCAACCACCATTAGAG
ATGTGGCTAGCTGGAGAGTAAAGGAGACAGAAAGGATGATTGCCATTTGCACAGAGCTTA
GAAAACTGGGAGCTACAGTGGAAGAAGGTTCAGATTATTGTGTGATAACTCCGCCCAAAAA
GGTGAAAACGGCAGAGATTGATACATATGATGATCATAGAATGGCAATGGCATTCTCTCTT
GCAGCTTGTGCTGATGTTCCAATCACCATCAACGATCCTGGTTGCACCAGGAAAACCTTCC
CCGACTACTTCCAAGTACTTGAAAGAATCACAAAGCAC

Figure 10

ATGGCGCAAGTTAGCAGAATCTGCAATGGTGTGCAGAACCCATCTCTTATCTCCAATCTCT
CGAAATCCAGTCAACGCAAATCTCCCTTATCGGTTTCTCTGAAGACGCAGCAGCATCCACG
AGCTTATCCGATTTCGTCGTCGTGGGGATTGAAGAAGAGTGGGATGACGTTAATTGGCTCT
GAGCTTCGTCCTCTTAAGGTCATGTCTTCTGTTTCCACGGCGGAGAAAGCGTCGGAGATTG
TACTTCAACCCATTAGAGAAATCTCCGGTCTTATTAAGCTTCCTGGCTCCAAGTCTCTATCA
AATCGAATCCTGCTTCTCGCTGCTCTGTCTGAGGGAACAACTGTAGTGGACGACTTGTTGA
ATAGCGATGACATCAATTACATGCTTGATGCGTTGAAGAGATTGGGACTTAATGTGGAAAC
TGACAGTGAAAATAATCGTGCTGTAGTTGAAGGATGTGGCGGGATATTCCCAGCTTCCATA
GATTCAAAGAGTGATATCGAACTTTACCTCGGTAATGCAGGAACAGCAATGCGTCCACTTA
CCGCTGCGGTCACTGCTGCAGGTGGAAACGCAAGTTATGTGCTTGATGGGGTGCCTCGTA
TGAGAGAAAGACCTATAGGGGATTTGGTTGTTGGTCTTAAGCAGCTTGGTGCTGATGTTGA
ATGTACTCTTGGAACTAACTGCCCTCCTGTTCGTGTCAACGCTAATGGTGGCCTTCCCGGT
GGAAAGGTGAAGCTTTCTGGATCAATTAGTAATCAGTACTTGACTGCTCTGCTCATGTCTG
CTCCCTTAGCTCTTGGAGACGTCGAGATTGAGATTGTCGATAAATTAATTTCTGTTCCATAT
GTTGAAATGACATTGAAGTTGATGGAACGTTTCGGGGTTAGTGTCGAGCATAGTGATAGCT
GGGATCGTTTCTTTGTCAAGGGCGGGCAAAAATACAAGTCTCCGGGTAATGCGTATGTAG
AAGGTGATGCTTCTAGTGCTAGTTATTTCTTGGCTGGTGCTGCCATTACCGGTGAAACTGT
CACAGTCGAAGGTTGTGGAACTACCAGCTTGCAGGGAGATGTAAAATTCGCCGAGGTCCT
TGAGAAAATGGGATGTAAAGTGTCCTGGACAGAGAACAGTGTGACTGTGACAGGACCACC
TAGAGATGCTTTTGGAATGAGACACTTGCGGGCTATTGATGTCAACATGAACAAAATGCCT
GATGTAGCCATGACCCTTGCCGTCGTTGCTCTCTTTGCTGACGGTCCAACCACCATTAGAG
ATGTGGCTAGCTGGAGAGTAAAGGAGACAGAAAGGATGATTGCCATTTGCACAGAGCTTA
GAAAACTGGGAGCTACAGTGGAAGAAGGTTCAGATTATTGTGTGATAACTCCGCCCAAAAA
GGTGAAAACGGCAGAGATTGATACATATGATGATCATAGAATGGCAATGGCATTCTCTCTT
GCAGCTTGTGCTGATGTTCCAATCACCATCAACGATCCTGGTTGCACCAGGAAAACCTTCC
CCGACTACTTCCAAGTACTTGAAAGAATCACAAAGCAC

Figure 11

ATGGCGCAAGTTAGCAGAATCTGCAATGGTGTGCAGAACCCATCTCTTATCTCCAATCTCT
CGAAATCCAGTCAACGCAAATCTCCCTTATCGGTTTCTCTGAAGACGCAGCAGCATCCACG
AGCTTATCCGATTTCGTCGTCGTGGGGATTGAAGAAGAGTGGGATGACGTTAATTGGCTCT
GAGCTTCGTCCTCTTAAGGTCATGTCTTCTGTTTCCACGGCGGAGAAAGCGTCGGAGATTG
TACTTCAACCCATTAGAGAAATCTCCGGTCTTATTAAGCTTCCTGGCTCCAAGTCTCTATCA
AATCGAATCCTGCTTCTCGCTGCTCTGTCTGAGGGAACAACTGTAGTGGACAACTTGTTGA
ATAGCGATGACATCAATTACATGCTTGATGCGTTGAAGAGATTGGGACTTAATGTGGAAAC
TGACAGTGAAAATAATCGTGCTGTAGTTGAAGGATGTGGCGGGATATTCCCAGCTTCCATA
GATTCAAAGAGTGATATCGAACTTTACCTCGGTAATGCAGCAACAGCAATGCGTCCACTTA
CCGCTGCGGTCACTGCTGCAGGTGGAAACGCAAGTTATGTGCTTGATGGGGTGCCTCGTA
TGAGAGAAAGACCTATAGGGGATTTGGTTGTTGGTCTTAAGCAGCTTGGTGCTGATGTTGA
ATGTACTCTTGGAACTAACTGCCCTCCTGTTCGTGTCAACGCTAATGGTGGCCTTCCCGGT
GGAAAGGTGAAGCTTTCTGGATCAATTAGTAGTCAGTACTTGACTGCTCTGCTCATGTCTG
CTCCCTTAGCTCTTGGAGACGTCGAGATTGAGATTGTCGATAAATTAATTTCTGTTCCATAT
GTTGAAATGACATTGAAGTTGATGGAACGTTTCGGGGTTAGTGTCGAGCATAGTGATAGCT
GGGATCGTTTCTTTGTCAAGGGCGGGCAAAAATACAAGTCTCCGGGTAATGCGTATGTAG
AAGGTGATGCTTCTAGTGCTAGTTATTTCTTGGCTGGTGCTGCCATTACCGGTGAAACTGT
CACAGTCGAAGGTTGTGGAACTACCAGCTTGCAGGGAGATGTAAAATTCGCCGAGGTCCT
TGAGAAAATGGGATGTAAAGTGTCCTGGACAGAGAACAGTGTGACTGTGACAGGACCACC
TAGAGATGCTTTTGGAATGAGACACTTGCGGGCTATTGATGTCAACATGAACAAAATGCCT
GATGTAGCCATGACCCTTGCCGTCGTTGCTCTCTTTGCTGACGGTCCAACCACCATTAGAG
ATGTGGCTAGCTGGAGAGTAAAGGAGACAGAAAGGATGATTGCCATTTGCACAGAGCTTA
GAAAACTGGGAGCTACAGTGGAAGAAGGTTCAGATTATTGTGTGATAACTCCGCCCAAAAA
GGTGAAAACGGCAGAGATTGATACATATGATGATCATAGAATGGCAATGGCATTCTCTCTT
GCAGCTTGTGCTGATGTTCCAATCACCATCAACGATCCTGGTTGCACCAGGAAAACCTTCC
CCGACTACTTCCAAGTACTTGAAAGAATCACAAAGCAC

The G530C mutation is underlined.

Figure 12

ATGGCGCAAGTTAGCAGAATCTGCAATGGTGTGCAGAACCCATCTCTTATCTCCAATCTCT
CGAAATCCAGTCAACGCAAATCTCCCTTATCGGTTTCTCTGAAGACGCAGCAGCATCCACG
AGCTTATCCGATTTCGTCGTCGTGGGGATTGAAGAAGAGTGGGATGACGTTAATTGGCTCT
GAGCTTCGTCCTCTTAAGGTCATGTCTTCTGTTTCCACGGCGGAGAAAGCGTCGGAGATTG
TACTTCAACCCATTAGAGAAATCTCCGGTCTTATTAAGCTTCCTGGCTCCAAGTCTCTATCA
AATCGAATCCTGCTTCTCGCTGCTCTGTCTGAGGGAACAACTGTAGTGGACGACTTGTTGA
ATAGCGATGACATCAATTACATGCTTGATGCGTTGAAGAGATTGGGACTTAATGTGGAAAC
TGACAGTGAAAATAATCGTGCTGTAGTTGAAGGATGTGGCGGGATATTCCCAGCTTCCATA
GATTCAAAGAGTGATATCGAACTTTACCTCGGTAATGCAGCAACAGCAATGCGTCCACTTA
CCGCTGCGGTCACTGCTGCAGGTGGAAACGCAAGTTATGTGCTTGATGGGGTGCCTCGTA
TGAGAGAAAGACCTATAGGGGATTTGGTTGTTGGTCTTAAGCAGCTTGGTGCTGATGTTGA
ATGTACTCTTGGAACTAACTGCCCTCCTGTTCGTGTCAACGCTAATGGTGGCCTTCCCGGT
GGAAAGGTGAAGCTTCTGGATCAATTAGTAGTCAGTACTTGACTGCTCTGCTCATGTCTG
CTCCCTTAGCTCTTGGAGACGTCGAGATTGAGATTGTCGATAAATTAATTTCTGTTCCATAT
GTTGAAATGACATTGAAGTTGATGGAACGTTTCGGGGTTAGTGTCGAGCATAGTGATAGCT
GGGATCGTTTCTTTGTCAAGGGCGGGCAAAAATACAAGTCTCCGGGTAATGCGTATGTAG
AAGGTGATGCTTCTAGTGCTAGTTATTTCTTGGCTGGTGCTGCCATTACCGGTGAAACTGT
CACAGTCGAAGGTTGTGGAACTACCAGCTTGCAGGGAGATGTAAAATTCGCCGAGGTCCT
TGAGAAAATGGGATGTAAAGTGTCCTGGACAGAGAACAGTGTGACTGTGACAGGACCACC
TAGAGATGCTTTTGGAATGAGACACTTGCGGGCTATTGATGTCAACATGAACAAAATGCCT
GATGTAGCCATGACCCTTGCCGTCGTTGCTCTCTTTGCTGACGGTCCAACCACCATTAGAG
ATGTGGCTAGCTGGAGAGTAAAGGAGACAGAAGGATGATTGCCATTTGCACAGAGCTTA
GAAAACTGGGAGCTACAGTGGAAGAAGGTTCAGATTATTGTGTGATAACTCCGCCCAAAAA
GGTGAAAACGGCAGAGATTGATACATATGATGATCATAGAATGGCAATGGCATTCTCTCTT
GCAGCTTGTGCTGATGTTCCAATCACCATCAACGATCCTGGTTGCACCAGGAAAACCTTCC
CCGACTACTTCCAAGTACTTGAAAGAATCACAAAGCAC

Figure 13

```
   1 ATGGCACAGA TTAGCAAAAT GACACAGGGG ATACAAACCC TTTATCCCAA TTCCAAGATT
  61 CATAAACCCC AAGTTCCCAC ATTTCTCCCT TCACTTCCTT TTGGATCTAA AAACCTGAAA
 121 AAATCAGTAA AATGTTTGTG GGTTTTGAAT AAAGATTCAG TTTTGACAAC AAGGTCTTGT
 181 TCTTCTTCTT TTAGGATTTC AGCATCAGTG CTACAACCC AGAAACCTTC TGAGATTGTG
 241 CTGCAACCCA TCAAAGAAAT ATCAGGCACT GTCAAATTGC CAGGCTCTAA ATCTCTATCC
 301 AATCGTATCC TCCTTCTGGC TGCTCTATCT GAAGGAACAA CTGTGGTTGA CAATTTGCTA
 361 AGTAGTGATG ATATTCATTA CATGCTTGGT GCGTTGAAAA CACTTGGACT GCAAGTAGAA
 421 GATGACAGTG GAAACCAACA AGCTGTTGTT GAAGGTTGTG GTGGTTTGTT CCCTGCCGCT
 481 AAAGAGTCCA AGGAAGAGAT TCAACTTTTC CTTGGAAATG CAGGAACTGC AATGCGGCCA
 541 CTAACAGCAG CAGTTGCTGT AGCTGGCGGA AATTCAAGGT ATGTACTTGA TGGAGTTCCT
 601 CGAATGAGAG AGAGACCAAT TAGTGATTTG GTTGATGGTC TTAAGCAGCT TGGTGCAGAG
 661 GTTGATTGTT TCCTTGGTAC GAAATGCCT CCTGTTCGAA TTGTCAGCAA GGGAGGTCTC
 721 CCAGGAGGGA AGGTGAAGCT GTCTGGATCC ATTAGCAGCC AATACTTGAC TGCTCTGCTT
 781 ATGGCTGCTC CACTGGCTTT AGGAGATGTG GAGATTGAAA TCATTGACAA ACTAATATCT
 841 GTACCTTATG TCGAAATGAC TTTGAAGTTG ATGGAGCGAT TTGGTATATC TGTGGAGCAC
 901 AATAGTAGCT GGGACAGGTT CTTTGTCCGA GGAGGTCAGA AATACAAGTC TCCTGGAAAA
 961 GCTTATGTGG AAGGTGATGC TTCAAGTGCT AGTTACTTCT TGGCTGGTGC AGCTGTCACA
1021 GGTGGAACCA TCACTGTTGA AGGTTGTGGA ACAAACAGTT TACAGGGGGA TGTCAAATTT
1081 GCTGAGGTTC TTGAGAAAAT GGGAGCAGAA GTTACATGGA CAGAGAATAG CGTCACAGTT
1141 AAAGGACCTC CAAGGAATTC TTCTGGAAGG AAGCATTTGC ATGCCATTGA TGTGAACATG
1201 AATAAAATGC CTGATGTCGC CATGACACTT GCTGTAGTTG CACTTTTTGC TGACGGTCCC
1261 ACTGCTATAA GAGACGTTGC TAGTTGGAGA GTCAAGGAAA CTGAGCGCAT GATCGCCATA
1321 TGCACAGAAC TTAGGAAGTT GGGAGCAACT GTTGAAGAAG GACCTGACTA CTGCATAATC
1381 ACCCCACCGG AGAAATTAAA TGTGACCGAA ATTGATACAT ATGACGATCA CAGGATGGCC
1441 ATGGCCTTTT CTCTTGCTGC TTGTGCAGAT GTTCCAGTCA CCATCAATGA CCCTGGCTGC
1501 ACGCGGAAAA CCTTCCCAAA CTACTTTGAT GTCCTTCAGC AGTACTCCAA GCATTGA
```

Figure 14

```
   1 GATTAGTAGC ATGGCACAAG GGATACAGAC CCTTAGTCTG AATTCCTCCA ATCTTTCTAA
  61 AACACAAAAG GGTCCTCTTG TTTCAAATTC TCTCTTCTTT GGATCAAAGA AAGTAACCCA
 121 AATTTCAGCA AAATCATTAG GGGTGTTTAA GAAAGATTCA GTTTTGAGGG TGGTGAGGAA
 181 GTCATCTTTT AGGATTTCTG CATCAGTGGC TACTGCAGAG AAACCCCATG AGATTGTGCT
 241 AGAACCCATC AAAGATATAT CTGGTACTGT TAAATTACCC GGTTCGAAAT CCCTTTCCAA
 301 TCGTATTCTC CTTCTTGCTG CCCTTTCTGA GGGAAGGACT GTTGTTGACA ATTTACTGAG
 361 TAGTGACGAC ATTCATTACA TGCTTGGTGC GTTGAAAACA CTTGGACTTC ATGTTGAAGA
 421 TGACAATGAA AACCAACGAG CAATTGTGGA AGGTTGTGGT GGGCAGTTTC CTGTCGGTAA
 481 AAAGTCTGAG GAAGAAATCC AACTATTCCT TGGAAATGCA GGAACAGCAA TGCGTCCGTT
 541 GACAGCAGCA GTTACTGTAG CTGGAGGACA TTCAAGATAT GTTCTTGATG GAGTTCCTAG
 601 GATGAGAGAG AGACCAATTG GTGATTTGGT TGATGGTCTT AAGCAGCTTG GCGCAGAGGT
 661 AGATTGTTCC CTTGGTACGA ATTGTCCCCC AGTTCGAATT GTCAGCAAGG GAGGTCTTCC
 721 AGGAGGGAAG GTAAAGCTCT CTGGATCCAT CAGCAGCCAA TACCTGACTG CTCTGCTTAT
 781 GGCTGCTCCC CTGGCTCTAG AGATGTGGA GATTGAAATA ATTGACAAAC TGATATCTGT
 841 GCCTTATGTT GAAATGACAC TGAAGTTGAT GGAGCGATTT GGTGTCTTTG TGGAGCACAG
 901 TAGTGGCTGG GACAGATTCT TGGTAAAAGG AGGTCAGAAG TACAAATCTC CTGGGAAAGC
 961 ATTTGTTGAA GGAGATGCCT CAAGTGCTAG CTATTTTTTG GCGGGGGCAG CAGTCACAGG
1021 TGGAACCGTC ACTGTTGAAG GTTGTGGAAC AAGCAGTTTA CAGGGAGATG TTAAGTTCGC
1081 TGAGGTCCTC GAGAAGATGG GGGCAGAAGT TACATGGACA GAGAACAGTG TCACAGTTAA
1141 AGGACCTCCG AGGAACTCTT CTGGAATGAA ACATTTGCGT GCCATTGACG TGAACATGAA
1201 CAAAATGCCA GATGTGGCCA TGACTCTTGC CGTAGTTGCA CTTTTTGCTG ATGGTCCTAC
1261 TACCATAAGA GACGTTGCTA GCTGGAGAGT AAAGGAAACT GAGCGGATGA TTGCCATATG
1321 CACCGAACTT AGGAAGTTGG GTGCAACAGT TGTTGAAGGG TCAGACTACT GCATAATCAC
1381 CCCACCAGAA AAGTTAAACG TAACGGAGAT TGATACATAT GATGACCACA GAATGGCTAT
1441 GGCTTTCTCT CTTGCTGCTT GTGCTGATGT TCCAGTCACT ATTAAGGACC CTGGCTGTAC
1501 TCGCAAAACC TTCCCCGACT ACTTCGAGGT TCT
```

Figure 15

1 MAQISKMTQG IQTLYPNSKI HKPQVPTFLP SLPFGSKNLK KSVKCLWVLN KDSVLTTRSC
61 SSSFRISASV ATTQKPSEIV LQPIKEISGT VKLPGSKSLS NRILLLAALS EGTTVVDNLL
121 SSDDIHYMLG ALKTLGLQVE DDSGNQQAVV EGCGGLFPAA KESKEEIQLF LGNAGTAMRP
181 LTAAVAVAGG NSRYVLDGVP RMRERPISDL VDGLKQLGAE VDCFLGTKCP PVRIVSKGGL
241 PGGKVKLSGS ISSQYLTALL MAAPLALGDV EIEIIDKLIS VPYVEMTLKL MERFGISVEH
301 NSSWDRFFVR GGQKYKSPGK AYVEGDASSA SYFLAGAAVT GGTITVEGCG TNSLQGDVKF
361 AEVLEKMGAE VTWTENSVTV KGPPRNSSGR KHLHAIDVNM NKMPDVAMTL AVVALFADGP
421 TAIRDVASWR VKETERMIAI CTELRKLGAT VEEGPDYCII TPPEKLNVTE IDTYDDHRMA
481 MAFSLAACAD VPVTINDPGC TRKTFPNYFD VLQQYSKH

Figure 16

```
  1 MAQISSMAQG IQTLSLNSSN LSKTQKGPLV SNSLFFGSKK VTQISAKSLG VFKKDSVLRV
 61 VRKSSFRISA SVATAEKPHE IVLEPIKDIS GTVKLPGSKS LSNRILLLAA LSEGRTVVDN
121 LLSSDDIHYM LGALKTLGLH VEDDNENQRA IVEGCGGQFP VGKKSEEEIQ LFLGNAGTAM
181 RPLTAAVTVA GGHSRYVLDG VPRMRERPIG DLVDGLKQLG AEVDCSLGTN CPPVRIVSKG
241 GLPGGKVKLS GSISSQYLTA LLMAAPLALG DVEIEIIDKL ISVPYVEMTL KLMERFGVFV
301 EHSSGWDRFL VKGGQKYKSP GKAFVEGDAS SASYFLAGAA VTGGTVTVEG CGTSSLQGDV
361 KFAEVLEKMG AEVTWTENSV TVKGPPRNSS GMKHLRAIDV NMNKMPDVAM TLAVVALFAD
421 GPTTIRDVAS WRVKETERMI AICTELRKLG ATVVEGSDYC IITPPEKLNV TEIDTYDDHR
481 MAMAFSLAAC ADVPVTIKDP GCTRKTFPDY FEVLQKYSKH
```

Figure 17

```
  1 mesitlqpia rvdgtinlpg sksvsnrall laalahgktv ltnlldsddv rhmlnaltgl
 61 gvsytlsadr trceiigngg plhaegalel flgnagtamr plaaalclgs ndivltgepr
121 mkerpighlv dairlggaki tyleqenypp lrlqggftgg nvdvdgsvss qfltallmta
181 plapedtvir ikgdlvskpy iditlnlmkt fgveienqhy qqfvvkggqs yqspgtylve
241 gdassasyfl aaaaikggtv kvtgigmsm qgdirfadvl ekmgaticwg ddyisctrge
301 lnaidmdmnh ipdaamtlat aalfakgttt lmiynwrvk etdrlfamat elrkvgaeve
361 eghdyiritp pekinfaeia tyndhrmamc fslvalsdtp vtildpkcta ktfpdyfeql
421 arisqaa
```

Figure 18

```
  1 MATQVGKIYN GTQKTCVLPN VSKTQNPKHV PFVSFKSNLN GKTSSWGLVV KNNGKFGSIK
 61 ARSLKVSAST ATAEKPSRAS EIVLQPINEI SGTVKLPGSK SLSNRILLLA ALSEGTTVVE
121 NLLNSDDVHH MLVALGKLGL YVKHDSEKKQ AIVEGCGGQF PVGKGEGQEI ELFLGNAGTA
181 MRPLTAAITA AGGNSSYVLD GVPRMRERPI GDLVTGLKQL GADVDCILGT NCPPVRIEGK
241 GGLPGGKVKL SGSISSQYLT ALLMAAPLAL GDVEIEIIDK LISIPYVEMT MKLMERFGVT
301 VEHTDSWDRF FIRGGQKYMS PGNAYVEGDA SSASYFLAGA AVTGGTVTVE GCGTSSLQGD
361 VKFAEVLEMM GAKVTWTENS VTVTGPPRNS SGRKHLRAID VNMNKMPDVA MTLAVVALYA
421 DGPTAIRDVA SWRVKETERM IAICTELRKL GATVEEGPDY CVITPPEKLN VTAIDTYDDH
481 RMAMAFSLAA CAEVPVTIKD PGCTRKTFPD YFEVLDRVTK H*
```

Figure 19

```
  1 MAGAEEIVLQ PIKEISGTVK LPGSKSLSNR ILLLAALSEG TTVVDNLLNS EDVHYMLGAL
 61 RTLGLSVEAD KAAKRAVVVG CGGKFPVEDA KEEVQLFLGN AGTAMRPLTA AVTAAGGNAT
121 YVLDGVPRMR ERPIGDLVVG LKQLGADVDC FLGTDCPPVR VNGIGGLPGG KVKLSGSISS
181 QYLSALLMAA PLALGDVEIE IIDKLISIPY VEMTLRLMER FGVKAEHSDS WDRFYIKGGQ
241 KYKSPKNAYV EGDASSASYF LAGAAITGGT VTVEGCGTTS LQGDVKFAEV LEMMGAKVTW
301 TETSVTVTGP PREPFGRKHL KAIDVNMNKM PDVAMTLAVV ALFADGPTAI RDVASWRVKE
361 TERMVAIRTE LTKLGASVEE GPDYCIITPP EKLNVTAIDT YDDHRMAMAF SLAACAEVPV
421 TIRDPGCTRK TFPDYFDVLS TFVKN
```

Figure 20

```
  1 MAATMASNAA AAAAVSLDQA VAASAAFSSR KQLRLPAAAR GGMRVRVRAR GRREAVVVAS
 61 ASSSSVAAPA AKAEEIVLQP IREISGAVQL PGSKSLSNRI LLLSALSEGT TVVDNLLNSE
121 DVHYMLEALK ALGLSVEADK VAKRAVVVGC GGKFPVEKDA KEEVQLFLGN AGTAMRPLTA
181 AVTAAGGNAT YVLDGVPRMR ERPIGDLVVG LKQLGADVDC FLGTECPPVR VKGIGGLPGG
241 KVKLSGSISS QYLSALLMAA PLALGDVEIE IIDKLISIPY VEMTLRLMER FGVKAEHSDS
301 WDRFYIKGGQ KYKSPGNAYV EGDASSASYF LAGAAITGGT VTVQGCGTTS LQGDVKFAEV
361 LEMMGAKVTW TDTSVTVTGP PREPYGKKHL KAVDVNMNKM PDVAMTLAVV ALFADGPTAI
421 RDVASWRVKE TERMVAIRTE LTKLGASVEE GPDYCITPP EKLNITAIDT YDDHRMAMAF
481 SLAACADVPV TIRDPGCTRK TFPNYFDVLS TFVRN
```

Figure 21

```
  1 MAMAAAATMA ASASSSAVSL DRAAPAPSRR LPMPAARPAR RGAVRLWGPR GAAARATSVA
 61 APAAPSGAEE VVLQPIREIS GAVQLPGSKS LSNRILLLSA LSEGTTVVDN LLNSEDVHYM
121 LEALEALGLS VEADKVAKRA VVVGCGGRFP VEKDAQEEVK LFLGNAGTAM RPLTAAVVAA
181 GGNATYVLDG VPRMRERPIG DLVVGLQQLG ADADCFLGTN CPPVRINGKG GLPGGKVKLS
241 GSISSQYLSS LLMAAPLALE DVEIEIIDKL ISVPYVEMTL KLMERFGVTA EHSDSWDRFY
301 IKGGQKYKSP GNAYVEGDAS SASYFLAGAA ITGGTVTVEG CGTTSLQGDV KFAEVLEMMG
361 AKVTWTDTSV TVTGPPRQPF GRKHLKAVDV NMNKMPDVAM TLAVVALFAD GPTAIRDVAS
421 WRVKETERMV AIRTELTKLG ATVEEGPDYC IITPPEKLNI TAIDTYDDHR MAMAFSLAAC
481 AEVPVTIRDP GCTRKTFPNY FDVLSTFVKN
```

Figure 22

```
  1 MAIHINNISN FTSNLTNTHN PNSSSKSSPS SFLSFGSNFN NPMMNLASVS CKQNDQKRSP
 61 AVAASVATTQ KTSTAPEEIV LKPIKEISGT VNLPGSKSLS NRILLAALA  EGTTVVENLL
121 NSDDVHYMLG ALRALGLNVE ENGEIKRATV EGCGGVFPVG KEAKDEIQLF LGNAGTAMRP
181 LTAAVTAAGG NSSYILDGVP RMRERPIGDL V
```

GLYPHOSATE RESISTANCE ENHANCEMENT

CROSS REFERENCE TO RELATED APPLICATIONS

This application is a continuation of application Ser. No. 14/114,599, filed Dec. 3, 2013, which is a national stage filing under 35 U.S.C. §371 of International Application No. PCT/NL2012/050290, filed on Apr. 27, 2012, which claims the benefit of priority of U.S. Provisional Application No. 61/480,623, filed on Apr. 29, 2011. All of these applications are incorporated herein by reference in their entirety.

FIELD OF THE INVENTION

The present invention relates to a new method for providing a glyphosate resistant plant and/or enhancing glyphosate resistance of a plant. The method encompasses providing to a plant a nucleotide sequence that encodes an EPSPS enzyme comprising (a) specific mutation(s). In comparison to an unmodified plant, the plant obtained by the method displays (improved) glyphosate resistance. Also provided are a (transgenic) plant including a seed thereof and plant products that can be obtained by the method according to the invention.

DESCRIPTION OF THE BACKGROUND ART

Glyphosate (N-phosphonomethyl-glycine) is the active compound in Round Up, the most commonly used herbicide, it is used in agriculture, horticulture, and silviculture. Typically it is sprayed and absorbed through the leaves.

Glyphosate acts broadly against plant species and works via inhibition of the enzyme 5-enolpyruvylshikimate-3-phosphate synthase (EPSPS) which is a key enzyme in the shikimate pathway, essential for the production of aromatic amino acids. Glyphosate has a chemical structure similar to phosphoenolpyruvate (PEP), the natural EPSPS enzyme substrate, and thus competes with PEP for the enzyme active site. Inhibition of EPSPS disrupts amino acid synthesis and thereby kills the affected plant cells. Glyphosate is non-selective and it kills both weeds and crop plants.

The popularity of glyphosate as a herbicide is partly due to its low toxicity to animals. The shikimate pathway is only found in plants and bacteria. Monsanto originally patented glyphosate in the 1970s.

The observation that certain bacterial types were able to survive in glyphosate led to the discovery that some bacterial EPSPS enzymes are insensitive to glyphosate. This led to the development of Monsanto's transgenic Round Up Ready crops which express these glyphosate resistant bacterial EPSPS enzymes.

Current Roundup Ready crops include soybean, maize (corn), sorghum, canola, alfalfa, cotton and sugar beet. These crops greatly improved farmers' ability to control weeds, since glyphosate can be sprayed on fields without severely affecting the crops. As of 2005, 87% of USA soybean fields were planted with glyphosate-resistant crops (National Agriculture Statistics Service (2005) in Acreage eds. Johanns, M. & Wyatt, S. D. 6 30, (U.S. Dept, of Agriculture, Washington, D.C.)).

It is however found that Roundup Ready soybean crops, compared with the top conventional varieties, have a 6.7% lower yield (Charles Benbrook. Evidence of the Magnitude and Consequences of the Roundup Ready Soybean Yield Drag from University-Based Varietal Trials in 1998. Ag BioTech InfoNet Technical Paper Number 1). Conferring glyphosate resistance to a plant may involve significant fitness cost of said plant. Such fitness cost may, next to a decreased crop yield, also be expressed by decreased biomass accumulation over time.

An important mutation that has been found to give plants glyphosate resistance under field conditions is a single nucleotide change, altering the proline at position 106 in the EPSPS enzyme into a leucine (P106L). Many weed species around the world have independently developed this mutation but thus far other spontaneous mutations in EPSPS have not been found (Beerson of al. Plant Physiol, July 2002, Vol. 129, pp, 1265-1275 2002). Gassert et al. (J. Biol. Chem Vol 263(9) pp 4280-4289) describe structure, expression, and evolution of the 5-Enolpyruvylshikimate-3-phosphate Synthase Genes of *Petunia* and Tomato.

There is a need to identify further mutations that are useful in providing EPSPS enzymes that provide (improved) resistance to glyphosate, and plants carrying such mutation(s) and/or expressing such enzymes, that are thereby able to grow in the presence of (increased levels of) glyphosate. Such plants may be able to grow in the presence of higher concentrations of glyphosate in comparison with prior art plants, including glyphosate resistant plants, or show enhanced growth in the presence of similar concentrations of glyphosate in comparison with prior art plants, including glyphosate resistant plants.

Furthermore, there is also a need to identify mutations that further enhance glyphosate resistance of prior art glyphosate resistant plants or mutations that preferably reduce the fitness cost associated with the glyphosate resistance of said prior art glyphosate resistant plants.

It is an object of the present invention to provide for at least one of the above-mentioned needs.

DESCRIPTION OF THE INVENTION

Definitions

In the following description and examples, a number of terms are used, in order to provide a clear and consistent understanding of the specification and claims, including the scope to be given such terms, the following definitions are providedUnless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

As used herein, the singular forms "a," "an" and "the" include plural referents unless the context clearly dictates otherwise. For example, a method for isolating "a" DNA molecule, as used above, includes isolating a plurality of molecules (e.g. 10's, 100's, 1000's, 10's of thousands, 100's of thousands, millions, or more molecules).

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references Sambrook et al., Molecular Cloning. A Laboratory Manual, 2nd Edition, Cold Spring Harbor Laboratory Press, Cold Spring Harbor, N.Y., 1989; Ausubei et al., Current Protocols in Molecular Biology, John Wiley & Sons, New York, 1987 and periodic updates; and the series Methods in Enzymology, Academic Press, San Diego.

"Cultivated plant" and "wild plant" refers, respectively, to plants which have been bred for good agronomic characteristics by humans and plants which are found in nature in the wild. Genes and alleles found in the latter are also referred to as "wild type". However, with respect to the EPSPS genes, genes present both in "cultivated plant" and "wild type plants" are referred to as "wild-type genes". Expression of such wild-type genes in the plant to levels normally found in these plants does not provide for "glyphosate-resistant" EPSPS, but for "glyphosate-sensitive" EPSPS (see below).

A "nucleic acid construct" or "vector" is herein understood to mean a man-made nucleic acid molecule resulting from the use of recombinant DNA technology and which is used to deliver exogenous DNA into a host cell. The vector backbone may for example be a binary or superbinary vector (see e.g. U.S. Pat. No. 5,591,616, US 2002138879 and WO95/06722), a co-integrate vector or a T-DNA vector, as known in the art and as described elsewhere herein, into which a chimeric gene is integrated or, if a suitable transcription regulatory sequence is already present, only a desired nucleic acid sequence (e.g. a coding sequence, an antisense or an inverted repeat sequence) is integrated downstream of the transcription regulatory sequence. Vectors usually comprise further genetic elements to facilitate their use in molecular cloning, such as e.g. selectable markers, multiple cloning sites and the like.

As used herein, a "glyphosate-resistant" EPSPS refers to an EPSPS, the expression of which in a plant cell confers glyphosate resistance upon the plant cell. An EPSPS is "glyphosate-sensitive" if it does not confer glyphosate-resistance when being expressed in plant cells at levels normally found in such plants, i.e. when not brought to over-expression.

As used herein, a "glyphosate-resistant" cell or plant refers to a cell or plant that can survive or continue to grow in the presence of certain concentrations of glyphosate that typically kill or inhibit the growth of other cells or plants Growth includes, for instance, photosynthesis, increase of rooting, increase of height, increase of mass, or development of new leaves.

For example, an EPSPS is glyphosate resistant when it confers glyphosate resistance to a plant. E.g. at the same level of expression of EPSPS, a plant carrying the glyphosate resistant EPSPS continues to survive or grow at levels of glyphosate at least 5%, 10%, 20%, 30%, or 40% higher than the level at which a plant not carrying the glyphosate resistant EPSPS stops growth or dies.

In one embodiment, a glyphosate-resistant (plant) cell can grow and divide on a culture medium containing 50 µM (or 50 mg/l) or more glyphosate, preferably a glyphosate-resistant cell can grow and divide on a culture medium containing 100 µM (or 100 mg/l) or more glyphosate, such as 200 µM (or 200 mg/l), 300 µM (or 300 mg/l) or 400 µM (or 400 mg/l) glyphosate. Even more preferably a glyphosate-resistant cell can grow and divide on a culture medium containing 500 µM (or 500 mg/l) or more glyphosate, such as 600 µM (or 600 mg/l). For purposes of the present invention, the term "glyphosate" includes any herbicidal effective form of N-phosphonomethylglycine (including any salt thereof) and other forms which result in the production of the glyphosate anion in plants.

Glyphosate resistance", as defined in the current application, is in the field also commonly referred to as glyphosate tolerance.

"Functional", in relation to proteins (or variants, such as orthologs or mutants, and fragments), refers to the capability of the gene and/or encoded protein to modify the (quantitative and/or qualitative) characteristic by modifying the expression level of the gene (e.g. by overexpression or silencing) in a plant. For example, the functionality of a putative protein obtained from plant species X can be tested by various methods. Preferably, if the protein is functional, silencing of the gene encoding the protein in plant species X, using e.g. gene silencing vectors, will lead to a reduction or suppression of the characteristic while overexpression in a susceptible plant will lead to enhanced resistance. Also, complementation with a functional protein will be capable of restoring or conferring the characteristic. The skilled person will have no difficulties in testing functionality.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3'non-translated sequence comprising e.g. transcription termination sites. "Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). An active protein in certain embodiments refers to a protein being constitutively active. The coding sequence is preferably in sense-orientation and encodes a desired, biologically active protein or peptide, or an active peptide fragment. In gene silencing approaches, the DNA sequence is preferably present in the form of an antisense DNA or an inverted repeat DNA, comprising a short sequence of the target gene in antisense or in sense and antisense orientation, "Ectopic expression" refers to expression in a tissue in which the gene is normally not expressed.

A nucleic acid as disclosed herein may include any polymer or oligomer of pyrimidine and purine bases, preferably cytosine, thymine, and urea, and adenine and guanine, respectively (See Albert L. Lehninger, *Principles of Biochemistry*, at 793-800 (Worth Pub. 1982) which is herein incorporated by reference in its entirety for all purposes). The present disclosure contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. The term "isolated" thus means isolated from naturally occurring sources or artificially or synthetically produced. A nucleotide sequence can for example be isolated by cloning it into a host organism such as a BAC clone. Typically, when a nucleotide sequence is isolated, it comprises at most 500, preferably at most 250, more preferably at most 100, more preferably at most 50 or most preferably at mast 20 contiguous nucleotides of the nucleotide sequence(s) that naturally directly flanks the nucleotide sequence which is now isolated. In addition, the nucleic acids may be DNA or RNA, or a mixture thereof, and may exist permanently or transitionally in singlestranded or double-stranded form, including homoduplex, heteroduplex, and hybrid states.

Plants according to the invention include Cucurbitaceae, Gramineae, Solanaceae or Asteraceae (Compositeae), maize/corn (*Zea* species), wheat (*Triticurn* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc), sunflower (*Helianthus annus*), safflower, yam, cassava, alfalfa (*Medicago sativa*), rice (*Oryza* species, e.g. *O. sativa* indica cultivar-group or japonica cultivar-group), forage grasses, pearl millet (*Pennisetum* spp. e.g. *P. glaucum*), tree species (*Pinus*, poplar, fir, plantain, etc), tea, coffee, oil palm, coconut, vegetable species, such as pea, zucchini, beans (e.g. *Phaseolus* species), hot pepper, cucumber, artichoke, asparagus, eggplant, broccoli, garlic, leek, lettuce, onion, radish, turnip, tomato, potato, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. Rose, *Petunia, Chrysanthemum*, Lily, *Gerbera* species), herbs (mint, parsley, basil, thyme, etc.), woody trees (e.g. species of *Populus, Salix, Quercus, Eucalyptus*), fibre species e.g. fax (*Linum usitatissimum*) and hemp (*Cannabis sativa*), and others.

A "recombinant plant" or 'recombinant plant part' or "transgenic plant" is a plant or plant part (seed or fruit or leaves, for example) which comprises the chimeric gene in all cells and plant parts, at the same locus, even though the gene may not be expressed in all cells.

The term "sequencing" refers to determining the order of nucleotides (base sequences) in a nucleic acid sample, e.g. DNA or RNA. Many techniques are available such as Sanger sequencing and Next-Generation sequencing technologies such as offered by 454 or Solexa technologies.

SEQ ID NO:1-8 are based on the relevant regions of EPSPS as shown in FIG. 1: Maize (SEQ ID NO:1), Rice (SEQ ID NO:2), Wheat (SEQ ID NO:3), Tomato (SEQ ID NO:4), *Arabidopsis* (SEQ ID NO:5), Onion (SEQ ID NO:6), *Salmonella* (SEQ ID NO:7), and *E. coli* (SEQ ID NO:8). With respect to any unintended difference between the sequences of any of SEQ ID NO:1-8 and the corresponding sequence as shown in FIG. 1, it is hereby noted that the sequences as shown in FIG. 1 are leading and should be considered as the basis for correction of any such unintended difference.

For amino acids the following common abbreviations may be used throughout the text:

| Ala | A | Alanine |
|-----|---|---------|
| Arg | R | Arginine |
| Asn | N | Asparagine |
| Asp | D | Aspartic acid (Aspartate) |
| Cys | C | Cysteine |
| Gln | Q | Glutamine |
| Glu | E | Glutamic acid (Glutamate) |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |

-continued

| Thr | T | Threonine |
|-----|---|-----------|
| Trp | W | Tryptophan |
| Tyr | Y | Tyrosine |
| Val | V | Valine |
| Asx | B | Aspartic acid or Asparagine |
| Glx | Z | Glutamine or Glutamic acid |
| Xaa | X | Any amino acid |
|     |   | (sometime - is used to refer to any amino acid). |

DETAILED DESCRIPTION OF THE INVENTION

The invention relates to a newly identified mutation in an EPSPS coding sequence that corresponds to a change of an amino acid at position 44, as shown in FIG. 1. In a preferred embodiment this change is in combination with at least one further mutation in said EFSPS coding sequence, preferably with a further mutation that corresponds to a change of an amino acid at a position chosen from the group consisting of 101, 106, and 179, as shown in FIG. 1. FIG. 1 shows the mature protein lacking the chloroplast targeting signal while the other figures show the complete protein, including such target signal, as will be clearly understood by the person skilled in the art. A skilled person will therefore have no problem determining corresponding positions and mutations according to the invention in either nucleotide sequences coding for EPSPS enzymes or in amino acid sequences of EPSPS enzymes, for example by aligning sequences of various EPSPS genes, in accordance with the data of FIG. 1.

During experimentation with various plant materials including protoplasts, including tomato protoplasts, plant material, e.g. callus, was obtained that was capable of growing on medium containing glyphosate and the plant material, e.g. the callus, appeared resistant against this herbicide while maintaining growth.

The EPSPS genes from these different glyphosate-resistant materials were sequenced using methods available to the skilled person. A new and unexpected mutation was indentified in the coding region for the EPSPS, which mutation in the genetic materials leads to the change of an amino acid in the encoded EPSPS enzyme at position 44 as indicated in FIG. 1. It was found that a plant (deli) carrying this mutation shows (enhanced) glyphosate resistance, in fact, and even more surprisingly, it was found that already existing glyphosate resistance of a plant (cell) may be further enhanced by introducing the above-identified mutation at position 44 in the EPSPS coding sequence present in said plant. For example, and in particular, the glyphosate resistance of a plant expressing an EPSPS coding sequence that confers glyphosate resistance by having a mutation leading to change of an amino acid in the original EPSPS enzyme at a position chosen from the group consisting of 101, 106, and 179, as shown in FIG. 1, may be further enhanced by introduction of a mutation leading to a change of an amino acid at position 44, as shown in FIG. 1. In other words, the newly indentified mutation may advantageously be used to enhance the glyphosate resistance conferring capabilities of other and known mutations in EPSPS enzymes.

Certain aspects of the present invention thus relate to four different mutations in said EPSPS coding sequence that corresponds to a change of amino acids at specific positions. In general these mutations can be referred to in the remainder of the text as mutations A, B, C, and D:

Mutation A

The first mutation in the EPSPS coding sequence may be referred to as Mutation A and leads to a change of the amino acid at position 44 in the EPSPS enzyme, as shown in FIG. 1, e.g. leading to glyphosate resistance, in comparison to the same EPSPS coding sequence not having said mutation. For example, and preferably, the amino acid at position 44 that is changed due to a mutation in the EPSPS-coding sequence is an Asparagine (N), as shown in the amino acid sequences of the plants shown in FIG. 1 (in other words the original amino acid at position 44 is to be changed according to the invention and the original amino acid may be an Asparagine). Thus, preferably this mutation results in an amino add at position 44 in the EPSPS-coding sequence which is not Asparagine (N).

Although the amino acid on position 44, preferably an Asparagine (N), may, according to the invention, be altered into any other amino acid, as long as it is useful in providing glyphosate resistance, preferably the EPSPS-coding sequence comprises a mutation that leads to a change of the amino acid at position 44, preferably Asparagine, into an Aspartic acid (D), again as shown in FIG. 1.

Thus, in a preferred embodiment, the EPSPS encoding sequence encodes an EPSPS enzyme wherein the amino acid at position 44 is an Aspartic acid (D), independently of the amino acid that was present at said position before.

Mutation B

The second mutation (reference may be made to this mutation as Mutation B) leads to the change of the amino acid at position 101 in the EPSPS enzyme, as shown in FIG. 1, e.g. leading to glyphosate resistance, in comparison to the same EPSPS coding sequence not having said mutation. For example, and preferably, the amino acid at position 101 that is changed due to a mutation in the EPSPS-coding sequence is a Glycine (G), as shown in the amino acids sequences for the plants shown in FIG. 1 (in other words the original amino acid at position 101 may be altered according to the invention, and the original amino acid may be a Glycine). Thus, preferably this mutation results in an amino acid at position 101 in the EPSPS-coding sequence which is not Glycine (G). In the *E. coli* EPSPS amino acid sequence of FIG. 17, Mutation B corresponds to a change of the amino acid at position 96. Although the amino acid on position 101, preferably a Glycine (G), may be changed into any other amino acid, as long as it is useful in providing glyphosate resistance, preferably the EPSPS-coding sequence comprises a mutation that leads to a change of the amino acid at position 101, preferably Glycine, into an Alanine (A), again as shown in FIG. 1.

Thus, in a preferred embodiment, the EPSPS encoding sequence encodes an EPSPS enzyme wherein the amino acid at position 101 is a Alanine (A), independently of the amino acid that was present at said position before.

The structure of the G101A mutation revealed that an alanine at position 101 sterically hinders the binding of glyphosate to the PEP binding site, which is accompanied by a corresponding increase in the Km of PEP (see Eschenburg, S., Healy, M. L., Priestman, Lushington, G. H. and Schonbrunn, E. (2002) How the mutation glycine96 to alanine confers glyphosate insensitivity to 5-enolpyruvyl shikimate-3-phosphate synthase from *Escherichia coli*. Planta 216, 129-135).

Mutation C

The third mutation (Reference may be made to this mutation as Mutation C) leads to the change of the amino acid at position 106 in the EPSPS enzyme, as shown in FIG. 1, e.g. leading to glyphosate resistance, in comparison to the same EPSPS coding sequence not having said mutation. For example, and preferably, the amino acid at position 106 that is changed due to a mutation in the EPSPS-coding sequence is a Proline (P), as shown in the amino acids sequences for the plants shown in FIG. 1 (in other words the original amino acid at position 106 may be a Praline, and that amino acid may be changed). Thus, preferably this mutation results in an amino acid at position 106 in the EPSPS-coding sequence which is not Praline (P).

Although the amino acid on position 106, preferably a Praline (P), may be changed into any other amino acid, as long as it is useful in providing glyphosate resistance, preferably the EPSPS-coding sequence comprises a mutation that leads to a change of the amino acid at position 106, preferably Praline, into a Leucine (L), again as shown in FIG. 1.

Thus, in a preferred embodiment, the EPSPS encoding sequence encodes an EPSPS enzyme wherein the amino acid at position 106 is a Leucine (L), independently of the amino acid that was present at said position before.

Mutation D

The fourth mutation (which is newly identified) (Reference may be made to this mutation as Mutation D) leads to the change of the amino acid at position 179 in the EPSPS enzyme, as shown in FIG. 1, e.g. leading to glyphosate resistance, in comparison to the same EPSPS coding sequence not having said mutation. For example, and preferably, the amino acid at position 179 that is changed due to a mutation in the EPSPS-coding sequence is a Serine (S), as shown in the amino acids sequences for the plants shown in FIG. 1 (in other words the original amino acid at position 179 may be a Serine, and that amino acid may be changed). Thus, preferably this mutation results in an amino acid at position 179 in the EPSPS-coding sequence which is not Serine (S).

Although the amino acid on position 179, preferably a Serine (5), may be changed into any other amino acid, as long as it is useful in providing glyphosate resistance, preferably the EPSPS-coding sequence comprises a mutation that leads to a change of the amino acid at position 179, preferably Serine, into an Asparagine (N), again as shown in FIG. 1.

Thus, in a preferred embodiment, the EPSPS encoding sequence encodes an EPSPS enzyme wherein the amino acid at position 179 is an Asparagine (N), independently of the amino acid that was present at said position before.

Various (amino acid or nucleic acid encoding such amino acid) sequences of EPSPS enzymes of various organisms are shown in any of the FIGS. 1-22; in most of the FIGS. 4-22 the amino acid positions referred to as 44, 101, 106, and 179 and in FIG. 1 are indicated by underlining. It will be understood by the skilled person that the mutations described herein, under reference to FIG. 1, can also be present/introduced in the corresponding positions in any EPSPS coding sequence and/or EPSPS enzyme of any organism, for example those shown in the Figures. The corresponding position in other sequences is easily established by comparison of the sequences as shown in FIG. 1. This can be done by taking the sequence of the EPSPS protein from the relevant organism (particularly plant), performing an alignment with the *A. thaliana* protein and identifying the amino acid positions corresponding to N44, G101, P106 and 8179. The sequences shown in FIG. 4 and further include the chloroplast targeting signal; FIG. 1 shows the mature protein lacking the chloroplast targeting signal.

In a first aspect, the invention provides for a (isolated) nucleotide sequence that encodes an EPSPS enzyme, preferably a plant EPSPS enzyme, that confers glyphosate resistance to a plant (cell), characterized in that the nucleotide sequence comprises at least one mutation that corresponds to a change of an amino acid at position 44, as shown in FIG. 1.

Accordingly the amino acid at position 44 in the EPSPS-coding sequence preferably is not Asparagine (N).

Preferably, the amino acid that is changed at position 44 is Asparagine. Preferably the amino acid at position 44 is changed into a proteinogenic amino acid having a pI (isoelectric point) of 3.50 or below, being Aspartic acid or Glutamic Acid, preferably Aspartic Acid. In other words, the amino acid at position 44 in the EPSPS enzymes according to the invention (providing glyphosate resistance) is preferably an Aspartic acid or a Glutamic Acid, preferably an Aspartic Acid.

Preferably, said change is in comparison to a/the wild-type EPSPS enzyme, for example obtained from a plant in which glyphosate resistance is to be introduced and/or enhanced.

It was found that this particular amino acid change at position 44, as shown in FIG. 1 (change into a proteinogenic amino acid having a pi (isoelectric point) of 3.50 or below, being Aspartic acid or Glutamic Acid, preferably Aspartic Acid) renders advantageous results with respect to glyphosate resistance conferred by the resulting EPSPS enzyme and/or leads to an EPSPS enzyme with an improved activity towards its normal substrate, in comparison with a corresponding wild-type EPSPS, or an EPSPS enzyme wherein the amino acid at position 44 is another amino acid than Aspartic acid or Glutamic Acid.

Thus, a plant (cell) carrying said nucleotide sequence, e.g. by alteration of the original sequence present in said plant, may display (enhanced) glyphosate resistance. In the context of the present invention, glyphosate-resistance of a plant (cell) refers to the ability of said plant (cell) to survive or continue to grow in the presence of certain concentrations of glyphosate that typically kill or inhibit growth of a wild-type plant (cell). Preferably, said plant (cell) maintains normal or only slightly reduced (e.g. up to 20% less mass accumulation) growth under such circumstances.

Enhancing glyphosate resistance of a plant (cell) refers to conferring to said plant (cell) the ability to survive or continue to grow in the presence of a concentration of glyphosate that is higher than the concentration of glyphosate that would normally inhibit survival and/or growth of said plant (cell) e.g. not carrying a glyphosate resistant EPSPS. This provides for a plant (cell) with enhanced glyphosate resistance. In other words, a plant exhibiting a certain level of resistance to glyphosate, for example due to the presence of a mutation, may show resistance to a higher concentration of glyphosate by the presence of the mutation at position 44.

For example, if a reference glyphosate-resistant plant (cell) can only grow on a culture medium containing max. 50 µM (or 50 mg/l) glyphosate, a plant (cell) with enhanced glyphosate resistance may grow on a culture medium containing more than 50 µM (or 50 mg/l) glyphosate, for example 55 µM (or 55 mg/l) glyphosate or more, such as 100 µM (or 100 mg/l), 200 µM (or 200 mg/l) or 300 µM (or 300 mg/l) glyphosate. If a reference glyphosate-resistant plant (cell) can grow on a culture medium containing 100 µM (or 100 mg/l) glyphosate, a plant (cell) with enhanced glyphosate resistance can grow on a culture medium containing more than 100 µM (or 100 mg/l) glyphosate, for example 110 µM (or 110 mg/l) glyphosate or more, such as 200 µM (or 200 mg/l), 300 µM (or 300 mg/l) or 400 µM (or 400 mg/l) glyphosate. The enhanced capability of the plant (cell) to grown under conditions of increased concentration of glyphosate can be provided for by the introduction of a mutation leading to the change of an amino acid at position 44 as shown in FIG. 1, preferably the amino acid in the improved EPSPS enzyme being an Aspartic acid.

In the context of the present invention, growth includes, for instance, photosynthesis, increased rooting, increased height, increased biomass, developments of new leaves, development of crops, and/or increased crop yield. An example is detailed below.

Enhanced glyphosate-resistance of a plant (cell) may however also refer to increased survival and/or increased growth of a plant (cell) in the presence of a specific concentration of glyphosate, in comparison to the normally displayed survival and/or growth of such plant (cell) in the presence of said concentration of glyphosate. In other words, a plant exhibiting a certain level of resistance to glyphosate, for example due to the presence of a mutation, will show increased survival or growth in the presence of a specific concentration of glyphosate by the presence of the mutation at position 44, as detailed herein.

For example, a reference glyphosate-resistant plant(s) (cell(s)) growing on a culture medium containing 50 µM (or 50 mg/l) glyphosate show(s) a survival rate of 90% after 50 days and a growth rate of 100 g dry weight per 50 days, plant(s) (cell(s)) with enhanced glyphosate resistance growing on a culture medium containing 50 µM (or 50 mg/l) glyphosate may show increased survival and/or increased growth. Comparably, if reference glyphosate-resistant plant(s) (cell(s)) growing on a culture medium containing 100 µM (or 100 mg/l) glyphosate show(s) a specific survival rate and a specific growth rate, plant(s) (cell(s)) with enhanced glyphosate resistance growing on a culture medium containing 100 µM (or 100 mg/l) glyphosate may show increased survival and/or increased growth.

In a preferred embodiment, the nucleotide sequence that encodes an EPSPS enzyme according to the invention and as disclosed herein, is further characterized in that the nucleotide sequence comprises at least one further mutation that on its own renders said nucleotide sequence to encode an EPSPS enzyme that confers glyphosate resistance to a plant, preferably wherein said at least one further mutation corresponds to a change of an amino acid at a position chosen from the group consisting of 101, 106, or 179, as shown in FIG. 1. Accordingly, in the EPSPS-coding sequence, the amino acid at position 101 preferably is not Glycine (G), the amino acid at position 106 preferably is not Proline (P), and/or the amino acid at position 179 preferably is not Serine (3).

For example, a nucleotide sequence that encodes an EPSPS enzyme with in its amino acid sequence a mutation (for example corresponding to position 101, 106, or 179 as shown in FIG. 1) that confers glyphosate resistance to said EPSPS enzyme may according to the invention be provided with at least one further mutation that corresponds to a change of an amino acid at position 44 as disclosed herein.

In a preferred embodiment, the amino acid that is changed at position 101 is Glycine.

In a preferred embodiment, the amino acid that is changed at position 106 is Proline.

In a preferred embodiment, the amino acid that is changed at position 179 is Serine.

Preferably, the amino add at position 101 is changed into an Alanine.

Preferably, the amino add at position 106 is changed into a Leucine.

Preferably, the amino acid at position 179 is changed into an Asparagine.

In other words, according to the invention preferably, the amino acid at position 101 is an Alanine or the amino acid at positron 106 is a Proline or the amino acid at position 179 is an Asparagine. It was found that, in combination with preferably an Aspartic acid or a Glutamic Acid, preferably an Aspartic Acid, at position 44, as shown in FIG. 1 in an EPSPS enzyme, these particular amino acid (changes) render advantageous results with respect to glyphosate resistance conferred by the resulting EPSPS enzyme and/or leads to an EPSPS enzyme with an improved activity towards its normal substrate, in comparison with a corresponding wild-type EPSPS, or with an EPSPS that is changed at said positions into other than the preferred amino acids.

In the literature and in practice, different numbers are used to refer to identical amino acid positions in the amino acid sequence of an EPSPS enzyme, particularly if amino acid sequences of different organisms are aligned. To obviate ambiguity with respect to the numbers used in this description, we introduced FIG. 1 wherein the relevant region of EPSPS enzyme amino acid sequences of maize (corn), rice, wheat, tomato, *Arabidopsis*, onion, *Salmonella*, and *E. coli* are aligned and numbered. Furthermore, the important amino acids highlighted. The amino acid positions disclosed and referred herein are relative to FIG. 1.

Where in this description (or in the claims) reference is made to amino acid positions 44, 101, 106, and/or 179 it is to be construed that also is meant a change of an amino acid at a position analogous to said position 44, 101, 106, and/or 179 in an amino acid sequence that is substantially homologous to EPSPS protein having amino add sequences as shown in FIG. 1, as will be understood by the skilled person, for example has a amino acid identity of at least 70%, preferably at least 75%, more preferably at least 80%, even more preferable 64%, 88%, 92%, 95%, 98% or 99% identity over its entire length with a protein having an amino acid sequence shown in FIG. 1, and/or is functional, in other words has EPSPS enzymatic activity.

For example, although the relevant region of EPSPS of potato, or sunflower are not shown in FIG. 1, they can be aligned to the sequences disclosed in FIG. 1 and according to methods known to the skilled person (for Example using the CLC Bio Main Workbench package (www.clcbio.com). For example, an amino acid sequence of a potato EPSPS enzyme that has EPSPS enzymatic activity and comprises the sequence Threonine (T)-Valine (V)-Valine (V)-Aspartic acid (D)-Aspartic acid (D)-Leucine (L)-Leucine (L)-Asparagine (N), will correspond to position 40-47 as shown in FIG. 1. As this sequence comprises a change at a position corresponding to position 44 as shown in FIG. 1, namely Aspartic acid instead of Asparagine, it is according to the present invention.

The inventors have realized that the limiting factor of mutations in the EPSPS enzyme might be the reduced biochemical activity they confer to the EPSPS enzyme. For instance, a T42M mutation in *Salmonella* gives a 25 fold lower affinity for its normal substrate (PEP) but a 26 fold higher tolerance for glyphosate. This fitness penalty may mean that such mutant genes are not sufficient for normal growth under field conditions. Comparably, Roundup Ready soybean crops, compared to the top conventional varieties, show a 6.7% lower yield (Charles Benbrook. Evidence of the Magnitude and Consequences of the Roundup Ready Soybean Yield Drag from University-Based Varietal Trials in 1998. Ag BioTech InfoNet Technical Paper Number 1).

It is believed that having an EPSPS mutant with Mutation A, i.e. at position 44, preferably as described above, alone or in combination with another mutation that renders glyphosate resistance, preferably a mutation as described herein, may lead to (improved) resistance to glyphosate. This may be without (further) inhibiting of enzyme activity or even improved enzyme activity. It was particularly unexpected to find that the combination of Mutation A (at position 44) with another mutation that renders glyphosate resistance, e.g. Mutation B (at position 101), Mutation C (at position 106), or Mutation D (at position 179) enhances glyphosate resistance beyond what may be expected on the basis of Mutation A alone and said another mutation alone.

For example, a nucleotide sequence encoding an EPSPS enzyme, that comprises a mutation that renders said EPSPS enzyme to confer glyphosate resistance to a plant (cell), preferably a mutation that corresponds to a change of an amino acid at a position chosen from the group consisting of 101, 106, or 179, as shown in FIG. 1, may be provided with a further mutation corresponding to a change of an amino acid at a position 44, as disclosed herein, to obtain a nucleotide sequence encoding an EPSPS enzyme that may have increased activity towards its normal substrate or is better resistant to glyphosate, in comparison to when said mutation corresponding to a change of an amino acid at position 44 is not provided in said nucleotide sequence encoding an EPSPS enzyme. For example said increased activity encompasses a 1.5, 2, 4, or 5 fold increase of the affinity of the EPSPS enzyme for its normal substrate. Without being bound to theory, the current inventors believe that said effects may relate to changes in the active site of the EPSPS enzyme that lead to a lowered affinity of the enzyme for glyphosate and/or an increased affinity of the enzyme for its normal substrate.

Other mutated or modified EPSPSs, such as those described in U.S. Pat. Nos. 5,310,687, 5,866,775, 6,225,114, and 6,248,876, or natural EPSPS variants showing glyphosate-resistance, can also be used in combination with the present invention. In addition, bacteria-derived, glyphosate-resistant EPSPS variants, and for example after fusion with a chloroplast transit peptide, can also be used in combination with the present invention.

As will be understood by a skilled person, a mutation may be introduced in a nucleotide sequence encoding EPSPS as defined herein by the application of mutagenic compounds, such as ethyl methanesulfonate (EMS) or other compounds capable of (randomly) introducing mutations in nucleotide sequences. Said mutagenic compounds or said other compound may be used as a means for creating plant(s) cell(s) harboring a mutation in a nucleotide sequence encoding an EPSPS enzyme. Plant(s) cell(s) harboring a mutation according to the invention may then be selected by means of sequencing.

Alternatively, the introduction of a mutation in a nucleotide sequence encoding an EPSPS enzyme according to the invention is effected by the introduction of transfer-DNA (T-DNA) in a plant, for instance T-DNA of the tumor-inducing (Ti) plasmid of some species of bacteria such as *Agrobacterium tumefaciens*. A T-DNA element comprising a nucleotide sequence encoding an EPSPS enzyme that comprises an amino acid change at position 44 according to the invention, optionally in combination with another mutation described herein, may be introduced in said plant, leading to a plant (cell) with (enhanced) glyphosate resistance obtained by the method according to the invention (see for example Krysan et al. 1999 The Plant Cell, Vol 11. 2263-2290).

Likewise advantage can be taken from the use of transposable element insertion (See for Example Kunze et al (1997) Advances in Botanical Research 27 341-370 or Chandlee (1990) Physiologia Planta 79(1) 105-115).

Preferably, introducing a mutation in a nucleotide sequence encoding a EPSPS enzyme according to the invention is introduced by genome engineering techniques, such as techniques based on homologous recombination, or oligo-directed mutagenesis (ODM), for instance as described in WO2007073170; WO2007073149; WO2009002150; and WO2007073166). By applying ODM, specific nucleotides can be altered in a nucleotide sequence encoding EPSPS, whereby a mutation according to the invention may be introduced.

The invention also provides for an EPSPS enzyme that confers glyphosate resistance to a plant, preferably a plant EPSPS enzyme, encoded by a nucleotide sequence according to the invention as described herein. Such EPSPS enzyme may be derived from a bacterium or a plant. It is however preferred that the EPSPS enzyme, or the nucleotide encoding said EPSPS enzyme, is derived from a crop plant, more preferably cotton, tomato, potato, onion, rice, wheat, maize, or sunflower, because the EPSPS enzyme may then more closely resemble the natural EPSPS enzyme of the plants that are most used in agriculture. Such a more natural EPSPS enzyme may render crop plants to generate higher crop yield in agriculture.

The EPSPS enzyme according to the invention may be expressed in a plant, preferably a crop plant, more preferably cotton, tomato, potato, onion, rice, wheat, maize, sunflower, sugar beet or *Brassica* species.

Cotton includes *Gossycium* species, e.g. *G. hirsutum, G. barbadense*, tomato includes *Solanum lycopersicum* species, potato includes *Solanum tubersosum* species, onion includes *Allium* species, specifically *Allium cepa* species, rice includes *Oryza sativa* species e.g. *O. sativa* indica cultivar-group or *japonica* cultivar-group and *Oryza glaberrima* species, wheat includes *Triticum* species including *T. monococcum* and *T. dicoccoides*, maize/corn includes *Zea* species, sunflower includes *Helianthus annus*. *Brassica* species include canola, oilseed rape, cauliflower, broccoli, cabbage, *B. napus, B. juncea, B. rape* and *B. oleracea*, and sugar beet includes *Beta vulgaris*.

The invention also provides for a vector comprising a nucleotide sequence according to the invention and a host comprising such vector. Said vector may be used to transfer a nucleotide according to the invention into another cell such as a plant cell. Different types of vectors include plasmids, bacteriophages and other viruses, cosmids, and artificial chromosomes.

Also provided is a plant or transgenic plant or part thereof comprising a nucleotide sequence according to the invention and/or a fragment thereof and/or an EPSPS enzyme according to the invention. Said fragment is at least of a length that is sufficient to determine that the fragment is derived from a nucleotide sequence encoding an EPSPS enzyme, and further comprises Mutation A according to the invention, preferably in combination with at least one further mutation that would confer, when in a complete nucleotide sequence encoding an EPSPS enzyme, glyphosate resistance upon a plant. Preferably, said at least one further mutation comprises Mutation B, Mutation C, and/or Mutation D, as described herein and according to the invention.

The fragment may for example have a length of at least 10, 30, 100, 500 consecutive nucleotides. A skilled person will have no problem in determining whether such fragment comprises a mutation as described herein. He can do so, for example, by aligning the fragment with the EPSPS coding sequence.

A transgenic crop plant contains a gene or genes which have been artificially inserted, i.e. wherein said gene or genes have not initially been acquired through pollination. A non transgenic plant thus does not contain a gene or genes which have been artificially inserted. Also provided is a seed derived from a plant or transgenic plant or part thereof as mentioned above, comprising a nucleotide sequence according to the invention and/or a fragment thereof and/or an EPSPS enzyme according to the invention.

Said fragment is at least of a length that is sufficient to determine that the fragment is derived from a nucleotide sequence encoding an EPSPS enzyme, and further comprises at least the Mutation A (position 44) according Co the invention.

The fragment may for example have a length of at least 10, 30, 100, 500 consecutive nucleotides. A skilled person will have no problem in determining whether such fragment comprises a mutation as described herein. He can do so, for example, by aligning the fragment with the EPSPS coding sequence.

In another aspect, the invention relates to a method for providing a glyphosate resistant plant (cell), the method comprising:
  a) providing a plant (cell) that comprises a nucleotide sequence that encodes an EPSPS enzyme, preferably a plant EPSPS enzyme, characterized in that the nucleotide sequence comprises at least one mutation that corresponds to a change of an amino acid at position 44, as shown in FIG. 1.

In the above-mentioned method it is preferred that the amino acid that is changed at position 44 is Asparagine and/or that the amino add at position 44 is changed into an Aspartic Acid, preferably in comparison to wild-type EPSPS. In other words, the amino acid at position 44, as shown in FIG. 1, is preferably an Aspartic Acid.

In yet another aspect, the invention relates to a method for providing a plant (cell) with resistance to glyphosate, the method comprising:
  a) providing a plant (cell) that comprises a nucleotide sequence that encodes an EPSPS enzyme, preferably a plant EPSPS enzyme, characterized in that the nucleotide sequence comprises at least one mutation that corresponds to a change of an amino acid at position 44, as shown in FIG. 1, and at least one further mutation that on its own renders said nucleotide sequence to encode an EPSPS enzyme that confers glyphosate resistance to a plant, preferably wherein said at least one further mutation corresponds to a change of an amino acid at a position chosen from the group consisting of 101, 106, or 179, as shown in FIG. 1.

In yet another aspect, the invention relates to a method for providing a plant (cell) with resistance to glyphosate, the method comprising:
  a. providing a plant (cell) that comprises a nucleotide sequence that encodes an EPSPS enzyme, preferably a plant EPSPS enzyme;
  b. providing a mutation that corresponds to a change of an amino acid at position 44, as shown in FIG. 1, in said nucleotide sequence of step a), preferably in said plant of step a).

Thus, preferably thereby a mutation is provided that results in an amino acid at position 44 in the EPSPS-coding sequence which is not Asparagine (N), e.g. leading to glyphosate resistance, in comparison to the same EPSPS coding sequence not having the mutation.

In yet another aspect, the invention relates to a method for enhancing glyphosate resistance of a plant (cell), the method comprising:
a) providing a plant (cell) that comprises a nucleotide sequence that encodes an EPSPS enzyme that confers glyphosate resistance to a plant, preferably a plant EPSPS enzyme, and preferably characterized in that the nucleotide sequence comprises at least one mutation that corresponds to a change of an amino acid at a position chosen from the group consisting of 101, 106, or 179, as shown in FIG. 1;
b) providing a mutation that corresponds to a change of an amino acid at position 44, as shown in FIG. 1, in said nucleotide sequence of step a), preferably in said plant (cell) of step a).

Thus, preferably thereby a mutation is provided that results in an amino acid at position 44 in the EPSPS-coding sequence which is not Asparagine (N), e.g. leading to glyphosate resistance, in comparison to the same EPSPS coding sequence not having the mutation.

Providing a mutation that corresponds to a change of an amino acid at position 44, as shown in FIG. 1, in a nucleotide sequence that encodes an EPSPS enzyme, preferably a plant EPSPS enzyme, may be performed by Targeted Nucleotide Exchange (TNE), i.e. by introduction of at least one oligonucleotide capable of hybridizing to the nucleotide sequence of step a) and comprising a mismatch with respect to the nucleotide sequence of step a), wherein the position of the mismatch corresponds to the position of a mutation that corresponds to a change of an amino acid at position 44, as shown in FIG. 1, in a nucleotide sequence that encodes an EPSPS enzyme, preferably a plant EPSPS enzyme.

Once introduced into the cell, e.g. by electroporation or PEG-mediated oligonucleotide uptake, such oligonucleotide can hybridize (basepair) with the complementary sequence of the nucleotide sequence to be altered (i.e. the target locus in the nucleotide sequence that encodes an EPSPS enzyme). By deliberately designing a mismatch in the oligonucleotide, the mismatch may impart a nucleotide conversion at the corresponding position in the target genomic sequence. This may result in the provision of a mutation that corresponds to a change of an amino add at position 44, as shown in FIG. 1. Likewise, and depending on the type of mismatch(es) that is deliberately designed, this may result in the provision of a mutation that corresponds to a change of an amino acid at position 101, 106, and/or 179, as shown in FIG. 1.

The oligonucleotide may have a length of between 10-500 nucleotides, preferably 15-250 nucleotides, more preferably between 10-200 nucleotides, most preferably between 15-150 nucleotides. The oligonucleotide may contain locked nucleic acids (LNAs), preferably located one nucleotide upstream or downstream from the mismatch. The oligonucleotide may alternatively or additionally contain propynylated bases. The TNE method is described in Applicant's patent publications WO2007073166, WO2007073170, WO2009002150. The oligonucleotide may further contain at least 4, at least 3, 3, 2 or 1 phosphorothioate linkages at the 5' end and/or the 3' end, both ends or flanking the mismatch.

It is further preferred that in the above-mentioned method, the amino acid that is changed at position 44 is Asparagine and/or that the amino acid at position 44 is changed into an Aspartic Acid aid/or the amino acid that is changed at position 101 is Glycine and/or the amino acid that is changed at position 106 is Praline and/or the amino acid that is changed at position 179 is Serine and/or the amino acid at position 101 is changed into an Alanine and/or the amino acid at position 106 is changed into a Leucine and/or the amino acid at position 179 is changed into an Asparagine (see also specific combinations of mutations as described under the heading "Specific combinations of mutations encompassed by the invention").

The plant provided by a method according to the invention can be used for the production of further plants and or plant products derived therefrom. The term plant products refers to those materials that can be obtained from the plants grown, and include fruits, leaves, plant organs, plant fats, plant oils, plant starch, plant protein fractions, either crushed, milled or still intact, mixed with other materials, dried, frozen, and so on. In general such plant products can, for example be recognized by the presence of a nucleotide according to the present invention.

The invention also provides for a method for generating a plant product the method comprising:
a) processing a plant or transgenic plant or part thereof comprising a nucleotide according to the invention and/or a EPSPS enzyme according to the invention, or a plant obtainable by any of the methods according to the invention.

In the above-mentioned method it is preferred that processing is performed by cooking, grinding, drying, milling, baking, cutting, sieving, flaking, peeling, soaking, washing, heating, cooling, crushing, or wetting, to obtain a plant product.

Also provided is a plant product obtainable by the above-mentioned method, preferably a starch-based product or a plant-oil-based product, characterized in the presence of a nucleotide sequence according to the invention and/or a fragment thereof.

Starch-based products may include products such as tomato purée, flour, or any other starch-containing product. Plant-oil-based products may include products such as olive oil, sunflower oil, or any other plant-oil-containing product.

The invention also provides for the use of a nucleotide sequence according to the invention and/or an EPSPS enzyme according to the invention, for enhancing glyphosate resistance of a plant. For example, such nucleotide sequence may be introduced in a plant (cell) thereby effecting (enhanced) glyphosate resistance.

Another aspect of the present invention relates to the use of a mutation that corresponds to a change of an amino acid at position 44, as shown in FIG. 1, for enhancing glyphosate resistance of a glyphosate resistant plant, preferably wherein said plant comprises a nucleotide sequence that encodes an EPSPS enzyme that confers glyphosate resistance to a plant, preferably a plant EPSPS enzyme, preferably characterized in that the nucleotide sequence comprises at least one mutation that corresponds to a change of an amino acid at a position chosen from the group consisting of 101, 106, or 179, as shown in FIG. 1.

In other words, use of a mutation that corresponds to a change of an amino acid at position 44 involves changing an amino acid at position 44, preferably so that the amino acid at position 44 is Aspartic Acid, thereby effecting (enhanced) glyphosate resistance. Yet in other words, said use involves the use of the information that a change of an amino acid at position 44, according to the invention, effects (enhanced) glyphosate resistance.

With respect to the above-mentioned use, it is preferred that the amino acid that is changed at position 44 is Asparagine, and/or the amino acid that is changed at position 101 is Glycine and/or the amino acid that is changed at position 106 is Proline and/or the amino acid that is changed at position 179 is Serine and/or the amino acid at position 44 is changed into an Aspartic Acid and/or the amino acid at position 101 is changed into an Alanine and/or the amino acid at position 106 is changed into a Leucine, and/or the amino acid at position 179 is changed into a Asparagine. Said changes are preferably in comparison to wild-type EPSPS.

Also provided is the use of a mutation as described above, in an EPSPS enzyme resistant to glyphosate, for restoration or improvement of enzyme activity. For example, the mutation leading to the change of the amino acid at position 44, preferably an Asparagine, into another amino acid, preferably Aspartic acid, may be used through introducing it in an enzyme already providing resistance to glyphosate, to further improve activity of the enzyme towards its normal substrate PEP. Preferably, a mutation leading to a change of the amino acid at position 101, preferably a Glycine, into another amino acid, preferably Alanine, and/or a mutation leading to a change of the amino acid at position 106, preferably a Praline, into another amino acid, preferably Leucine, and/or the mutation leading to a change of the amino acid at position 179, preferably Serine, into another amino acid, preferably Asparagine, may (in addition) be introduced in an enzyme already providing resistance to glyphosate, to further improve activity of the enzyme towards its normal substrate PEP.

Below, specific combinations of mutations A, B, C, and D are described that may be used according to the invention.
Specific Combinations of Mutations Encompassed by the Invention:
(Mutations A+B)

In a preferred embodiment, the nucleotide sequence that encodes an EPSPS enzyme comprises a mutation that leads to change of the amino acid at position 44 and a mutation that leads to a change of the amino acid at position 101. In a preferred embodiment, the amino acid that is changed at position 44 is Asparagine. In another preferred embodiment the amino acid that is changed at position 101 is Glycine. In a further preferred embodiment, the amino acid that is changed at position 44 in Asparagine and the amino acid that is changed at position 101 is Glycine. Preferably, the mutation in said nucleotide sequence that leads to the change of the amino acid at position 44 leads to a change into the amino acid Aspartic acid, i.e. a aspartic acid is present at position 44. Preferably, the mutation in said nucleotide sequence that leads to the change of the amino acid at position 101 leads to a change into the amino acid Alanine, i.e. a alanine is present at position 101. Preferably, the mutation in said nucleotide sequence that leads to the change of the amino acid at position 44 leads to a change into the amino acid Aspartic acid, i.e. a aspartic acid is present at position 44 and at the same time the mutation in said nucleotide sequence that leads to the change of the amino acid at position 101 leads to a change into the amino acid Alanine, i.e. a alanine is present at position 101.
(Mutations A+C)

In another preferred embodiment, the nucleotide sequence that encodes an EPSPS enzyme comprises a mutation that leads to change of the amino acid at position 44 and a mutation that leads to a change of the amino acid at position 106. In a preferred embodiment, the amino acid that is changed at position 44 is Asparagine. In another preferred embodiment the amino acid that is changed at position 106 is Proline. In a further preferred embodiment, the amino acid that is changed at position 44 in Asparagine and the amino acid that is changed at position 106 is Proline. Preferably, the mutation in said nucleotide sequence that leads to the change of the amino acid at position 44 leads to a change into the amino acid Aspartic acid, i.e. a aspartic acid is present at position 44 Preferably, the mutation in said nucleotide sequence that leads to the change of the amino acid at position 106 leads to a change into the amino acid Leucine, i.e. an Leucine (L) is present at position 106. Preferably, the mutation in said nucleotide sequence that leads to the change of the amino acid at position 44 leads to a change into the amino acid Aspartic acid. i.e. a esparto acid is present at position 44 and at the same time the mutation in said nucleotide sequence that leads to the change of the amino acid at position 106 leads to a change into the amino acid Leucine, i.e. an Leucine (L) is present at position 106.
(Mutations A+D)

In another preferred embodiment, the nucleotide sequence that encodes an EPSPS enzyme comprises a mutation that leads to change of the amino acid at position 44 and a mutation that leads to a change of the amino acid at position 179. In a preferred embodiment, the amino acid that is changed at position 44 is Asparagine. In another preferred embodiment the amino acid that is changed at position 179 is Serine. In a further preferred embodiment, the amino acid that is changed at position 44 in Asparagine and the amino acid that is changed at position 179 is Serine. Preferably, the mutation in said nucleotide sequence that leads to the change of the amino acid at position 44 leads to a change into the amino acid Aspartic acid, le, a aspartic acid is present at position 44. Preferably, the mutation in said nucleotide sequence that leads to the change of the amino acid at position 179 leads to a change into the amino acid Asparagine (D), i.e. a Asparagine is present at position 179. Preferably, the mutation in said nucleotide sequence that leads to the change of the amino acid at position 44 leads to a change into the amino acid Aspartic acid, i.e. a aspartic acid is present at position 44 and at the same time the mutation in said nucleotide sequence that leads to the change of the amino acid at position 179 leads to a change into the amino add Asparagine, i.e. a Asparagine is present at position 179.

FIGURES

In FIG. 1, the relevant region of EPSPS from Maize (SEQ ID NO:1), Rice (SEQ ID NO:2), Wheat (SEQ ID NO:3), Tomato (SEQ ID NO:4), *Arabidopsis* (SEQ ID NO:5), Onion (SEQ ID NO:6), *Salmonella* (SEQ ID NO:7), and *E. coli* (SEQ ID NO:8) are aligned and the important amino acids highlighted. The amino acid positions disclosed and referred herein are indicated in FIG. 1. As can be seen, the amino acid positions disclosed and referred herein as positions 44, 101, 106, and 179 relate to positions 43, 99, 104, and 177 respectively in SEQ ID NO:1, positions 44, 101, 106, and 179 respectively in SEQ ID NO:2, positions 44, 101, 106, and 179 respectively in SEQ ID NO:3, positions 44, 101, 106, and 179 respectively in SEQ ID NO:4, positions 44, 101, 106, and 179 respectively in SEQ ID NO:5, positions respectively 30, 87, 92, and 165 in SEQ ID NO:6, positions 42, 95, 100 and 169 respectively in SEQ ID NO:7, positions 42, 95, 100, and 169 respectively in SEQ ID NO:8 FIG. 1 shows the mature proteins lacking the chloroplast targeting signal.

FIG. 2 shows the results of a complementation assay in *E. coli* using *A. thaliana* EPSPS variants. Legend of FIG. 2 is shown below:
(1) N44D P106L
(2) S179N
(3) P106L (4) Wild Type
(5) N44D
(6) P106L S179N
(7) Empty FIG. 3 shows the complete *Arabidopsis* EPSPS amino acid sequence, including the chloroplast targeting signal (SEQ ID NO:9). The relevant amino adds are underlined. As can be seen, the amino acid positions disclosed and referred herein as positions 44, 101, 106, and 179 relate to positions 120, 177, 182 and 255 respectively in SEQ ID NO:9.

FIG. 4 shows the complete *Arabidopsis thaliana* EPSPS ORF (SEQ ID NO:10).

FIG. 5 shows the complete *Arabidopsis thaliana* EPSPS ORF comprising mutation A358G that corresponds to N44D (SEQ ID NO:11).

FIG. 6 shows the complete *Arabidopsis thaliana* EPSPS ORF comprising mutation C545T that corresponds to P106L (SEQ ID NO:12).

FIG. 7 shows the complete *Arabidopsis thaliana* EPSPS ORF comprising mutations A358G and C545T that correspond to N44D and P106L respectively (SEQ ID NO:13).

FIG. 8 shows the complete *Arabidopsis thaliana* EPSPS ORF comprising mutation G902A that corresponds to S179N (SEQ ID NO:14).

FIG. 9 shows the complete *Arabidopsis thaliana* EPSPS ORF comprising mutations C545T and G902A that correspond to P106L and S179N respectively (SEQ ID NO:15).

FIG. 10 shows the complete *Arabidopsis thaliana* EPSPS ORF comprising mutations A358G and G902A that correspond to N44D and S179N respectively (SEQ ID NO:16).

FIG. 11 shows the complete *Arabidopsis thaliana* EPSPS ORF comprising mutation G530C that corresponds to G101A (SEQ ID NO:17).

FIG. 12 shows the complete *Arabidopsis thaliana* EPSPS ORF comprising mutations A358G and G530C that correspond to N44D and G101A respectively (SEQ ID NO:18).

FIG. 13 shows the complete Tomato EPSPS nucleotide sequence (SEQ ID NO:19).

FIG. 14 shows the complete Tomato EPSPS2 Nucleotide sequence (SEQ ID NO:20).

Figure 2:
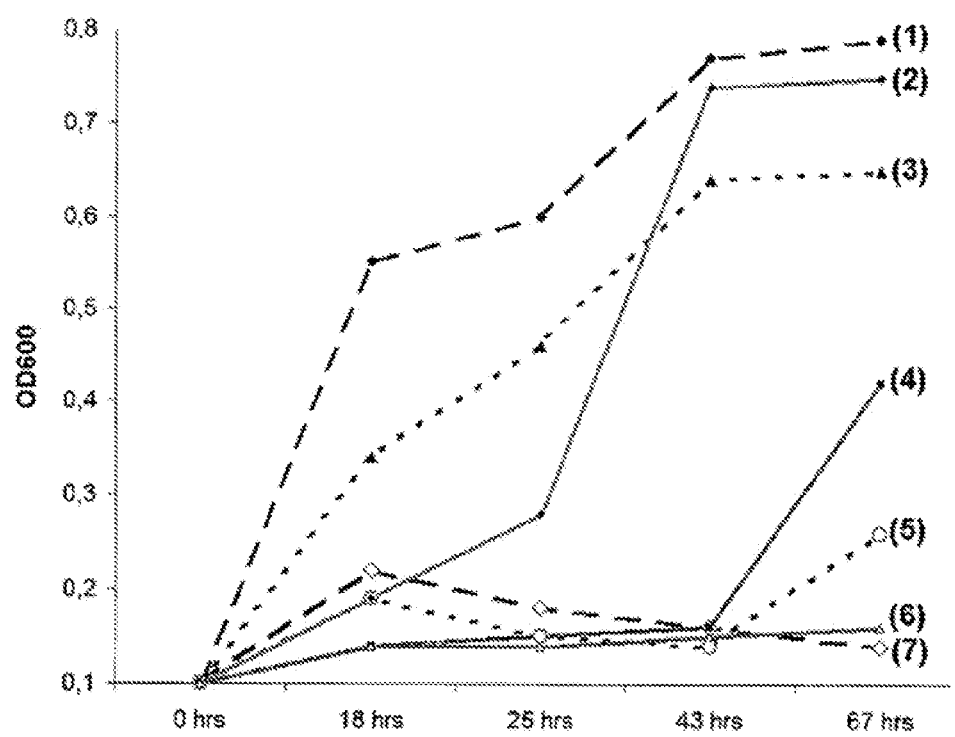

FIG. 15 shows the complete Tomato EPSPS1 Amino Acid Sequence. The relevant amino acids are underlined (SEQ ID NO:21). As can be seen, the amino acid positions disclosed and referred herein as positions 44, 101, 106, and 179 relate to positions 118, 175, 180, and 253 respectively in SEQ ID NO:21.

FIG. 16 shows the complete Tomato EPSPS2 amino acid sequence. The relevant amino acids are underlined (SEQ ID NO:22). As can be seen, the amino acid positions disclosed and referred herein as positions 44, 101, 106, and 179 relate to positions 120, 177, 182, and 255 respectively in SEQ ID NO:22.

FIG. 17 shows the complete *E. coli* EPSPS amino acid sequence. The relevant amino acids are underlined (SEQ ID NO:23). As can be seen, the amino acid positions disclosed and referred herein as positions 44, 191, 106, and 179 relate to positions 43, 96, 101, and 170 respectively in SEQ ID NO:23.

FIG. 18 shows the complete Cotton EPSPS amino acid sequence. The relevant amino acids are underlined (SEQ ID NO:24). As can be seen, the amino acid positions disclosed and referred herein as positions 44, 101, 106, and 179 relate to positions 121, 178, 183, and 256 respectively in SEQ ID NO:24.

FIG. 19 shows the complete Maize EPSPS amino acid sequence. The relevant amino acids are underlined (SEQ ID NO:25). As can be seen, the amino acid positions disclosed and referred herein as positions 44, 101, 106, and 179 relate to positions 46, 102, 107, and 180 respectively in SEQ ID NO:25.

FIG. 20 shows the complete Rice EPSPS amino acid sequence. The relevant amino acids are underlined (SEC) ID NO:26). As can be seen, the amino acid positions disclosed and referred herein as positions 44, 101, 106, and 179 relate to positions 115, 172, 177 and 250 respectively in SEQ ID NO:26.

FIG. 21 shows the complete Wheat EPSPS amino acid sequence. The relevant amino acids are underlined (SEQ ID NO:27). As can be seen, the amino acid positions disclosed and referred herein as positions 44, 101, 106, and 179 relate to positions 110, 167, 172, and 245 respectively in SEQ ID NO:27.

FIG. 22 shows the complete Sunflower EPSPS amino acid sequence. The relevant amino acids are underlined (SEQ ID NO:28). As can be seen, the amino acid positions disclosed and referred herein as positions 44, 101, and 106 relate to positions 118, 175, and 180 respectively in SEQ ID NO:28.

Figure 23:
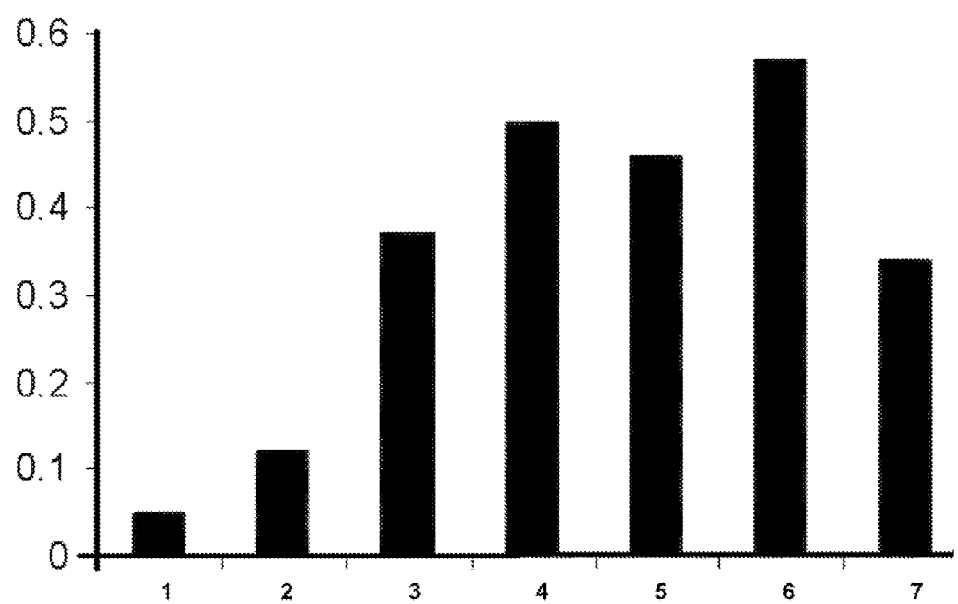

FIG. 23 shows glyphosate tolerance ire transgenic *Arabidopsis* lines: ratio of average seedling weight (+Gly/−Gly). Legend of FIG. 23 is shown below:
(1) Wild type EPSPS gene
(2) EPSPS with mutation N44D
(3) EPSPS with mutation P106L
(4) EPSPS with mutations P106L and N44D (1)
(5) EPSPS with mutations P106L and N44D (2)
(6) EPSPS with mutations P106L and N44D (3)
(7) EPSPS with mutations N44D and S179N

EXAMPLE 1

Applying Mutation A in an EPSPS Enzyme Enhances Glyphosate Resistance Conferred by Said EPSPS Enzyme We tested whether a mutation that corresponds to a change of Asparagine at position 44 into Aspartic Acid, in an EPSPS enzyme (N44D mutation), would be able to provide the EPSPS enzyme with resistance to glyphosate. This was tested by introducing the N44D mutation into EPSPS alone and in combination with other mutations which confer glyphosate resistance to said EPSPS enzyme. These were a mutation that corresponds to a change of Glycine at position 101 into Alanine, in an EPSPS enzyme (G101A), a mutation that corresponds to a change of Proline at position 106 into Leucine, in an EPSPS enzyme (P106L) and a mutation that corresponds to a change of Serine at position 179 into Asparagine, in an EPSPS enzyme (S179N).

Constructs

All experiments utilized the *Arabidopsis thaliana* EPSPS (At2g45300) open reading frame (see FIGS. 4-12) The *Arabidopsis* EPSPS amino acid sequence is depicted in FIG. 3.

First, this sequence was synthesized synthetically (www.geneart.com) and cloned into a vector where it was flanked by BamHI and EcoRI sites. This was then used as a basis construct for the introduction of the N44D (A350G), G101A (G5300), P106L (C545T) and S179N (G902A) mutations which were introduced by site specific mutagenesis (www.geneart.com). The following double mutants were also constructed:

N44D+G101A;
N44D+P106L;
N44D+S179N; and
P106L+S179N.

Each of these EPSPS variants was then cloned as a 1576 bps EcoRI-BamHI fragment into the vector pET302 NT HIS (Invitrogen, product K630203), fusing the EPSPS variants to a 6× His tag and allowing inducible protein expression with IPTG in E. coli. These constructs were introduced into the E. coli expression strain BL21 OAS (Invitrogen) for complementation assays.

Complementation Assays

E. coli is unable to grow in minimal M9 growth medium supplemented with glyphosate due to inhibition of the activity of the endogenous bacterial EPSP synthase AroA. Bacterial growth can be restored by complementation with a glyphosate resistant plant EPSPS gene. The E. coli strains containing the A. thaliana EPSPS variants were grown overnight in 10 ml LB medium containing 100 µg/ml carbenicillin (Duchefa). Strains were then diluted 4 fold in the same medium and allowed to grow for a further 4 hours. The OD600 of each culture was then measured and 1.5 ml culture was centrifuged at 4000 rpm for 10 minutes. The bacterial pellet was resuspended in 500 µl M9 medium (12.8 g/l $Na_2HPO_4$, 3.0 g/l $KH_2PO_4$, 0.5 g/l NaCl, 1.0 g/l $NH_4Cl$, 2.0 g/l glucose, 0.4940 g/l $MgSO_4.7H_2O$, 15 mg/l $CaCl_2.2H_2O$, thiamine and 10 mg/l $FeSO_4.7H_2O$) used to inoculate 10 ml M9 medium containing 1 mM IPTG and 100 µg/ml carbenicillin and 30 mM glyphosate to an OD600 of 0.1. Identical cultures for each strain were also made lacking glyphosate and these were used to assess the growth of each strain without selection. The cultures were then grown at 25° C. and the OD600 was measured over time to assess bacterial growth (see FIG. 2).

Results

The results of the complementation assays are shown in FIG. 2. As expected, the strain containing the empty pET302NT His vector was unable to grow in the presence of glyphosate whereas the strain containing the P106L mutation showed a good level of resistance. Overexpression of the wild type (WT) EPSPS enzyme was able to complement bacterial growth at later time points, presumably due to titration of glyphosate due to high protein expression levels. In other words, presumably, at said later time points the amount of glyphosate was no longer enough to inactivate all expressed EPSPS enzymes.

The results showed that the N44D mutation alone may provide for some resistance to glyphosate, but when combined with the P106L mutation was able to enhance the resistance levels 2.5 fold after 18 hours of growth. This suggests that N44D can be used, preferably as secondary mutation that is able to improve glyphosate resistance. Similar results can be obtained when Mutation A, in this case N44D, was combined with the other mutations described above. Also good resistance was conferred by the S179N mutation alone, but when this was combined with the P106L mutation the EPSPS enzyme was inactive.

Example 2

An EPSPS Gene Containing the N44D and P106L Mutations Confers Enhanced Tolerance to Glyphosate when Expressed in *Arabidopsis*

In the first example using the *E. coli* assay we have been able to show that the N44D mutation in itself provides tolerance to glyphosate, but when combined with e.g. the P106L mutation glyphosate tolerance is strongly enhanced. The aim of the present example is to demonstrate that the N44D mutation shows the same effect in plants and so the effect of a number of mutant EPSPS genes on glyphosate resistance in *Arabidopsis thaliana* was tested.

Constructing of Binary Vectors Containing Mutant EPSPS Genes

The mutated *Arabidopsis* EPSPS genes tested in *E. coli* (see Example 1) were cloned into the binary vector pEARLEYGATE100 (The Plant J. 2006; 45:616-629). Briefly, the EPSPS genes were isolated as BamHI and SacI fragments comprising the complete ORF's and then inserted into the same unique sites present in the binary vector. This resulted in a series of binary vectors carving a T-DNA on which the EPSPS genes are expressed by the constitutive 355 promoter and also carrying a BAR gene (conferring resistance to glufosinate) that can be used for plant selection. This series of binary vectors were electroporated to the *Agrobacterium tumefaciens* strain GV2260 and bacterial colonies were selected on LB medium containing 100 μg/ml spectinomycin, using methods known to the skilled person.

Transformation of *Arabidopsis thaliana*

Seeds of *Arabidopsis thaliana* (ecotype Colombia) were sown on soil and once germinated a single seedling was placed in a 5 cm×5 cm pot and allowed to grow until the first influorescence appeared. At this stage the plants were then transformed using the floral dip method. Briefly, the *Agrobacterium* strains were grown overnight in 50 ml liquid LB medium containing 100 μg/ml spectinomycin at 28° C. and then this culture was centrifuged at 4000 rpm for 10 minutes. The pellets were then resuspended in a 5% sucrose solution containing 0.02% Silwet (Lehle Seeds). The *Arabidopsis* plants were dipped into this culture and then incubated overnight in the dark at 25° C. The plants were then allowed to grow further in the greenhouse and after 7 days the dipping procedure was repeated. The plants were then allowed to set seed which was then germinated on soil. For selection of transformed *Arabidopsis* seedlings, a solution of glufosinate was prepared (0.1 mg/ml glufosinate ammonium+0.005% silwet) and sprayed on the seedlings. After 7 days the surviving seedlings were identified, grown to maturity and the seeds were collected.

Copy Number Determination of the Transgenic *Arabidopsis* Lines

We performed a segregation analysis on the seed of the transgenic lines to estimate the T-DNA copy number. Seed from each of the transgenic lines was sterilized with a 2% hypochlorite solution and washed with sterile water. Approximately 100 seeds per line were then placed on MS20 medium containing 0.1 mg/ml glufosinate ammonium and the number of surviving seedlings was scored after 20 days. The lines with a single T-DNA copy that segregated 31 (resistance:sensitivity) to the glufosinate were selected for further phenotyping.

Glyphosate Tolerance of the Transgenic *Arabidopsis* Lines

Seeds from the transgenic *Arabidopsis* lines were sterilized and then placed on MS20 medium containing 0.1 mg/ml glufosinate ammonium and +/−400 μM glyphosate and were grown for 4 weeks. After this period the seedlings were removed from the growth plates and the average seedling weight was determined. The degree of glyphosate resistance for each line was determined by dividing the average seedling weight in the presence of glyphosate by the average seedling weight found in the absence of glyphosate. The results of this analysis is shown in FIG. 23.

The data in plants, i.e. from *Arabidopsis* confirms the resistance that we found in the *E. coli* growth assays.

Overexpression of the EPSPS genes containing only the N44D mutation lead to glyphosate resistance as compared to the EPSPS unmutated WI form. Overexpression of the EPSPS P106L gene gave reasonable resistance, while this could be enhanced in the 3 independent lines expressing EPSPS with both the P106L and the N44D mutation. The data for the S179N mutation shows that the mutation also confers resistance when combined with N44D.

The invention claimed is:

1. A nucleotide sequence encoding a plant derived EPSPS enzyme that confers glyphosate resistance to a plant, characterized in that the nucleotide sequence comprises at least one mutation as compared with a corresponding wild type nucleotide sequence, wherein said mutation corresponds to a change into an Aspartic Acid or Glutamic Acid in the encoded EPSPS enzyme at a position corresponding to position 44 in SEQ ID NO: 5, and wherein the plant derived EPSPS enzyme has EPSPS enzymatic activity and comprises an amino acid sequence having at least 90% identity over its entire length with at least one amino acid sequence chosen from SEQ ID NO: 1, 2, 3, 4, 5, or 6.

2. An EPSPS enzyme that confers glyphosate resistance to a plant, encoded by the nucleotide sequence of claim 1.

3. A vector comprising a nucleotide sequence according to claim 1.

4. A host comprising the vector of claim 3.

5. A plant or part thereof comprising the nucleotide sequence of claim 1.

6. The plant or part thereof of claim 5, wherein the amino acid that is changed is Asparagine.

7. The plant or part thereof of claim 5, wherein the amino acid is changed into an Aspartic Acid.

8. The plant or part thereof of claim 5, wherein the nucleotide sequence comprises at least one further mutation that on its own renders said nucleotide sequence to encode an EPSPS enzyme that confers glyphosate resistance to a plant.

9. The plant or part thereof of claim 8, wherein the at least one further mutation corresponds to a change of an amino acid in the encoded EPSPS enzyme at a position corresponding to position 101, 106, or 179 in SEQ ID NO: 5.

10. The plant or part thereof of claim 9, wherein the amino acid that is changed corresponding to the position 101 is Glycine, the amino acid that is changed corresponding to the position 106 is Proline, and/or the amino acid that is changed corresponding to the position 179 is Serine.

11. The plant or part thereof of claim 9, wherein the amino acid corresponding to the position 101 is changed into an Alanine, the amino acid corresponding to the position 106 is changed into a Leucine, and/or the amino acid corresponding to the position 179 is changed into an Asparagine.

12. A seed derived from the plant or part thereof of claim 5.

13. A method for creating a plant with resistance to glyphosate, the method comprising:
a) providing a plant or plant cell that comprises a nucleotide sequence encoding a plant derived EPSPS enzyme, wherein the plant derived EPSPS enzyme has EPSPS enzymatic activity and comprises an amino acid sequence having at least 90% identity over its entire length with at least one amino acid sequence chosen from SEQ ID NO: 1, 2, 3, 4, 5, or 6; and
b) introducing at least one mutation as compared with a corresponding wild type nucleotide sequence into the nucleotide sequence, wherein said mutation corresponds to a change into an Aspartic Acid or Glutamic Acid in the encoded EPSPS enzyme at a position corresponding to position 44 in SEQ ID NO: 5.

14. The method of claim 13, wherein the at least one mutation is introduced into the nucleotide sequence by introducing at least one oligonucleotide capable of hybridizing to the nucleotide sequence into the plant or plant cell of step a), wherein the oligonucleotide comprises at least one mismatch with respect to the nucleotide sequence of step a), and wherein the mismatch is positioned in the oligonucleotide so that it causes the mutation of step b).

15. The method of claim 13, wherein the amino acid that is changed is Asparagine.

16. The method of claim 13, wherein the amino acid is changed into an Aspartic Acid.

17. A method for enhancing glyphosate resistance of a plant, the method comprising:
a) providing a plant or plant cell that comprises a nucleotide sequence encoding a plant derived EPSPS enzyme that confers glyphosate resistance to the plant or plant cell, wherein the plant derived EPSPS enzyme has EPSPS enzymatic activity and comprises an amino acid sequence having of at least 90% identity over its entire length with at least one amino acid sequence chosen from SEQ ID NO: 1, 2, 3, 4, 5, or 6; and
b) introducing at least one mutation as compared with a corresponding wild type nucleotide sequence into the nucleotide sequence, wherein said mutation corresponds to a change into an Aspartic Acid or Glutamic Acid in the encoded EPSPS enzyme at a position corresponding to position 44 in SEQ ID NO: 5.

18. The method of claim 17, wherein the nucleotide sequence of step a) comprises at least one mutation that corresponds to a change of an amino acid in the encoded EPSPS enzyme at a position corresponding to position 101, 106, or 179 in SEQ ID NO: 5.

19. The method of claim 17, wherein the at least one mutation is introduced into the nucleotide sequence in step b) by introducing at least one oligonucleotide capable of hybridizing to the nucleotide sequence into the plant or plant cell of step a), wherein the oligonucleotide comprises at least one mismatch with respect to the nucleotide sequence of step a), and wherein the mismatch is positioned in the oligonucleotide so that it causes the mutation of step b).

20. The method of claim 17, wherein the amino acid that is changed is Asparagine.

21. The method of claim 17, wherein the amino acid is changed into an Aspartic Acid.

22. The method of claim 18, wherein the amino acid that is changed corresponding to the position 101 is Glycine, the amino acid that is changed corresponding to the position 106 is Proline, and/or the amino acid that is changed corresponding to the position 179 is Serine.

23. The method of claim 18, wherein the amino acid corresponding to the position 101 is changed into an Alanine, the amino acid corresponding to the position 106 is changed into a Leucine, and/or the amino acid corresponding to the position 179 is changed into an Asparagine.

24. A plant product obtained by processing a plant, or a part thereof, created by the method of claim 13, wherein the processing comprises cooking, grinding, drying, milling, baking, cutting, sieving, flaking, peeling, soaking, washing, heating, cooling, crushing, or wetting.

25. A plant product obtained by processing a plant, or a part thereof, created by the method of claim 17, wherein the processing comprises cooking, grinding, drying, milling, baking, cutting, sieving, flaking, peeling, soaking, washing, heating, cooling, crushing, or wetting.

26. A method for creating a plant with resistance to glyphosate, the method comprising:
 a) providing a plant or plant cell;
 b) introducing the nucleotide sequence according to claim 1; and
 c) expressing the EPSPS enzyme encoded by the nucleotide sequence of step b) in the plant or plant cell.

27. The nucleotide sequence of claim 1, wherein the nucleotide sequence is a cDNA sequence.

28. The EPSPS enzyme of claim 2, wherein the amino acid that is changed is Asparagine.

29. The EPSPS enzyme of claim 2, wherein the amino acid is changed into an Aspartic Acid.

30. A plant product obtained by processing the plant, or a part thereof, of claim 5, wherein the processing comprises cooking, grinding, drying, milling, baking, cutting, sieving, flaking, peeling, soaking, washing, heating, cooling, crushing, or wetting.

* * * * *

```
                        SEQUENCE LISTING

<160> NUMBER OF SEQ ID NOS: 28

<210> SEQ ID NO 1
<211> LENGTH: 195
<212> TYPE: PRT
<213> ORGANISM: Maize

<400> SEQUENCE: 1

Ala Glu Glu Ile Val Leu Gln Pro Ile Lys Glu Ile Ser Gly Thr Val
1               5                   10                  15

Lys Leu Pro Gly Ser Lys Ser Leu Ser Asn Arg Ile Leu Leu Leu Ala
            20                  25                  30

Ala Leu Ser Glu Gly Thr Thr Val Val Asp Asn Leu Leu Asn Ser Glu
        35                  40                  45

Asp Val His Tyr Met Leu Gly Ala Leu Arg Thr Leu Gly Leu Ser Val
    50                  55                  60

Glu Ala Asp Lys Ala Ala Lys Arg Ala Val Val Val Gly Cys Gly Gly
65                  70                  75                  80

Lys Phe Pro Val Glu Asp Ala Lys Glu Glu Val Gln Leu Phe Leu Gly
                85                  90                  95

Asn Ala Gly Thr Ala Met Arg Pro Leu Thr Ala Ala Val Thr Ala Ala
            100                 105                 110

Gly Gly Asn Ala Thr Tyr Val Leu Asp Gly Val Pro Arg Met Arg Glu
        115                 120                 125

Arg Pro Ile Gly Asp Leu Val Val Gly Leu Lys Gln Leu Gly Ala Asp
    130                 135                 140

Val Asp Cys Phe Leu Gly Thr Asp Cys Pro Pro Val Arg Val Asn Gly
145                 150                 155                 160

Ile Gly Gly Leu Pro Gly Gly Lys Val Lys Leu Ser Gly Ser Ile Ser
                165                 170                 175

Ser Gln Tyr Leu Ser Ala Leu Leu Met Ala Ala Pro Leu Ala Leu Gly
            180                 185                 190

Asp Val Glu
        195

<210> SEQ ID NO 2
<211> LENGTH: 197
<212> TYPE: PRT
<213> ORGANISM: Rice

<400> SEQUENCE: 2

Lys Ala Glu Glu Ile Val Leu Gln Pro Ile Arg Glu Ile Ser Gly Ala
1               5                   10                  15

Val Gln Leu Pro Gly Ser Lys Ser Leu Ser Asn Arg Ile Leu Leu Leu
            20                  25                  30

Ser Ala Leu Ser Glu Gly Thr Thr Val Val Asp Asn Leu Leu Asn Ser
        35                  40                  45

Glu Asp Val His Tyr Met Leu Glu Ala Leu Lys Ala Leu Gly Leu Ser
    50                  55                  60

Val Glu Ala Asp Lys Val Ala Lys Arg Ala Val Val Val Gly Cys Gly
65                  70                  75                  80

Gly Lys Phe Pro Val Glu Lys Asp Ala Lys Glu Glu Val Gln Leu Phe
```

```
                        85                  90                  95
Leu Gly Asn Ala Gly Thr Ala Met Arg Pro Leu Thr Ala Ala Val Thr
                100                 105                 110

Ala Ala Gly Gly Asn Ala Thr Tyr Val Leu Asp Gly Val Pro Arg Met
            115                 120                 125

Arg Glu Arg Pro Ile Gly Asp Leu Val Val Gly Leu Lys Gln Leu Gly
        130                 135                 140

Ala Asp Val Asp Cys Phe Leu Gly Thr Glu Cys Pro Pro Val Arg Val
145                 150                 155                 160

Lys Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu
        195

<210> SEQ ID NO 3
<211> LENGTH: 197
<212> TYPE: PRT
<213> ORGANISM: Wheat

<400> SEQUENCE: 3

Gly Ala Glu Glu Val Val Leu Gln Pro Ile Arg Glu Ile Ser Gly Ala
1               5                   10                  15

Val Gln Leu Pro Gly Ser Lys Ser Leu Ser Asn Arg Ile Leu Leu Leu
            20                  25                  30

Ser Ala Leu Ser Glu Gly Thr Thr Val Val Asp Asn Leu Leu Asn Ser
        35                  40                  45

Glu Asp Val His Tyr Met Leu Glu Ala Leu Ala Leu Gly Leu Ser
    50                  55                  60

Val Glu Ala Asp Lys Val Ala Lys Arg Ala Val Val Val Gly Cys Gly
65                  70                  75                  80

Gly Arg Phe Pro Val Glu Lys Asp Ala Gln Glu Val Lys Leu Phe
                85                  90                  95

Leu Gly Asn Ala Gly Thr Ala Met Arg Pro Leu Thr Ala Ala Val Val
                100                 105                 110

Ala Ala Gly Gly Asn Ala Thr Tyr Val Leu Asp Gly Val Pro Arg Met
            115                 120                 125

Arg Glu Arg Pro Ile Gly Asp Leu Val Val Gly Leu Gln Gln Leu Gly
        130                 135                 140

Ala Asp Ala Asp Cys Phe Leu Gly Thr Asn Cys Pro Pro Val Arg Ile
145                 150                 155                 160

Asn Gly Lys Gly Gly Leu Pro Gly Gly Lys Val Lys Leu Ser Gly Ser
                165                 170                 175

Ile Ser Ser Gln Tyr Leu Ser Ser Leu Leu Met Ala Ala Pro Leu Ala
            180                 185                 190

Leu Glu Asp Val Glu
        195

<210> SEQ ID NO 4
<211> LENGTH: 197
<212> TYPE: PRT
<213> ORGANISM: Tomato
<220> FEATURE:
<221> NAME/KEY: misc_feature
<222> LOCATION: (8)..(8)
<223> OTHER INFORMATION: Xaa can be any naturally occurring amino acid
```

<400> SEQUENCE: 4

```
Lys Pro His Glu Ile Val Leu Xaa Pro Ile Lys Asp Ile Ser Gly Thr
1               5                   10                  15

Val Lys Leu Pro Gly Ser Lys Ser Leu Ser Asn Arg Ile Leu Leu Leu
            20                  25                  30

Ala Ala Leu Ser Glu Gly Arg Thr Val Val Asp Asn Leu Leu Ser Ser
        35                  40                  45

Asp Asp Ile His Tyr Met Leu Gly Ala Leu Lys Thr Leu Gly Leu His
    50                  55                  60

Val Glu Asp Asp Asn Glu Asn Gln Arg Ala Ile Val Glu Gly Cys Gly
65                  70                  75                  80

Gly Gln Phe Pro Val Gly Lys Lys Ser Glu Glu Ile Gln Leu Phe
            85                  90                  95

Leu Gly Asn Ala Gly Thr Ala Met Arg Pro Leu Thr Ala Ala Val Thr
            100                 105                 110

Val Ala Gly Gly His Ser Arg Tyr Val Leu Asp Gly Val Pro Arg Met
        115                 120                 125

Arg Glu Arg Pro Ile Gly Asp Leu Val Asp Gly Leu Lys Gln Leu Gly
    130                 135                 140

Ala Glu Val Asp Cys Ser Leu Gly Thr Asn Cys Pro Pro Val Arg Ile
145                 150                 155                 160

Val Ser Lys Gly Gly Leu Pro Gly Gly Lys Val Lys Leu Ser Gly Ser
            165                 170                 175

Ile Ser Ser Gln Tyr Leu Thr Ala Leu Leu Met Ala Ala Pro Leu Ala
            180                 185                 190

Leu Gly Asp Val Glu
        195
```

<210> SEQ ID NO 5
<211> LENGTH: 197
<212> TYPE: PRT
<213> ORGANISM: Arabidopsis

<400> SEQUENCE: 5

```
Lys Ala Ser Glu Ile Val Leu Gln Pro Ile Arg Glu Ile Ser Gly Leu
1               5                   10                  15

Ile Lys Leu Pro Gly Ser Lys Ser Leu Ser Asn Arg Ile Leu Leu Leu
            20                  25                  30

Ala Ala Leu Ser Glu Gly Thr Thr Val Val Asp Asn Leu Leu Asn Ser
        35                  40                  45

Asp Asp Ile Asn Tyr Met Leu Asp Ala Leu Lys Arg Leu Gly Leu Asn
    50                  55                  60

Val Glu Thr Asp Ser Glu Asn Asn Arg Ala Val Val Glu Gly Cys Gly
65                  70                  75                  80

Gly Ile Phe Pro Ala Ser Ile Asp Ser Lys Ser Asp Ile Glu Leu Tyr
            85                  90                  95

Leu Gly Asn Ala Gly Thr Ala Met Arg Pro Leu Thr Ala Ala Val Thr
            100                 105                 110

Ala Ala Gly Gly Asn Ala Ser Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Glu Cys Thr Leu Gly Thr Asn Cys Pro Pro Val Arg Val
145                 150                 155                 160
```

Asn Ala Asn Gly Gly Leu Pro Gly Gly Lys Val Lys Leu Ser Gly Ser
            165                 170                 175

Ile Ser Ser Gln Tyr Leu Thr Ala Leu Leu Met Ser Ala Pro Leu Ala
            180                 185                 190

Leu Gly Asp Val Glu
        195

<210> SEQ ID NO 6
<211> LENGTH: 183
<212> TYPE: PRT
<213> ORGANISM: Onion

<400> SEQUENCE: 6

Gly Thr Val Asn Leu Pro Gly Ser Lys Ser Leu Ser Asn Arg Ile Leu
1               5                   10                  15

Leu Leu Ala Ala Leu Ala Glu Gly Thr Thr Val Val Asp Asn Leu Leu
            20                  25                  30

Asn Ser Asp Asp Val Ser Tyr Met Leu Ala Ala Leu Lys Thr Leu Gly
        35                  40                  45

Leu Ser Val Glu Asp Asp Arg Met Asn Lys Arg Ala Ile Val Val Gly
    50                  55                  60

Ser Gly Gly Leu Phe Pro Val Gly Lys Glu Ser Gln Val Glu Val Gln
65                  70                  75                  80

Leu Phe Leu Gly Asn Ala Gly Thr Ala Met Arg Pro Leu Thr Ala Ala
                85                  90                  95

Val Thr Ala Ala Gly Gly Asn Ala Ser Tyr Ile Leu Asp Gly Val Pro
            100                 105                 110

Arg Met Arg Glu Arg Pro Ile Gly Asp Leu Val Val Gly Leu Lys Gln
        115                 120                 125

Leu Gly Ala Asp Val Asp Cys Thr Leu Gly Thr Asp Cys Pro Pro Arg
    130                 135                 140

Val Arg Asn Ala Asn Gly Gly Leu Pro Gly Gly Lys Val Lys Leu Ser
145                 150                 155                 160

Gly Ser Ile Ser Ser Gln Tyr Leu Thr Ala Leu Leu Met Ala Ala Pro
                165                 170                 175

Leu Ala Leu Gly Asp Val Glu
            180

<210> SEQ ID NO 7
<211> LENGTH: 187
<212> TYPE: PRT
<213> ORGANISM: Salmonella

<400> SEQUENCE: 7

Glu Ser Leu Thr Leu Gln Pro Ile Ala Arg Val Asp Gly Ala Ile Asn
1               5                   10                  15

Leu Pro Gly Ser Lys Ser Val Ser Asn Arg Ala Leu Leu Leu Ala Ala
            20                  25                  30

Leu Pro Cys Gly Lys Thr Ala Leu Thr Asn Leu Leu Asp Ser Asp Asp
        35                  40                  45

Val Arg His Met Leu Asn Ala Leu Ser Ala Leu Gly Ile Asn Tyr Thr
    50                  55                  60

Leu Ser Ala Asp Arg Thr Arg Cys Asp Ile Thr Gly Asn Gly Gly Ala
65                  70                  75                  80

Leu Arg Ala Pro Gly Ala Leu Glu Leu Phe Leu Gly Asn Ala Gly Thr
                85                  90                  95

Ala Met Arg Pro Leu Ala Ala Ala Leu Cys Leu Gly Gln Asn Glu Ile
            100                 105                 110

Val Leu Thr Gly Glu Pro Arg Met Lys Glu Arg Pro Ile Gly His Leu
            115                 120                 125

Val Asp Ser Leu Arg Gln Gly Gly Ala Asn Ile Asp Tyr Leu Glu Gln
130                 135                 140

Glu Asn Tyr Pro Pro Leu Arg Leu Arg Gly Gly Phe Thr Gly Gly Asp
145                 150                 155                 160

Ile Glu Val Asp Gly Ser Val Ser Ser Gln Phe Leu Thr Ala Leu Leu
                165                 170                 175

Met Thr Ala Pro Leu Ala Pro Lys Asp Thr Ile
            180                 185

<210> SEQ ID NO 8
<211> LENGTH: 187
<212> TYPE: PRT
<213> ORGANISM: E. coli

<400> SEQUENCE: 8

Glu Ser Leu Thr Leu Gln Pro Ile Ala Arg Val Asp Gly Thr Ile Asn
1               5                   10                  15

Leu Pro Gly Ser Lys Ser Val Ser Asn Arg Ala Leu Leu Leu Ala Ala
            20                  25                  30

Leu Ala His Gly Lys Thr Val Leu Thr Asn Leu Leu Asp Ser Asp Asp
        35                  40                  45

Val Arg His Met Leu Asn Ala Leu Thr Gly Leu Gly Val Ser Tyr Thr
    50                  55                  60

Leu Ser Ala Asp Arg Thr Arg Cys Glu Ile Ile Gly Asn Gly Gly Pro
65                  70                  75                  80

Leu His Ala Glu Gly Ala Leu Glu Leu Phe Leu Gly Asn Ala Gly Thr
                85                  90                  95

Ala Met Arg Pro Leu Ala Ala Ala Leu Cys Leu Gly Ser Asn Asp Ile
            100                 105                 110

Val Leu Thr Gly Glu Pro Arg Met Lys Glu Arg Pro Ile Gly His Leu
            115                 120                 125

Val Asp Ala Leu Arg Leu Gly Gly Ala Lys Ile Thr Tyr Leu Glu Gln
130                 135                 140

Glu Asn Tyr Pro Pro Leu Arg Leu Gln Gly Gly Phe Thr Gly Gly Asn
145                 150                 155                 160

Val Asp Val Asp Gly Ser Val Ser Ser Gln Phe Leu Thr Ala Leu Leu
                165                 170                 175

Met Thr Ala Pro Leu Ala Pro Glu Asp Thr Val
            180                 185

<210> SEQ ID NO 9
<211> LENGTH: 520
<212> TYPE: PRT
<213> ORGANISM: Arabidopsis thaliana

<400> SEQUENCE: 9

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

-continued

Trp Gly Leu Lys Lys Ser Gly Met Thr Leu Ile Gly Ser Glu Leu Arg
 50                  55                  60

Pro Leu Lys Val Met Ser Ser Val Ser Thr Ala Glu Lys Ala Ser Glu
 65                  70                  75                  80

Ile Val Leu Gln Pro Ile Arg Glu Ile Ser Gly Leu Ile Lys Leu Pro
                 85                  90                  95

Gly Ser Lys Ser Leu Ser Asn Arg Ile Leu Leu Ala Ala Leu Ser
            100                 105                 110

Glu Gly Thr Thr Val Val Asp Asn Leu Leu Asn Ser Asp Asp Ile Asn
            115                 120                 125

Tyr Met Leu Asp Ala Leu Lys Arg Leu Gly Leu Asn Val Glu Thr Asp
130                 135                 140

Ser Glu Asn Asn Arg Ala Val Val Gly Cys Gly Gly Ile Phe Pro
145                 150                 155                 160

Ala Ser Ile Asp Ser Lys Ser Asp Ile Glu Leu Tyr Leu Gly Asn Ala
                165                 170                 175

Gly Thr Ala Met Arg Pro Leu Thr Ala Ala Val Thr Ala Ala Gly Gly
            180                 185                 190

Asn Ala Ser Tyr Val Leu Asp Gly Val Pro Arg Met Arg Glu Arg Pro
            195                 200                 205

Ile Gly Asp Leu Val Val Gly Leu Lys Gln Leu Gly Ala Asp Val Glu
210                 215                 220

Cys Thr Leu Gly Thr Asn Cys Pro Pro Val Arg Val Asn Ala Asn Gly
225                 230                 235                 240

Gly Leu Pro Gly Gly Lys Val Lys Leu Ser Gly Ser Ile Ser Ser Gln
                245                 250                 255

Tyr Leu Thr Ala Leu Leu Met Ser Ala Pro Leu Ala Leu Gly Asp Val
            260                 265                 270

Glu Ile Glu Ile Val Asp Lys Leu Ile Ser Val Pro Tyr Val Glu Met
            275                 280                 285

Thr Leu Lys Leu Met Glu Arg Phe Gly Val Ser Val Glu His Ser Asp
290                 295                 300

Ser Trp Asp Arg Phe Phe Val Lys Gly Gly Gln Lys Tyr Lys Ser Pro
305                 310                 315                 320

Gly Asn Ala Tyr Val Glu Gly Asp Ala Ser Ser Ala Ser Tyr Phe Leu
                325                 330                 335

Ala Gly Ala Ala Ile Thr Gly Glu Thr Val Thr Val Glu Gly Cys Gly
            340                 345                 350

Thr Thr Ser Leu Gln Gly Asp Val Lys Phe Ala Glu Val Leu Glu Lys
            355                 360                 365

Met Gly Cys Lys Val Ser Trp Thr Glu Asn Ser Val Thr Val Thr Gly
370                 375                 380

Pro Pro Arg Asp Ala Phe Gly Met Arg His Leu Arg Ala Ile Asp Val
385                 390                 395                 400

Asn Met Asn Lys Met Pro Asp Val Ala Met Thr Leu Ala Val Val Ala
                405                 410                 415

Leu Phe Ala Asp Gly Pro Thr Thr Ile Arg Asp Val Ala Ser Trp Arg
            420                 425                 430

Val Lys Glu Thr Glu Arg Met Ile Ala Ile Cys Thr Glu Leu Arg Lys
            435                 440                 445

Leu Gly Ala Thr Val Glu Glu Gly Ser Asp Tyr Cys Val Ile Thr Pro
450                 455                 460

```
Pro Lys Lys Val Lys Thr Ala Glu Ile Asp Thr Tyr Asp Asp His Arg
465                 470                 475                 480

Met Ala Met Ala Phe Ser Leu Ala Ala Cys Ala Asp Val Pro Ile Thr
            485                 490                 495

Ile Asn Asp Pro Gly Cys Thr Arg Lys Thr Phe Pro Asp Tyr Phe Gln
        500                 505                 510

Val Leu Glu Arg Ile Thr Lys His
        515                 520

<210> SEQ ID NO 10
<211> LENGTH: 1560
<212> TYPE: DNA
<213> ORGANISM: Arabidopsis thaliana

<400> SEQUENCE: 10
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcggagaa agcgtcggag     240
attgtacttc aacccattag agaaatctcc ggtcttatta gcttcctgg ctccaagtct      300 ctatcaaatc gaatcctgct tctcgctgct ctgtctgagg aacaactgt agtggacaac      360 ttgttgaata gcgatgacat caattacatg cttgatgcgt tgaagagatt gggacttaat     420
gtggaaactg acagtgaaaa taatcgtgct gtagttgaag atgtggcgg atattccca       480 gcttccatag attcaaagag tgatatcgaa ctttacctcg gtaatgcagg aacagcaatg     540
cgtccactta ccgctgcggt cactgctgca ggtggaaacg caagttatgt gcttgatggg     600
gtgcctcgta tgagagaaag acctataggg gatttggttg ttggtcttaa gcagcttggt     660
gctgatgttg aatgtactct tggaactaac tgccctcctg ttcgtgtcaa cgctaatggt     720
ggccttcccg gtggaaaggt gaagcttct ggatcaatta gtagtcagta cttgactgct      780
ctgctcatgt ctgctccctt agctcttgga gacgtcgaga ttgagattgt cgataaatta     840
atttctgttc catatgttga atgacattg aagttgatgg aacgtttcgg ggttagtgtc      900
gagcatagtg atagctggga tcgtttcttt gtcaagggcg ggcaaaaata caagtctccg     960
ggtaatgcgt atgtagaagg tgatgcttct agtgctagtt atttcttggc tggtgctgcc    1020
attaccggtg aaactgtcac agtcgaaggt tgtggaacta ccagcttgca gggagatgta    1080
aaattcgccg aggtccttga gaaaatggga tgtaaagtgt cctggacaga gaacagtgtg    1140
actgtgacag gaccacctag agatgctttt ggaatgagac acttgcgggc tattgatgtc    1200
aacatgaaca aaatgcctga tgtagccatg acccttgccg tcgttgctct ctttgctgac    1260
ggtccaacca ccattagaga tgtggctagc tggagagtaa aggagacaga aaggatgatt    1320
gccatttgca cagagcttag aaaactggga gctacagtgg aagaaggttc agattattgt    1380
gtgataactc cgcccaaaaa ggtgaaaacg gcagagattg atacatatga tgatcataga    1440
atggcaatgg cattctctct tgcagcttgt gctgatgttc caatcaccat caacgatcct    1500
ggttgcacca ggaaaacctt ccccgactac ttccaagtac ttgaaagaat cacaaagcac    1560

<210> SEQ ID NO 11
<211> LENGTH: 1560
<212> TYPE: DNA
<213> ORGANISM: Arabidopsis thaliana

<400> SEQUENCE: 11
```

| | |
|---|---|
| atggcgcaag ttagcagaat ctgcaatggt gtgcagaacc catctcttat ctccaatctc | 60 |
| tcgaaatcca gtcaacgcaa atctccctta tcggtttctc tgaagacgca gcagcatcca | 120 |
| cgagcttatc cgatttcgtc gtcgtgggga ttgaagaaga gtgggatgac gttaattggc | 180 |
| tctgagcttc gtcctcttaa ggtcatgtct tctgtttcca cggcggagaa agcgtcggag | 240 |
| attgtacttc aacccattag agaaatctcc ggtcttatta agcttcctgg ctccaagtct | 300 |
| ctatcaaatc gaatcctgct tctcgctgct ctgtctgagg aacaactgt agtggacgac | 360 |
| ttgttgaata gcgatgacat caattacatg cttgatgcgt tgaagagatt gggacttaat | 420 |
| gtggaaactg acagtgaaaa taatcgtgct gtagttgaag gatgtggcgg gatattccca | 480 |
| gcttccatag attcaaagag tgatatcgaa ctttacctcg gtaatgcagg aacagcaatg | 540 |
| cgtccactta ccgctgcggt cactgctgca ggtggaaacg caagttatgt gcttgatggg | 600 |
| gtgcctcgta tgagagaaag acctataggg gatttggttg ttggtcttaa gcagcttggt | 660 |
| gctgatgttg aatgtactct tggaactaac tgccctcctg ttcgtgtcaa cgctaatggt | 720 |
| ggccttcccg gtggaaaggt gaagctttct ggatcaatta gtagtcagta cttgactgct | 780 |
| ctgctcatgt ctgctccctt agctcttgga gacgtcgaga ttgagattgt cgataaatta | 840 |
| atttctgttc catatgttga atgacattg aagttgatgg aacgtttcgg ggttagtgtc | 900 |
| gagcatagtg atagctggga tcgtttcttt gtcaagggcg ggcaaaaata caagtctccg | 960 |
| ggtaatgcgt atgtagaagg tgatgcttct agtgctagtt atttcttggc tggtgctgcc | 1020 |
| attaccggtg aaactgtcac agtcgaaggt tgtggaacta ccagcttgca gggagatgta | 1080 |
| aaattcgccg aggtccttga gaaaatggga tgtaaagtgt cctggacaga gaacagtgtg | 1140 |
| actgtgacag gaccacctag agatgctttt ggaatgagac acttgcgggc tattgatgtc | 1200 |
| aacatgaaca aaatgcctga tgtagccatg acccttgccg tcgttgctct ctttgctgac | 1260 |
| ggtccaacca ccattagaga tgtggctagc tgggagtaa aggagacaga aaggatgatt | 1320 |
| gccatttgca cagagcttag aaaactggga gctacagtgg aagaaggttc agattattgt | 1380 |
| gtgataactc cgcccaaaaa ggtgaaaacg gcagagattg atacatatga tgatcataga | 1440 |
| atggcaatgg cattctctct tgcagcttgt gctgatgttc caatcaccat caacgatcct | 1500 |
| ggttgcacca ggaaaaacctt ccccgactac ttccaagtac ttgaaagaat cacaaagcac | 1560 |

<210> SEQ ID NO 12
<211> LENGTH: 1560
<212> TYPE: DNA
<213> ORGANISM: Arabidopsis thaliana

<400> SEQUENCE: 12

| | |
|---|---|
| atggcgcaag ttagcagaat ctgcaatggt gtgcagaacc catctcttat ctccaatctc | 60 |
| tcgaaatcca gtcaacgcaa atctccctta tcggtttctc tgaagacgca gcagcatcca | 120 |
| cgagcttatc cgatttcgtc gtcgtgggga ttgaagaaga gtgggatgac gttaattggc | 180 |
| tctgagcttc gtcctcttaa ggtcatgtct tctgtttcca cggcggagaa agcgtcggag | 240 |
| attgtacttc aacccattag agaaatctcc ggtcttatta agcttcctgg ctccaagtct | 300 |
| ctatcaaatc gaatcctgct tctcgctgct ctgtctgagg aacaactgt agtggacaac | 360 |
| ttgttgaata gcgatgacat caattacatg cttgatgcgt tgaagagatt gggacttaat | 420 |
| gtggaaactg acagtgaaaa taatcgtgct gtagttgaag gatgtggcgg gatattccca | 480 |
| gcttccatag attcaaagag tgatatcgaa ctttacctcg gtaatgcagg aacagcaatg | 540 |

-continued

```
cgtctactta ccgctgcggt cactgctgca ggtggaaacg caagttatgt gcttgatggg      600
gtgcctcgta tgagagaaag acctataggg gatttggttg ttggtcttaa gcagcttggt      660
gctgatgttg aatgtactct tggaactaac tgccctcctg ttcgtgtcaa cgctaatggt      720
ggccttcccg gtggaaaggt gaagctttct ggatcaatta gtagtcagta cttgactgct      780
ctgctcatgt ctgctccctt agctcttgga gacgtcgaga ttgagattgt cgataaatta      840
atttctgttc catatgttga atgacattg aagttgatgg aacgtttcgg ggttagtgtc      900
gagcatagtg atagctggga tcgtttcttt gtcaagggcg ggcaaaaata caagtctccg      960
ggtaatgcgt atgtagaagg tgatgcttct agtgctagtt atttcttggc tggtgctgcc     1020
attaccggtg aaactgtcac agtcgaaggt tgtggaacta ccagcttgca gggagatgta     1080
aaattcgccg aggtccttga gaaaatggga tgtaaagtgt cctggacaga aacagtgtg      1140 actgtgacag gaccacctag agatgctttt ggaatgagac acttgcgggc tattgatgtc     1200
aacatgaaca aaatgcctga tgtagccatg acccttgccg tcgttgctct ctttgctgac     1260
ggtccaacca ccattagaga tgtggctagc tggagagtaa aggagacaga aaggatgatt     1320
gccatttgca cagagcttag aaaactggga gctacagtgg aagaaggttc agattattgt     1380
gtgataactc cgcccaaaaa ggtgaaaacg gcagagatta tacatatga tgatcataga      1440 atggcaatgg cattctctct tgcagcttgt gctgatgttc caatcaccat caacgatcct     1500
ggttgcacca ggaaaacctt ccccgactac ttccaagtac ttgaaagaat cacaaagcac     1560
```

<210> SEQ ID NO 13
<211> LENGTH: 1560
<212> TYPE: DNA
<213> ORGANISM: Arabidopsis thaliana

<400> SEQUENCE: 13

```
atggcgcaag ttagcagaat ctgcaatggt gtgcagaacc catctcttat ctccaatctc       60
tcgaaatcca gtcaacgcaa atctccctta tcggtttctc tgaagacgca gcagcatcca      120
cgagcttatc cgatttcgtc gtcgtgggga ttgaagaaga gtgggatgac gttaattggc      180
tctgagcttc gtcctcttaa ggtcatgtct tctgttccca cggcggagaa agcgtcggag      240
attgtacttc aacccattag agaaatctcc ggtcttatta agcttcctgg ctccaagtct      300
ctatcaaatc gaatcctgct tctcgctgct ctgtctgagg gaacaactgt agtggacgac      360 tgttgaata gcgatgacat caattacatg cttgatgcgt tgaagagatt gggacttaat      420
gtggaaactg acagtgaaaa taatcgtgct gtagttgaag gatgtggcgg gatattccca      480
gcttccatag attcaaagag tgatatcgaa ctttacctcg gtaatgcagg aacagcaatg      540
cgtctactta ccgctgcggt cactgctgca ggtggaaacg caagttatgt gcttgatggg      600
gtgcctcgta tgagagaaag acctataggg gatttggttg ttggtcttaa gcagcttggt      660
gctgatgttg aatgtactct tggaactaac tgccctcctg ttcgtgtcaa cgctaatggt      720
ggccttcccg gtggaaaggt gaagctttct ggatcaatta gtagtcagta cttgactgct      780
ctgctcatgt ctgctccctt agctcttgga gacgtcgaga ttgagattgt cgataaatta      840
atttctgttc catatgttga atgacattg aagttgatgg aacgtttcgg ggttagtgtc      900
gagcatagtg atagctggga tcgtttcttt gtcaagggcg ggcaaaaata caagtctccg      960
ggtaatgcgt atgtagaagg tgatgcttct agtgctagtt atttcttggc tggtgctgcc     1020
attaccggtg aaactgtcac agtcgaaggt tgtggaacta ccagcttgca gggagatgta     1080
aaattcgccg aggtccttga gaaaatggga tgtaaagtgt cctggacaga aacagtgtg      1140
```

```
actgtgacag gaccacctag agatgctttt ggaatgagac acttgcgggc tattgatgtc    1200
aacatgaaca aaatgcctga tgtagccatg acccttgccg tcgttgctct ctttgctgac    1260
ggtccaacca ccattagaga tgtggctagc tggagagtaa aggagacaga aaggatgatt    1320
gccatttgca cagagcttag aaaactggga gctacagtgg aagaaggttc agattattgt    1380
gtgataactc cgcccaaaaa ggtgaaaacg gcagagattg atacatatga tgatcataga    1440
atggcaatgg cattctctct tgcagcttgt gctgatgttc caatcaccat caacgatcct    1500
ggttgcacca ggaaaaacctt ccccgactac ttccaagtac ttgaaagaat cacaaagcac    1560
```

<210> SEQ ID NO 14
<211> LENGTH: 1560
<212> TYPE: DNA
<213> ORGANISM: Arabidopsis thaliana

<400> SEQUENCE: 14

```
atggcgcaag ttagcagaat ctgcaatggt gtgcagaacc catctcttat ctccaatctc      60
tcgaaatcca gtcaacgcaa atctccctta tcggtttctc tgaagacgca gcagcatcca    120
cgagcttatc cgatttcgtc gtcgtgggga ttgaagaaga gtgggatgac gttaattggc    180
tctgagcttc gtcctcttaa ggtcatgtct tctgtttcca cggcggagaa agcgtcggag    240
attgtacttc aacccattag agaaatctcc ggtcttatta agcttcctgg ctccaagtct    300
ctatcaaatc gaatcctgct tctcgctgct ctgtctgagg aacaactgt agtggacaac    360 ttgttgaata gcgatgacat caattacatg cttgatgcgt tgaagagatt gggacttaat    420
gtggaaactg acagtgaaaa taatcgtgct gtagttgaag gatgtggcgg atattccca    480 gcttccatag attcaaagag tgatatcgaa ctttacctcg gtaatgcagg aacagcaatg    540
cgtccactta ccgctgcggt cactgctgca ggtggaaacg caagttatgt gcttgatggg    600
gtgcctcgta tgagagaaag acctataggg gatttggttg ttggtcttaa gcagcttggt    660
gctgatgttg aatgtactct tggaactaac tgccctcctg ttcgtgtcaa cgctaatggt    720
ggccttcccg gtggaaaggt gaagcttttc ggatcaatta gtaatcagta cttgactgct    780
ctgctcatgt ctgctccctt agctcttgga gacgtcgaga ttgagattgt cgataaatta    840
atttctgttc catatgttga aatgacattg aagttgatgg aacgtttcgg ggttagtgtc    900
gagcatagtg atagctggga tcgtttcttt gtcaagggcg ggcaaaaata caagtctccg    960
ggtaatgcgt atgtagaagg tgatgcttct agtgctagtt atttcttggc tggtgctgcc   1020
attaccggtg aaactgtcac agtcgaaggt tgtggaacta ccagcttgca gggagatgta   1080
aaattcgccg aggtccttga aaaatggga tgtaaagtgt cctggacaga aacagtgtg   1140 actgtgacag gaccacctag agatgctttt ggaatgagac acttgcgggc tattgatgtc   1200
aacatgaaca aaatgcctga tgtagccatg acccttgccg tcgttgctct ctttgctgac   1260
ggtccaacca ccattagaga tgtggctagc tggagagtaa aggagacaga aaggatgatt   1320
gccatttgca cagagcttag aaaactggga gctacagtgg aagaaggttc agattattgt   1380
gtgataactc cgcccaaaaa ggtgaaaacg gcagagattg atacatatga tgatcataga   1440
atggcaatgg cattctctct tgcagcttgt gctgatgttc caatcaccat caacgatcct   1500
ggttgcacca ggaaaaacctt ccccgactac ttccaagtac ttgaaagaat cacaaagcac   1560
```

<210> SEQ ID NO 15
<211> LENGTH: 1560
<212> TYPE: DNA

<213> ORGANISM: Arabidopsis thaliana

<400> SEQUENCE: 15

```
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcggagaa agcgtcggag     240
attgtacttc aacccattag agaaatctcc ggtcttatta agcttcctgg ctccaagtct     300
ctatcaaatc gaatcctgct ctcgctgct ctgtctgagg aacaactgt agtggacaac       360
ttgttgaata gcgatgacat caattacatg cttgatgcgt tgaagagatt gggacttaat     420
gtggaaactg acagtgaaaa taatcgtgct gtagttgaag gatgtggcgg gatattccca     480
gcttccatag attcaaagag tgatatcgaa ctttacctcg gtaatgcagg aacagcaatg     540
cgtctactta ccgctgcggt cactgctgca gtgggaaacg caagttatgt gcttgatggg     600
gtgcctcgta tgagagaaag acctataggg gatttggttg ttggtcttaa gcagcttggt     660
gctgatgttg aatgtactct tggaactaac tgccctcctg ttcgtgtcaa cgctaatggt     720
ggccttcccg gtggaaaggt gaagcttcct ggatcaatta gtaatcagta cttgactgct     780
ctgctcatgt ctgctccctt agctcttgga gacgtcgaga ttgagattgt cgataaatta     840
atttctgttc catatgttga atgacattg aagttgatgg aacgtttcgg ggttagtgtc      900
gagcatagtg atagctggga tcgttttcttt gtcaagggcg ggcaaaaata caagtctccg    960
ggtaatgcgt atgtagaagg tgatgcttct agtgctagtt atttcttggc tggtgctgcc   1020
attaccggtg aaactgtcac agtcgaaggt tgtggaacta ccagcttgca gggagatgta   1080
aaattcgccg aggtccttga aaaatggga tgtaaagtgt cctggacaga gaacagtgtg    1140
actgtgacag gaccacctag agatgctttt ggaatgagac acttgcgggc tattgatgtc   1200
aacatgaaca aaatgcctga tgtagccatg acccttgccg tcgttgctct ctttgctgac   1260
ggtccaacca ccattagaga tgtggctagc tggagagtaa aggagacaga aaggatgatt   1320
gccatttgca cagagcttag aaaactggga gctacagtgg aagaaggttc agattattgt   1380
gtgataactc cgcccaaaaa ggtgaaaacg gcagagattg atacatatga tgatcataga   1440
atggcaatgg cattctctct tgcagcttgt gctgatgttc caatcaccat caacgatcct   1500
ggttgcacca ggaaaacctt ccccgactac ttccaagtac ttgaaagaat cacaaagcac   1560
```

<210> SEQ ID NO 16
<211> LENGTH: 1560
<212> TYPE: DNA
<213> ORGANISM: Arabidopsis thaliana

<400> SEQUENCE: 16

```
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcggagaa agcgtcggag     240
attgtacttc aacccattag agaaatctcc ggtcttatta agcttcctgg ctccaagtct     300
ctatcaaatc gaatcctgct ctcgctgct ctgtctgagg aacaactgt agtggacgac       360
ttgttgaata gcgatgacat caattacatg cttgatgcgt tgaagagatt gggacttaat     420
gtggaaactg acagtgaaaa taatcgtgct gtagttgaag gatgtggcgg gatattccca     480
```

```
gcttccatag attcaaagag tgatatcgaa ctttacctcg gtaatgcagg aacagcaatg      540
cgtccactta ccgctgcggt cactgctgca ggtggaaacg caagttatgt gcttgatggg      600
gtgcctcgta tgagagaaag acctataggg gatttggttg ttggtcttaa gcagcttggt      660
gctgatgttg aatgtactct tggaactaac tgccctcctg ttcgtgtcaa cgctaatggt      720
ggccttcccg gtggaaaggt gaagctttct ggatcaatta gtaatcagta cttgactgct      780
ctgctcatgt ctgctccctt agctcttgga gacgtcgaga ttgagattgt cgataaatta      840
atttctgttc catatgttga aatgacattg aagttgatgg aacgtttcgg ggttagtgtc      900
gagcatagtg atagctggga tcgtttcttt gtcaagggcg ggcaaaaata caagtctccg      960
ggtaatgcgt atgtagaagg tgatgcttct agtgctagtt atttcttggc tggtgctgcc     1020
attaccggta aaactgtcac agtcgaaggt tgtggaacta ccagcttgca gggagatgta     1080
aaattcgccg aggtccttga aaaatgggga tgtaaagtgt cctggacaga aacagtgtg      1140 actgtgacag gaccacctag agatgctttt ggaatgagac acttgcgggc tattgatgtc     1200
aacatgaaca aaatgcctga tgtagccatg acccttgccg tcgttgctct ctttgctgac     1260
ggtccaacca ccattagaga tgtggctagc tggagagtaa aggagacaga aaggatgatt     1320
gccatttgca cagagcttag aaaactggga gctacagtgg aagaaggttc agattattgt     1380
gtgataactc cgcccaaaaa ggtgaaaacg gcagagattg atacatatga tgatcataga     1440
atggcaatgg cattctctct tgcagcttgt gctgatgttc caatcaccat caacgatcct     1500
ggttgcacca ggaaaacctt ccccgactac ttccaagtac ttgaaagaat cacaaagcac     1560
```

<210> SEQ ID NO 17
<211> LENGTH: 1560
<212> TYPE: DNA
<213> ORGANISM: Arabidopsis thaliana

<400> SEQUENCE: 17

```
atggcgcaag ttagcagaat ctgcaatggt gtgcagaacc catctcttat ctccaatctc       60
tcgaaatcca gtcaacgcaa atctcccttc tcggtttctc tgaagacgca gcagcatcca      120
cgagcttatc cgatttcgtc gtcgtgggga ttgaagaaga gtgggatgac gttaattggc      180
tctgagcttc gtcctcttaa ggtcatgtct tctgtttcca cggcggagaa agcgtcggag      240
attgtacttc aacccattag agaaatctcc ggtcttatta gcttcctgg ctccaagtct       300 ctatcaaatc gaatcctgct tctcgctgct ctgtctgagg aacaactgt agtggacaac       360 ttgttgaata gcgatgacat caattacatg cttgatgcgt tgaagagatt gggacttaat      420
gtggaaactg acagtgaaaa taatcgtgct gtagttgaag gatgtggcgg gatattccca      480
gcttccatag attcaaagag tgatatcgaa ctttacctcg gtaatgcagc aacagcaatg      540
cgtccactta ccgctgcggt cactgctgca ggtggaaacg caagttatgt gcttgatggg      600
gtgcctcgta tgagagaaag acctataggg gatttggttg ttggtcttaa gcagcttggt      660
gctgatgttg aatgtactct tggaactaac tgccctcctg ttcgtgtcaa cgctaatggt      720
ggccttcccg gtggaaaggt gaagctttct ggatcaatta gtagtcagta cttgactgct      780
ctgctcatgt ctgctccctt agctcttgga gacgtcgaga ttgagattgt cgataaatta      840
atttctgttc catatgttga aatgacattg aagttgatgg aacgtttcgg ggttagtgtc      900
gagcatagtg atagctggga tcgtttcttt gtcaagggcg ggcaaaaata caagtctccg      960
ggtaatgcgt atgtagaagg tgatgcttct agtgctagtt atttcttggc tggtgctgcc     1020
```

```
attaccggtg aaactgtcac agtcgaaggt tgtggaacta ccagcttgca gggagatgta    1080
aaattcgccg aggtccttga gaaaatggga tgtaaagtgt cctggacaga gaacagtgtg    1140
actgtgacag gaccacctag agatgctttt ggaatgagac acttgcgggc tattgatgtc    1200
aacatgaaca aaatgcctga tgtagccatg acccttgccg tcgttgctct ctttgctgac    1260
ggtccaacca ccattagaga tgtggctagc tggagagtaa aggagacaga aaggatgatt    1320
gccatttgca cagagcttag aaaactggga gctacagtgg aagaaggttc agattattgt    1380
gtgataactc cgcccaaaaa ggtgaaaacg gcagagattg atacatatga tgatcataga    1440
atggcaatgg cattctctct tgcagcttgt gctgatgttc caatcaccat caacgatcct    1500
ggttgcacca ggaaaacctt ccccgactac ttccaagtac ttgaaagaat cacaaagcac    1560
```

<210> SEQ ID NO 18
<211> LENGTH: 1560
<212> TYPE: DNA
<213> ORGANISM: Arabidopsis thaliana

<400> SEQUENCE: 18

```
atggcgcaag ttagcagaat ctgcaatggt gtgcagaacc catctcttat ctccaatctc      60
tcgaaatcca gtcaacgcaa atctccctta tcggtttctc tgaagacgca gcagcatcca    120
cgagcttatc cgatttcgtc gtcgtgggga ttgaagaaga gtgggatgac gttaattggc    180
tctgagcttc gtcctcttaa ggtcatgtct ctgtttccca cggcggagaa agcgtcggag    240
attgtacttc aacccattag agaaatctcc ggtcttatta agcttcctgg ctccaagtct    300
ctatcaaatc gaatcctgct ctcgctgct ctgtctgagg aacaactgt agtggacgac     360 ttgttgaata gcgatgacat caattacatg cttgatgcgt tgaagagatt gggacttaat    420
gtggaaactg acagtgaaaa taatcgtgct gtagttgaag gatgtggcgg atattccca     480 gcttccatag attcaaagag tgatatcgaa ctttacctcg gtaatgcagc aacagcaatg    540
cgtccactta ccgctgcggt cactgctgca ggtggaaacg caagttatgt gcttgatggg    600
gtgcctcgta tgagagaaag acctataggg gatttggttg ttggtcttaa gcagcttggt    660
gctgatgttg aatgtactct tggaactaac tgccctcctg ttcgtgtcaa cgctaatggt    720
ggccttcccg gtggaaaggt gaagcttct ggatcaatta gtagtcagta cttgactgct    780
ctgctcatgt ctgctccctt agctcttgga gacgtcgaga ttgagattgt cgataaatta    840
atttctgttc catatgttga atgacattg aagttgatgg aacgtttcgg ggttagtgtc    900
gagcatagtg atagctggga tcgtttcttt gtcaagggcg ggcaaaaata caagtctccg    960
ggtaatgcgt atgtagaagg tgatgcttct agtgctagtt atttcttggc tggtgctgcc   1020
attaccggtg aaactgtcac agtcgaaggt tgtggaacta ccagcttgca gggagatgta   1080
aaattcgccg aggtccttga gaaaatggga tgtaaagtgt cctggacaga gaacagtgtg   1140
actgtgacag gaccacctag agatgctttt ggaatgagac acttgcgggc tattgatgtc   1200
aacatgaaca aaatgcctga tgtagccatg acccttgccg tcgttgctct ctttgctgac   1260
ggtccaacca ccattagaga tgtggctagc tggagagtaa aggagacaga aaggatgatt   1320
gccatttgca cagagcttag aaaactggga gctacagtgg aagaaggttc agattattgt   1380
gtgataactc cgcccaaaaa ggtgaaaacg gcagagattg atacatatga tgatcataga   1440
atggcaatgg cattctctct tgcagcttgt gctgatgttc caatcaccat caacgatcct   1500
ggttgcacca ggaaaacctt ccccgactac ttccaagtac ttgaaagaat cacaaagcac   1560
```

<210> SEQ ID NO 19
<211> LENGTH: 1557
<212> TYPE: DNA
<213> ORGANISM: Tomato

<400> SEQUENCE: 19

```
atggcacaga ttagcaaaat gacacagggg atacaaaccc tttatcccaa ttccaagatt      60
cataaacccc aagttcccac atttctccct tcacttcctt ttggatctaa aaacctgaaa     120
aaatcagtaa aatgtttgtg ggttttgaat aaagattcag ttttgacaac aaggtcttgt     180
tcttcttctt ttaggatttc agcatcagtg ctacaaccc agaaaccttc tgagattgtg      240
ctgcaaccca tcaaagaaat tcaggcact gtcaaattgc caggctctaa atctctatcc      300
aatcgtatcc tccttctggc tgctctatct gaaggaacaa ctgtggttga caatttgcta     360
agtagtgatg atattcatta catgcttggt gcgttgaaaa cacttggact gcaagtagaa     420
gatgacagtg aaaccaaca agctgttgtt gaaggttgtg gtggtttgtt ccctgccgct     480
aaagagtcca aggaagagat tcaacttttc cttggaaatg caggaactgc aatgcggcca     540
ctaacagcag cagttgctgt agctggcgga aattcaaggt atgtacttga tggagttcct     600
cgaatgagag agaccaat tagtgatttg gttgatggtc ttaagcagct tggtgcagag     660
gttgattgtt ccttggtac gaaatgtcct cctgttcgaa ttgtcagcaa gggaggtctc     720
ccaggaggga aggtgaagct gtctggatcc attagcagcc aatacttgac tgctctgctt     780
atggctgctc cactggcttt aggagatgtg gagattgaaa tcattgacaa actaatatct     840
gtaccttatg tcgaaatgac tttgaagttg atggagcgat ttggtatatc tgtggagcac     900
aatagtagct gggacaggtt cttgtccga ggaggtcaga atacaagtc tcctggaaaa     960
gcttatgtgg aaggtgatgc ttcaagtgct agttacttct tggctggtgc agctgtcaca    1020
ggtggaacca tcactgttga aggttgtgga acaaacagtt tacaggggga tgtcaaattt    1080
gctgaggttc ttgagaaaat gggagcagaa gttacatgga cagagaatag cgtcacagtt    1140
aaaggacctc caaggaattc ttctggaagg aagcatttgc atgccattga tgtgaacatg    1200
aataaaatgc ctgatgtcgc catgacactt gctgtagttg cacttttgc tgacggtccc    1260
actgctataa gagacgttgc tagttggaga gtcaaggaaa ctgagcgcat gatcgccata    1320
tgcacagaac ttaggaagtt gggagcaact gttgaagaag acctgacta ctgcataatc    1380
accccaccgg agaaattaaa tgtgaccgaa attgatacat atgacgatca caggatggcc    1440
atggcctttt ctcttgctgc ttgtgcagat gttccagtca ccatcaatga ccctggctgc    1500
acgcggaaaa ccttcccaaa ctactttgat gtccttcagc agtactccaa gcattga      1557
```

<210> SEQ ID NO 20
<211> LENGTH: 1533
<212> TYPE: DNA
<213> ORGANISM: Tomato

<400> SEQUENCE: 20

```
gattagtagc atggcacaag ggatacagac ccttagtctg aattcctcca atctttctaa      60
aacacaaaag ggtcctcttg tttcaaattc tctcttcttt ggatcaaaga aagtaaccca    120
aatttcagca aaatcattag gggtgtttaa gaaagattca gttttgaggg tggtgaggaa    180
gtcatctttt aggatttctg catcagtggc tactgcagag aaaccccatg agattgtgct    240
agaacccatc aaagatatat ctggtactgt taaattaccc ggttcgaaat ccctttccaa    300
tcgtattctc cttcttgctg cccttttctga gggaaggact gttgttgaca atttactgag    360
```

-continued

```
tagtgacgac attcattaca tgcttggtgc gttgaaaaca cttggacttc atgttgaaga     420
tgacaatgaa aaccaacgag caattgtgga aggttgtggt gggcagtttc ctgtcggtaa     480
aaagtctgag gaagaaatcc aactattcct tggaaatgca ggaacagcaa tgcgtccgtt     540
gacagcagca gttactgtag ctggaggaca ttcaagatat gttcttgatg agttccctag     600
gatgagagag agaccaattg tgatttggt tgatggtctt aagcagcttg cgcagaggt     660 agattgttcc cttggtacga attgtccccc agttcgaatt gtcagcaagg aggtcttcc     720 aggagggaag gtaaagctct ctggatccat cagcagccaa tacctgactg ctctgcttat     780
ggctgctccc ctggctctag agatgtgga gattgaaata attgacaaac tgatatctgt     840
gccttatgtt gaaatgacac tgaagttgat ggagcgattt ggtgtctttg tggagcacag     900
tagtggctgg acagattct tggtaaaagg aggtcagaag tacaaatctc ctgggaaagc     960
atttgttgaa ggagatgcct caagtgctag ctatttttg gcgggggcag cagtcacagg    1020
tggaaccgtc actgttgaag gttgtggaac aagcagttta cagggagatg ttaagttcgc    1080
tgaggtcctc gagaagatgg gggcagaagt tacatggaca gagaacagtg tcacagttaa    1140
aggacctccg aggaactctt ctggaatgaa acatttgcgt gccattgacg tgaacatgaa    1200
caaaatgcca gatgtggcca tgactcttgc cgtagttgca ctttttgctg atggtcctac    1260
taccataaga gacgttgcta gctggagagt aaaggaaact gagcggatga ttgccatatg    1320
caccgaactt aggaagttgg gtgcaacagt tgttgaaggg tcagactact gcataatcac    1380
cccaccagaa aagttaaacg taacggagat tgatacatat gatgaccaca gaatggctat    1440
ggctttctct cttgctgctt gtgctgatgt tccagtcact attaaggacc ctggctgtac    1500
tcgcaaaacc ttcccccgact acttcgaggt tct                                 1533
```

<210> SEQ ID NO 21
<211> LENGTH: 518
<212> TYPE: PRT
<213> ORGANISM: Tomato

<400> SEQUENCE: 21

Met Ala Gln Ile Ser Lys Met Thr Gln Gly Ile Gln Thr Leu Tyr Pro
1               5                   10                  15

Asn Ser Lys Ile His Lys Pro Gln Val Pro Thr Phe Leu Pro Ser Leu
                20                  25                  30

Pro Phe Gly Ser Lys Asn Leu Lys Ser Val Lys Cys Leu Trp Val
            35                  40                  45

Leu Asn Lys Asp Ser Val Leu Thr Thr Arg Ser Cys Ser Ser Phe
50                  55                  60

Arg Ile Ser Ala Ser Val Ala Thr Thr Gln Lys Pro Ser Glu Ile Val
65                  70                  75                  80

Leu Gln Pro Ile Lys Glu Ile Ser Gly Thr Val Lys Leu Pro Gly Ser
                85                  90                  95

Lys Ser Leu Ser Asn Arg Ile Leu Leu Leu Ala Ala Leu Ser Glu Gly
                100                 105                 110

Thr Thr Val Val Asp Asn Leu Leu Ser Ser Asp Asp Ile His Tyr Met
            115                 120                 125

Leu Gly Ala Leu Lys Thr Leu Gly Leu Gln Val Glu Asp Asp Ser Gly
        130                 135                 140

Asn Gln Gln Ala Val Val Glu Gly Cys Gly Gly Leu Phe Pro Ala Ala
145                 150                 155                 160

Lys Glu Ser Lys Glu Glu Ile Gln Leu Phe Leu Gly Asn Ala Gly Thr

```
            165                 170                 175
Ala Met Arg Pro Leu Thr Ala Val Ala Val Ala Gly Gly Asn Ser
            180                 185                 190

Arg Tyr Val Leu Asp Gly Val Pro Arg Met Arg Glu Arg Pro Ile Ser
            195                 200                 205

Asp Leu Val Asp Gly Leu Lys Gln Leu Gly Ala Glu Val Asp Cys Phe
210                 215                 220

Leu Gly Thr Lys Cys Pro Pro Val Arg Ile Val Ser Lys Gly Gly Leu
225                 230                 235                 240

Pro Gly Gly Lys Val Lys Leu Ser Gly Ser Ile Ser Ser Gln Tyr Leu
                245                 250                 255

Thr Ala Leu Leu Met Ala Ala Pro Leu Ala Leu Gly Asp Val Glu Ile
                260                 265                 270

Glu Ile Ile Asp Lys Leu Ile Ser Val Pro Tyr Val Glu Met Thr Leu
                275                 280                 285

Lys Leu Met Glu Arg Phe Gly Ile Ser Val Glu His Asn Ser Ser Trp
                290                 295                 300

Asp Arg Phe Phe Val Arg Gly Gly Gln Lys Tyr Lys Ser Pro Gly Lys
305                 310                 315                 320

Ala Tyr Val Glu Gly Asp Ala Ser Ser Ala Ser Tyr Phe Leu Ala Gly
                325                 330                 335

Ala Ala Val Thr Gly Gly Thr Ile Thr Val Glu Gly Cys Gly Thr Asn
                340                 345                 350

Ser Leu Gln Gly Asp Val Lys Phe Ala Glu Val Leu Glu Lys Met Gly
                355                 360                 365

Ala Glu Val Thr Trp Thr Glu Asn Ser Val Thr Val Lys Gly Pro Pro
                370                 375                 380

Arg Asn Ser Ser Gly Arg Lys His Leu His Ala Ile Asp Val Asn Met
385                 390                 395                 400

Asn Lys Met Pro Asp Val Ala Met Thr Leu Ala Val Val Ala Leu Phe
                405                 410                 415

Ala Asp Gly Pro Thr Ala Ile Arg Asp Val Ala Ser Trp Arg Val Lys
                420                 425                 430

Glu Thr Glu Arg Met Ile Ala Ile Cys Thr Glu Leu Arg Lys Leu Gly
                435                 440                 445

Ala Thr Val Glu Glu Gly Pro Asp Tyr Cys Ile Ile Thr Pro Pro Glu
                450                 455                 460

Lys Leu Asn Val Thr Glu Ile Asp Thr Tyr Asp Asp His Arg Met Ala
465                 470                 475                 480

Met Ala Phe Ser Leu Ala Ala Cys Ala Asp Val Pro Val Thr Ile Asn
                485                 490                 495

Asp Pro Gly Cys Thr Arg Lys Thr Phe Pro Asn Tyr Phe Asp Val Leu
                500                 505                 510

Gln Gln Tyr Ser Lys His
            515

<210> SEQ ID NO 22
<211> LENGTH: 520
<212> TYPE: PRT
<213> ORGANISM: Tomato

<400> SEQUENCE: 22

Met Ala Gln Ile Ser Ser Met Ala Gln Gly Ile Gln Thr Leu Ser Leu
1               5                   10                  15
```

-continued

Asn Ser Ser Asn Leu Ser Lys Thr Gln Lys Gly Pro Leu Val Ser Asn
            20                  25                  30

Ser Leu Phe Phe Gly Ser Lys Lys Val Thr Gln Ile Ser Ala Lys Ser
        35                  40                  45

Leu Gly Val Phe Lys Lys Asp Ser Val Leu Arg Val Arg Lys Ser
    50                  55                  60

Ser Phe Arg Ile Ser Ala Ser Val Ala Thr Ala Glu Lys Pro His Glu
65                  70                  75                  80

Ile Val Leu Glu Pro Ile Lys Asp Ile Ser Gly Thr Val Lys Leu Pro
                85                  90                  95

Gly Ser Lys Ser Leu Ser Asn Arg Ile Leu Leu Ala Ala Leu Ser
                100                 105                 110

Glu Gly Arg Thr Val Val Asp Asn Leu Leu Ser Ser Asp Ile His
                115                 120                 125

Tyr Met Leu Gly Ala Leu Lys Thr Leu Gly Leu His Val Glu Asp Asp
    130                 135                 140

Asn Glu Asn Gln Arg Ala Ile Val Glu Gly Cys Gly Gly Gln Phe Pro
145                 150                 155                 160

Val Gly Lys Lys Ser Glu Glu Glu Ile Gln Leu Phe Leu Gly Asn Ala
                165                 170                 175

Gly Thr Ala Met Arg Pro Leu Thr Ala Ala Val Thr Val Ala Gly Gly
            180                 185                 190

His Ser Arg Tyr Val Leu Asp Gly Val Pro Arg Met Arg Glu Arg Pro
            195                 200                 205

Ile Gly Asp Leu Val Asp Gly Leu Lys Gln Leu Gly Ala Glu Val Asp
210                 215                 220

Cys Ser Leu Gly Thr Asn Cys Pro Pro Val Arg Ile Val Ser Lys Gly
225                 230                 235                 240

Gly Leu Pro Gly Gly Lys Val Lys Leu Ser Gly Ser Ile Ser Ser Gln
                245                 250                 255

Tyr Leu Thr Ala Leu Leu Met Ala Ala Pro Leu Ala Leu Gly Asp Val
            260                 265                 270

Glu Ile Glu Ile Ile Asp Lys Leu Ile Ser Val Pro Tyr Val Glu Met
            275                 280                 285

Thr Leu Lys Leu Met Glu Arg Phe Gly Val Phe Val Glu His Ser Ser
    290                 295                 300

Gly Trp Asp Arg Phe Leu Val Lys Gly Gly Gln Lys Tyr Lys Ser Pro
305                 310                 315                 320

Gly Lys Ala Phe Val Glu Gly Asp Ala Ser Ser Ala Ser Tyr Phe Leu
                325                 330                 335

Ala Gly Ala Ala Val Thr Gly Gly Thr Val Thr Val Glu Gly Cys Gly
            340                 345                 350

Thr Ser Ser Leu Gln Gly Asp Val Lys Phe Ala Glu Val Leu Glu Lys
    355                 360                 365

Met Gly Ala Glu Val Thr Trp Thr Glu Asn Ser Val Thr Val Lys Gly
    370                 375                 380

Pro Pro Arg Asn Ser Ser Gly Met Lys His Leu Arg Ala Ile Asp Val
385                 390                 395                 400

Asn Met Asn Lys Met Pro Asp Val Ala Met Thr Leu Ala Val Val Ala
                405                 410                 415

Leu Phe Ala Asp Gly Pro Thr Thr Ile Arg Asp Val Ala Ser Trp Arg
            420                 425                 430

Val Lys Glu Thr Glu Arg Met Ile Ala Ile Cys Thr Glu Leu Arg Lys

```
                    435                 440                 445
Leu Gly Ala Thr Val Val Glu Gly Ser Asp Tyr Cys Ile Ile Thr Pro
            450                 455                 460

Pro Glu Lys Leu Asn Val Thr Glu Ile Asp Thr Tyr Asp Asp His Arg
465                 470                 475                 480

Met Ala Met Ala Phe Ser Leu Ala Ala Cys Ala Asp Val Pro Val Thr
                485                 490                 495

Ile Lys Asp Pro Gly Cys Thr Arg Lys Thr Phe Pro Asp Tyr Phe Glu
            500                 505                 510

Val Leu Gln Lys Tyr Ser Lys His
            515                 520

<210> SEQ ID NO 23
<211> LENGTH: 427
<212> TYPE: PRT
<213> ORGANISM: E. coli

<400> SEQUENCE: 23

Met Glu Ser Leu Thr Leu Gln Pro Ile Ala Arg Val Asp Gly Thr Ile
1               5                   10                  15

Asn Leu Pro Gly Ser Lys Ser Val Ser Asn Arg Ala Leu Leu Leu Ala
            20                  25                  30

Ala Leu Ala His Gly Lys Thr Val Leu Thr Asn Leu Leu Asp Ser Asp
        35                  40                  45

Asp Val Arg His Met Leu Asn Ala Leu Thr Gly Leu Gly Val Ser Tyr
    50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
        115                 120                 125

Leu Val Asp Ala Leu Arg Leu Gly Gly Ala Lys Ile Thr Tyr Leu Glu
    130                 135                 140

Gln Glu Asn Tyr Pro Pro Leu Arg Leu Gln Gly Gly Phe Thr Gly Gly
145                 150                 155                 160

Asn Val Asp Val Asp Gly Ser Val Ser Ser Gln Phe Leu Thr Ala Leu
                165                 170                 175

Leu Met Thr Ala Pro Leu Ala Pro Glu Asp Thr Val Ile Arg Ile Lys
            180                 185                 190

Gly Asp Leu Val Ser Lys Pro Tyr Ile Asp Ile Thr Leu Asn Leu Met
        195                 200                 205

Lys Thr Phe Gly Val Glu Ile Glu Asn Gln His Tyr Gln Gln Phe Val
    210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285
```

```
Trp Gly Asp Asp Tyr Ile Ser Cys Thr Arg Gly Glu Leu Asn Ala Ile
    290             295                 300
Asp Met Asp Met Asn His Ile Pro Asp Ala Ala Met Thr Ile Ala Thr
305             310                 315                 320
Ala Ala Leu Phe Ala Lys Gly Thr Thr Thr Leu Arg Asn Ile Tyr Asn
                325                 330                 335
Trp Arg Val Lys Glu Thr Asp Arg Leu Phe Ala Met Ala Thr Glu Leu
                340                 345                 350
Arg Lys Val Gly Ala Glu Val Glu Gly His Asp Tyr Ile Arg Ile
        355                 360                 365
Thr Pro Pro Glu Lys Leu Asn Phe Ala Glu Ile Ala Thr Tyr Asn Asp
370                 375                 380
His Arg Met Ala Met Cys Phe Ser Leu Val Ala Leu Ser Asp Thr Pro
385                 390                 395                 400
Val Thr Ile Leu Asp Pro Lys Cys Thr Ala Lys Thr Phe Pro Asp Tyr
                405                 410                 415
Phe Glu Gln Leu Ala Arg Ile Ser Gln Ala Ala
                420                 425

<210> SEQ ID NO 24
<211> LENGTH: 521
<212> TYPE: PRT
<213> ORGANISM: Cotton

<400> SEQUENCE: 24

Met Ala Thr Gln Val Gly Lys Ile Tyr Asn Gly Thr Gln Lys Thr Cys
1               5                   10                  15
Val Leu Pro Asn Val Ser Lys Thr Gln Asn Pro Lys His Val Pro Phe
                20                  25                  30
Val Ser Phe Lys Ser Asn Leu Asn Gly Lys Thr Ser Ser Trp Gly Leu
            35                  40                  45
Val Val Lys Asn Asn Gly Lys Phe Gly Ser Ile Lys Ala Arg Ser Leu
        50                  55                  60
Lys Val Ser Ala Ser Thr Ala Thr Ala Glu Lys Pro Ser Arg Ala Ser
65                  70                  75                  80
Glu Ile Val Leu Gln Pro Ile Asn Glu Ile Ser Gly Thr Val Lys Leu
                85                  90                  95
Pro Gly Ser Lys Ser Leu Ser Asn Arg Ile Leu Leu Leu Ala Ala Leu
                100                 105                 110
Ser Glu Gly Thr Thr Val Val Glu Asn Leu Leu Asn Ser Asp Asp Val
            115                 120                 125
His His Met Leu Val Ala Leu Gly Lys Leu Gly Leu Tyr Val Lys His
        130                 135                 140
Asp Ser Glu Lys Lys Gln Ala Ile Val Glu Gly Cys Gly Gly Gln Phe
145                 150                 155                 160
Pro Val Gly Lys Gly Glu Gly Gln Glu Ile Glu Leu Phe Leu Gly Asn
                165                 170                 175
Ala Gly Thr Ala Met Arg Pro Leu Thr Ala Ala Ile Thr Ala Ala Gly
                180                 185                 190
Gly Asn Ser Ser Tyr Val Leu Asp Gly Val Pro Arg Met Arg Glu Arg
            195                 200                 205
Pro Ile Gly Asp Leu Val Thr Gly Leu Lys Gln Leu Gly Ala Asp Val
        210                 215                 220
Asp Cys Ile Leu Gly Thr Asn Cys Pro Pro Val Arg Ile Glu Gly Lys
225                 230                 235                 240
```

-continued

Gly Gly Leu Pro Gly Gly Lys Val Lys Leu Ser Gly Ser Ile Ser Ser
                245                 250                 255

Gln Tyr Leu Thr Ala Leu Leu Met Ala Ala Pro Leu Ala Leu Gly Asp
            260                 265                 270

Val Glu Ile Glu Ile Ile Asp Lys Leu Ile Ser Ile Pro Tyr Val Glu
        275                 280                 285

Met Thr Met Lys Leu Met Glu Arg Phe Gly Val Thr Val Glu His Thr
290                 295                 300

Asp Ser Trp Asp Arg Phe Phe Ile Arg Gly Gly Gln Lys Tyr Met Ser
305                 310                 315                 320

Pro Gly Asn Ala Tyr Val Glu Gly Asp Ala Ser Ser Ala Ser Tyr Phe
                325                 330                 335

Leu Ala Gly Ala Ala Val Thr Gly Gly Thr Val Thr Val Glu Gly Cys
            340                 345                 350

Gly Thr Ser Ser Leu Gln Gly Asp Val Lys Phe Ala Glu Val Leu Glu
        355                 360                 365

Met Met Gly Ala Lys Val Thr Trp Thr Glu Asn Ser Val Thr Val Thr
370                 375                 380

Gly Pro Pro Arg Asn Ser Ser Gly Arg Lys His Leu Arg Ala Ile Asp
385                 390                 395                 400

Val Asn Met Asn Lys Met Pro Asp Val Ala Met Thr Leu Ala Val Val
                405                 410                 415

Ala Leu Tyr Ala Asp Gly Pro Thr Ala Ile Arg Asp Val Ala Ser Trp
            420                 425                 430

Arg Val Lys Glu Thr Glu Arg Met Ile Ala Ile Cys Thr Glu Leu Arg
        435                 440                 445

Lys Leu Gly Ala Thr Val Glu Glu Gly Pro Asp Tyr Cys Val Ile Thr
450                 455                 460

Pro Pro Glu Lys Leu Asn Val Thr Ala Ile Asp Thr Tyr Asp Asp His
465                 470                 475                 480

Arg Met Ala Met Ala Phe Ser Leu Ala Ala Cys Ala Glu Val Pro Val
                485                 490                 495

Thr Ile Lys Asp Pro Gly Cys Thr Arg Lys Thr Phe Pro Asp Tyr Phe
            500                 505                 510

Glu Val Leu Asp Arg Val Thr Lys His
        515                 520

<210> SEQ ID NO 25
<211> LENGTH: 445
<212> TYPE: PRT
<213> ORGANISM: Maize

<400> SEQUENCE: 25

Met Ala Gly Ala Glu Glu Ile Val Leu Gln Pro Ile Lys Glu Ile Ser
1               5                   10                  15

Gly Thr Val Lys Leu Pro Gly Ser Lys Ser Leu Ser Asn Arg Ile Leu
            20                  25                  30

Leu Leu Ala Ala Leu Ser Glu Gly Thr Thr Val Val Asp Asn Leu Leu
        35                  40                  45

Asn Ser Glu Asp Val His Tyr Met Leu Gly Ala Leu Arg Thr Leu Gly
    50                  55                  60

Leu Ser Val Glu Ala Asp Lys Ala Ala Lys Arg Ala Val Val Val Gly
65                  70                  75                  80

Cys Gly Gly Lys Phe Pro Val Glu Asp Ala Lys Glu Glu Val Gln Leu

```
            85                  90                  95
Phe Leu Gly Asn Ala Gly Thr Ala Met Arg Pro Leu Thr Ala Val
            100                 105                 110
Thr Ala Ala Gly Gly Asn Ala Thr Tyr Val Leu Asp Gly Val Pro Arg
            115                 120                 125
Met Arg Glu Arg Pro Ile Gly Asp Leu Val Val Gly Leu Lys Gln Leu
            130                 135                 140
Gly Ala Asp Val Asp Cys Phe Leu Gly Thr Asp Cys Pro Pro Val Arg
145                 150                 155                 160
Val Asn Gly Ile Gly Gly Leu Pro Gly Gly Lys Val Lys Leu Ser Gly
            165                 170                 175
Ser Ile Ser Ser Gln Tyr Leu Ser Ala Leu Leu Met Ala Ala Pro Leu
            180                 185                 190
Ala Leu Gly Asp Val Glu Ile Glu Ile Ile Asp Lys Leu Ile Ser Ile
            195                 200                 205
Pro Tyr Val Glu Met Thr Leu Arg Leu Met Glu Arg Phe Gly Val Lys
            210                 215                 220
Ala Glu His Ser Asp Ser Trp Asp Arg Phe Tyr Ile Lys Gly Gly Gln
225                 230                 235                 240
Lys Tyr Lys Ser Pro Lys Asn Ala Tyr Val Glu Gly Asp Ala Ser Ser
            245                 250                 255
Ala Ser Tyr Phe Leu Ala Gly Ala Ala Ile Thr Gly Gly Thr Val Thr
            260                 265                 270
Val Glu Gly Cys Gly Thr Thr Ser Leu Gln Gly Asp Val Lys Phe Ala
            275                 280                 285
Glu Val Leu Glu Met Met Gly Ala Lys Val Thr Trp Thr Glu Thr Ser
            290                 295                 300
Val Thr Val Thr Gly Pro Pro Arg Glu Pro Phe Gly Arg Lys His Leu
305                 310                 315                 320
Lys Ala Ile Asp Val Asn Met Asn Lys Met Pro Asp Val Ala Met Thr
            325                 330                 335
Leu Ala Val Val Ala Leu Phe Ala Asp Gly Pro Thr Ala Ile Arg Asp
            340                 345                 350
Val Ala Ser Trp Arg Val Lys Glu Thr Glu Arg Met Val Ala Ile Arg
            355                 360                 365
Thr Glu Leu Thr Lys Leu Gly Ala Ser Val Glu Glu Gly Pro Asp Tyr
            370                 375                 380
Cys Ile Ile Thr Pro Pro Glu Lys Leu Asn Val Thr Ala Ile Asp Thr
385                 390                 395                 400
Tyr Asp Asp His Arg Met Ala Met Ala Phe Ser Leu Ala Ala Cys Ala
            405                 410                 415
Glu Val Pro Val Thr Ile Arg Asp Pro Gly Cys Thr Arg Lys Thr Phe
            420                 425                 430
Pro Asp Tyr Phe Asp Val Leu Ser Thr Phe Val Lys Asn
            435                 440                 445

<210> SEQ ID NO 26
<211> LENGTH: 515
<212> TYPE: PRT
<213> ORGANISM: Rice

<400> SEQUENCE: 26

Met Ala Ala Thr Met Ala Ser Asn Ala Ala Ala Ala Ala Val Ser
1               5                   10                  15
```

-continued

```
Leu Asp Gln Ala Val Ala Ala Ser Ala Ala Phe Ser Ser Arg Lys Gln
             20                  25                  30

Leu Arg Leu Pro Ala Ala Arg Gly Gly Met Arg Val Arg Val Arg
         35                  40                  45

Ala Arg Gly Arg Arg Glu Ala Val Val Ala Ser Ala Ser Ser Ser
     50                  55                  60

Ser Val Ala Ala Pro Ala Ala Lys Ala Glu Glu Ile Val Leu Gln Pro
 65                  70                  75                  80

Ile Arg Glu Ile Ser Gly Ala Val Gln Leu Pro Gly Ser Lys Ser Leu
                 85                  90                  95

Ser Asn Arg Ile Leu Leu Leu Ser Ala Leu Ser Glu Gly Thr Thr Val
            100                 105                 110

Val Asp Asn Leu Leu Asn Ser Glu Asp Val His Tyr Met Leu Glu Ala
        115                 120                 125

Leu Lys Ala Leu Gly Leu Ser Val Glu Ala Asp Lys Val Ala Lys Arg
    130                 135                 140

Ala Val Val Val Gly Cys Gly Gly Lys Phe Pro Val Glu Lys Asp Ala
145                 150                 155                 160

Lys Glu Glu Val Gln Leu Phe Leu Gly Asn Ala Gly Thr Ala Met Arg
                165                 170                 175

Pro Leu Thr Ala Ala Val Thr Ala Ala Gly Gly Asn Ala Thr Tyr Val
            180                 185                 190

Leu Asp Gly Val Pro Arg Met Arg Glu Arg Pro Ile Gly Asp Leu Val
        195                 200                 205

Val Gly Leu Lys Gln Leu Gly Ala Asp Val Asp Cys Phe Leu Gly Thr
    210                 215                 220

Glu Cys Pro Pro Val Arg Val Lys Gly Ile Gly Gly Leu Pro Gly Gly
225                 230                 235                 240

Lys Val Lys Leu Ser Gly Ser Ile Ser Ser Gln Tyr Leu Ser Ala Leu
                245                 250                 255

Leu Met Ala Ala Pro Leu Ala Leu Gly Asp Val Glu Ile Glu Ile Ile
            260                 265                 270

Asp Lys Leu Ile Ser Ile Pro Tyr Val Glu Met Thr Leu Arg Leu Met
        275                 280                 285

Glu Arg Phe Gly Val Lys Ala Glu His Ser Asp Ser Trp Asp Arg Phe
    290                 295                 300

Tyr Ile Lys Gly Gly Gln Lys Tyr Lys Ser Pro Gly Asn Ala Tyr Val
305                 310                 315                 320

Glu Gly Asp Ala Ser Ser Ala Ser Tyr Phe Leu Ala Gly Ala Ala Ile
                325                 330                 335

Thr Gly Gly Thr Val Thr Val Gln Gly Cys Gly Thr Thr Ser Leu Gln
            340                 345                 350

Gly Asp Val Lys Phe Ala Glu Val Leu Glu Met Met Gly Ala Lys Val
        355                 360                 365

Thr Trp Thr Asp Thr Ser Val Thr Val Thr Gly Pro Pro Arg Glu Pro
    370                 375                 380

Tyr Gly Lys Lys His Leu Lys Ala Val Asp Val Asn Met Asn Lys Met
385                 390                 395                 400

Pro Asp Val Ala Met Thr Leu Ala Val Val Ala Leu Phe Ala Asp Gly
                405                 410                 415

Pro Thr Ala Ile Arg Asp Val Ala Ser Trp Arg Val Lys Glu Thr Glu
            420                 425                 430

Arg Met Val Ala Ile Arg Thr Glu Leu Thr Lys Leu Gly Ala Ser Val
```

```
            435                 440                 445
Glu Glu Gly Pro Asp Tyr Cys Ile Ile Thr Pro Pro Glu Lys Leu Asn
    450                 455                 460

Ile Thr Ala Ile Asp Thr Tyr Asp Asp His Arg Met Ala Met Ala Phe
465                 470                 475                 480

Ser Leu Ala Ala Cys Ala Asp Val Pro Val Thr Ile Arg Asp Pro Gly
                485                 490                 495

Cys Thr Arg Lys Thr Phe Pro Asn Tyr Phe Asp Val Leu Ser Thr Phe
                500                 505                 510

Val Arg Asn
        515

<210> SEQ ID NO 27
<211> LENGTH: 510
<212> TYPE: PRT
<213> ORGANISM: Wheat

<400> SEQUENCE: 27

Met Ala Met Ala Ala Ala Ala Thr Met Ala Ala Ser Ala Ser Ser Ser
1               5                   10                  15

Ala Val Ser Leu Asp Arg Ala Ala Pro Ala Pro Ser Arg Arg Leu Pro
                20                  25                  30

Met Pro Ala Ala Arg Pro Ala Arg Arg Gly Ala Val Arg Leu Trp Gly
            35                  40                  45

Pro Arg Gly Ala Ala Ala Arg Ala Thr Ser Val Ala Ala Pro Ala Ala
50                  55                  60

Pro Ser Gly Ala Glu Glu Val Val Leu Gln Pro Ile Arg Glu Ile Ser
65                  70                  75                  80

Gly Ala Val Gln Leu Pro Gly Ser Lys Ser Leu Ser Asn Arg Ile Leu
                85                  90                  95

Leu Leu Ser Ala Leu Ser Glu Gly Thr Thr Val Val Asp Asn Leu Leu
            100                 105                 110

Asn Ser Glu Asp Val His Tyr Met Leu Glu Ala Leu Glu Ala Leu Gly
        115                 120                 125

Leu Ser Val Glu Ala Asp Lys Val Ala Lys Arg Ala Val Val Val Gly
    130                 135                 140

Cys Gly Gly Arg Phe Pro Val Glu Lys Asp Ala Gln Glu Glu Val Lys
145                 150                 155                 160

Leu Phe Leu Gly Asn Ala Gly Thr Ala Met Arg Pro Leu Thr Ala Ala
                165                 170                 175

Val Val Ala Ala Gly Gly Asn Ala Thr Tyr Val Leu Asp Gly Val Pro
            180                 185                 190

Arg Met Arg Glu Arg Pro Ile Gly Asp Leu Val Val Gly Leu Gln Gln
        195                 200                 205

Leu Gly Ala Asp Ala Asp Cys Phe Leu Gly Thr Asn Cys Pro Pro Val
    210                 215                 220

Arg Ile Asn Gly Lys Gly Gly Leu Pro Gly Gly Lys Val Lys Leu Ser
225                 230                 235                 240

Gly Ser Ile Ser Ser Gln Tyr Leu Ser Ser Leu Leu Met Ala Ala Pro
                245                 250                 255

Leu Ala Leu Glu Asp Val Glu Ile Glu Ile Ile Asp Lys Leu Ile Ser
            260                 265                 270

Val Pro Tyr Val Glu Met Thr Leu Lys Leu Met Glu Arg Phe Gly Val
        275                 280                 285
```

```
Thr Ala Glu His Ser Asp Ser Trp Asp Arg Phe Tyr Ile Lys Gly Gly
    290                 295                 300

Gln Lys Tyr Lys Ser Pro Gly Asn Ala Tyr Val Glu Gly Asp Ala Ser
305                 310                 315                 320

Ser Ala Ser Tyr Phe Leu Ala Gly Ala Ala Ile Thr Gly Gly Thr Val
                325                 330                 335

Thr Val Glu Gly Cys Gly Thr Thr Ser Leu Gln Gly Asp Val Lys Phe
            340                 345                 350

Ala Glu Val Leu Glu Met Met Gly Ala Lys Val Thr Trp Thr Asp Thr
                355                 360                 365

Ser Val Thr Val Thr Gly Pro Pro Arg Gln Pro Phe Gly Arg Lys His
370                 375                 380

Leu Lys Ala Val Asp Val Asn Met Asn Lys Met Pro Asp Val Ala Met
385                 390                 395                 400

Thr Leu Ala Val Val Ala Leu Phe Ala Asp Gly Pro Thr Ala Ile Arg
                405                 410                 415

Asp Val Ala Ser Trp Arg Val Lys Glu Thr Glu Arg Met Val Ala Ile
            420                 425                 430

Arg Thr Glu Leu Thr Lys Leu Gly Ala Thr Val Glu Glu Gly Pro Asp
                435                 440                 445

Tyr Cys Ile Ile Thr Pro Pro Glu Lys Leu Asn Ile Thr Ala Ile Asp
450                 455                 460

Thr Tyr Asp Asp His Arg Met Ala Met Ala Phe Ser Leu Ala Ala Cys
465                 470                 475                 480

Ala Glu Val Pro Val Thr Ile Arg Asp Pro Gly Cys Thr Arg Lys Thr
                485                 490                 495

Phe Pro Asn Tyr Phe Asp Val Leu Ser Thr Phe Val Lys Asn
                500                 505                 510

<210> SEQ ID NO 28
<211> LENGTH: 211
<212> TYPE: PRT
<213> ORGANISM: Sunflower

<400> SEQUENCE: 28

Met Ala Ile His Ile Asn Asn Ile Ser Asn Phe Thr Ser Asn Leu Thr
1               5                   10                  15

Asn Thr His Asn Pro Asn Ser Ser Lys Ser Ser Pro Ser Ser Phe
                20                  25                  30

Leu Ser Phe Gly Ser Asn Phe Asn Asn Pro Met Met Asn Leu Ala Ser
            35                  40                  45

Val Ser Cys Lys Gln Asn Asp Gln Lys Arg Ser Pro Ala Val Ala Ala
50                  55                  60

Ser Val Ala Thr Thr Gln Lys Thr Ser Thr Ala Pro Glu Glu Ile Val
65                  70                  75                  80

Leu Lys Pro Ile Lys Glu Ile Ser Gly Thr Val Asn Leu Pro Gly Ser
                85                  90                  95

Lys Ser Leu Ser Asn Arg Ile Leu Leu Leu Ala Ala Leu Ala Glu Gly
            100                 105                 110

Thr Thr Val Val Glu Asn Leu Leu Asn Ser Asp Asp Val His Tyr Met
        115                 120                 125

Leu Gly Ala Leu Arg Ala Leu Gly Leu Asn Val Glu Glu Asn Gly Glu
    130                 135                 140

Ile Lys Arg Ala Thr Val Glu Gly Cys Gly Gly Val Phe Pro Val Gly
145                 150                 155                 160
```

```
Lys Glu Ala Lys Asp Glu Ile Gln Leu Phe Leu Gly Asn Ala Gly Thr
            165                 170                 175

Ala Met Arg Pro Leu Thr Ala Ala Val Thr Ala Ala Gly Gly Asn Ser
            180             185                 190

Ser Tyr Ile Leu Asp Gly Val Pro Arg Met Arg Glu Arg Pro Ile Gly
        195             200                 205

Asp Leu Val
    210
```